US008481706B2

(12) United States Patent
Alves et al.

(10) Patent No.: US 8,481,706 B2
(45) Date of Patent: Jul. 9, 2013

(54) METHOD FOR OVERPRODUCING SPECIFIC RECOMBINANT PROTEIN WITH *P. CINNABARINUS* MONOKARYOTIC STRAINS

(75) Inventors: Alexandra M. C. R. Alves, Ne Haren (NL); Eric Record, Marseilles (FR); Anne Lomascolo, Marseilles (FR); Jean-Claude Sigoillot, Six Fours les Plages (FR); Marcel Asther, La Ciotat (FR); Han A. B. Wösten, Sn Zeist (FR)

(73) Assignees: Institut National de la Recherche Agronomique, Paris (FR); Universite de Provence, Marseilles (FR)

( * ) Notice: Subject to any disclaimer, the term of this patent is extended or adjusted under 35 U.S.C. 154(b) by 1686 days.

(21) Appl. No.: 10/586,348

(22) PCT Filed: Jan. 14, 2005

(86) PCT No.: PCT/FR2005/000093
§ 371 (c)(1),
(2), (4) Date: Oct. 13, 2006

(87) PCT Pub. No.: WO2005/073381
PCT Pub. Date: Aug. 11, 2005

(65) Prior Publication Data
US 2008/0305521 A1 Dec. 11, 2008

(30) Foreign Application Priority Data
Jan. 15, 2004 (FR) ..................................... 04 00366

(51) Int. Cl.
*C07H 21/04* (2006.01)
*C12N 15/00* (2006.01)
*C12N 1/00* (2006.01)
*C12N 9/00* (2006.01)
*C12N 9/02* (2006.01)
*C12P 21/04* (2006.01)

(52) U.S. Cl.
USPC .................. 536/24.1; 435/320.1; 435/254.11; 435/71.1; 435/183; 435/189

(58) Field of Classification Search
None
See application file for complete search history.

(56) References Cited

U.S. PATENT DOCUMENTS
6,551,797 B1    4/2003    Pfaller et al.

FOREIGN PATENT DOCUMENTS
EP    0 300 466    1/1989
JP    2001 157586    6/2001

OTHER PUBLICATIONS

Halaouli et al. (Characterization of a new tyrosinase from *Pycnoporus* species with high potential for food technological applications, Journal of Applied Microbiology, published online in Nov. 2004, 98, pp. 332-343).*
Rigaut et al. (A generic protein purification method for protein complex characterization and proteome exploration, Nature Biotechnology, vol. 17, 1999, pp. 1030-1032).*
Alves Alexandra M C R et al:, "Highly efficient production of laccase by the basidiomycete pycnoporus cinnabarinus", Applied and Environmental Microbiology, vol. 70, No. 11, Nov. 2004, pp. 6379-6384, XP002341841 ISSN: 0099-2240 le document en entier -& Database EMBL "Online! Feb. 1, 2005, "Pycnoporus cinnabarunus laccase gene, promoter region, 5' UTR and partial cds.", XP002341845, extrait de EBI accession No. AY534884 le document en entier.
Record Eric et al:, "Expression of the Pycnoporus cinnabarinus laccase gene in Aspergillus niger and characterization of the recombinant enzyme", European Journal of Biochemistry, vol. 269, No. 2, Jan. 2002, pp. 602-609, XP002295718, ISSN: 0014-2956, le document en entier.
Eggert Claudia et al:, "Molecular analysis of a laccase gene from the white rot fungus Pycnoporus cinnabuarinus", Applied and Environmental Microbiology, vol. 64, No. 5, May 1998, pp. 1766-1772, XP002295719, ISSN: 0099-2240, le document en entier -& EMBL "Online! May 13, 1998, Eggert C et al:, "Pycnoporus cinnabarinus laccae (lcc3-1) gene, complete cds.", XP002295723, Database accession No. AF025481, le document en entier.
Herpoel Isabelle et al:, "Selection of Pycnoporus cinnabarinus strains for laccase production", FEMS Microbiology Letters, vol. 183, No. 2, Feb. 15, 2000, pp. 301-306, XP002295720, ISSN: 0378-1097, le document en entier.
Sigoillot C et al:, "Lignocellulolytic and hemicellulolytic system of Pycnoporus cinnabarinus: Isolation and characterization of a cellobiose dehydrogenase and a new xylanase", Enzyme and Microbial Technology, vol. 31, No. 6, Nov. 1, 2002, pp. 876-883, XP002295721, ISSN: 0141-0229, le document en entier.
Schuren Frank H J et al:, "Highly-efficient transformation of the homobasidiomycete Schizophyllum commune to phleomycin resistance", Current Genetics, vol. 26, No. 2, 1994, pp. 179-183, XP008051258, ISSN: 0172-8083, figure 1.
Wessels J G H et al:, "Expression of Dikaryon-Specific Messenger RNA of Schiophyllum-Commune in Relation to Environmental Conditions and Fruting", Journal of General Microbiology, vol. 133, No. 9, 1987, pp. 2557-2562, XP008051259, ISSN: 0022-1287, tableau 1.
Database EMBL 'Online!, Sep. 19, 2000, "Pycnoporus cinnabarinus lacccase (lac1) mRNA, complete cds.", XP002341846, extrait de EBI accession No. EM_FUN:AF152170, Database accession No. $AF_1$152170, le document en entier.
Martinez AT : "Fungal metalloenzymes oxidizing aromatic compounds of industrial interest" 'Online!, Nov. 25, 2003, XP002295843, Extrait de l'Internet:, URL:http//www.cib.csic.es/lignina/pelas/pelas.html> extrait le Sep. 10, 2004 alinea '0005!
Lomascolo A et al:, "Overproduction of laccase by a monokaryotic strain of Pycnoporus cinnabarinus using ethanol as inducer.", Journal of Applied Microbiology, vol. 94, No. 4, 2003, pp. 618-624, XP002295716, ISSN: 1364-5072, le document en entire.

(Continued)

*Primary Examiner* — Suzanne M Noakes
*Assistant Examiner* — Jae W Lee
(74) *Attorney, Agent, or Firm* — Young & Thompson

(57) ABSTRACT

The use of monokaryotic strains of filamentous fungi of the *Pycnoporus* species of the basidiomycete group, for implementing a method for preparing a specific recombinant protein, the method being carried out by overexpressing the gene encoding the protein in the *Pycnoporus* monokaryotic strain.

24 Claims, 13 Drawing Sheets

OTHER PUBLICATIONS

Sigoillot Jean-Claude et al:, "Laccase production by a monokaryotic strain of Pycnoporus cinnabarus derived from a dikaryotic strain", World Journal of Microbiology and Biotechnology, vol. 15, No. 4, Aug. 1999, pp. 481-484, XP008035159, ISSN: 0959-3993, le document en entire LE.

Otterbein Ludovic et al:, "Molecular cloning of the cDNA encoding lacasse from Pycnoporus cinnararinus I-937 and expression in ichia pastoris", European Journa of Biochemistry vil. 267, No. 6, Mar. 2000, pp. 1619-1625, XP002295717, ISSN: 0014-2956, le document en entire—& Database EMBL "Online! Nov. 24, 1999, Otterbein L et al:, "Pycnoporus cinnabarinus laccase (lac1) gene, complete cds.", XP002295722, Database accession No. AF170093 le document en entire.

* cited by examiner

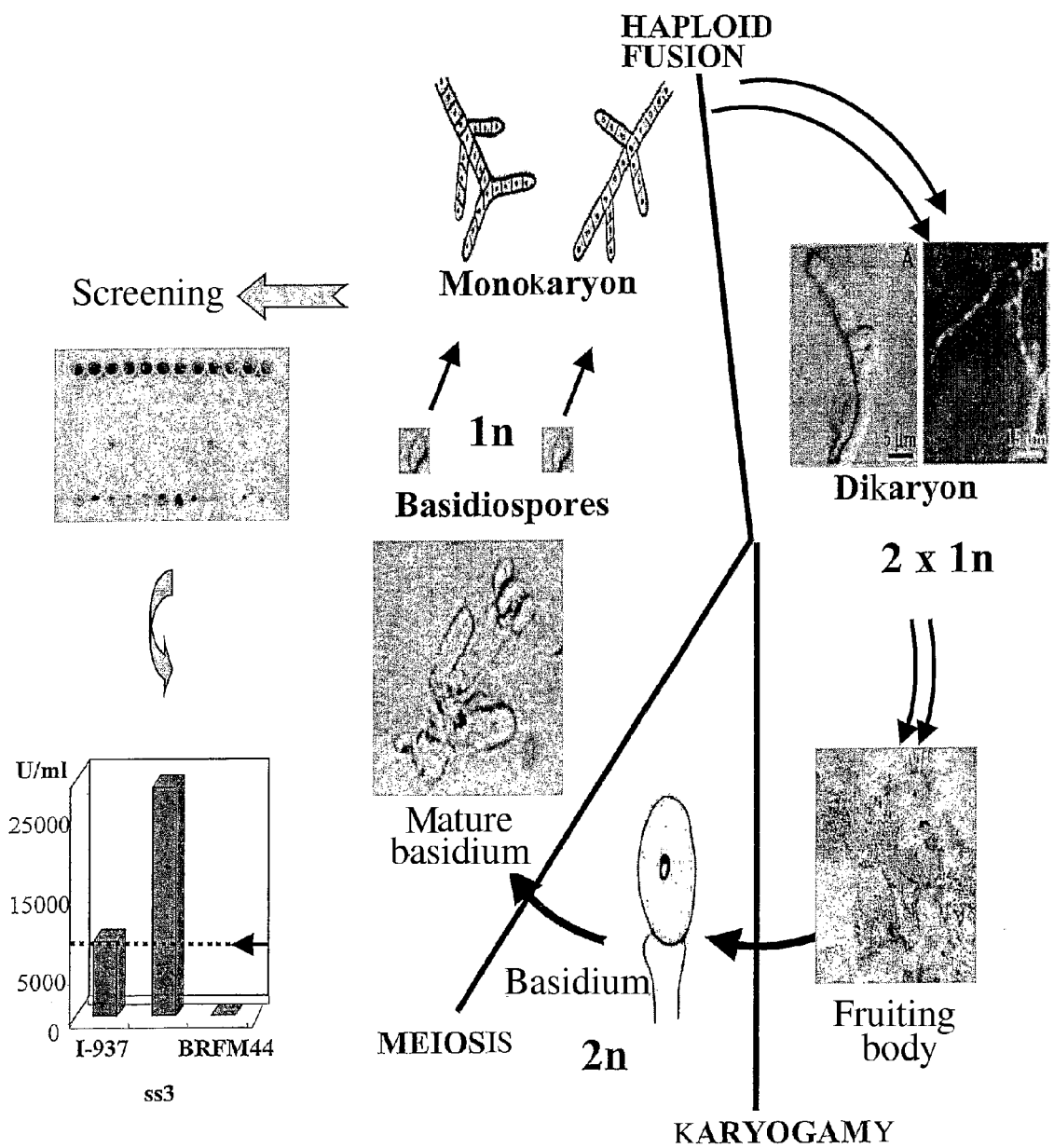
Figure 1 : Isolation of monokaryotic strain deficient in laccase activity.

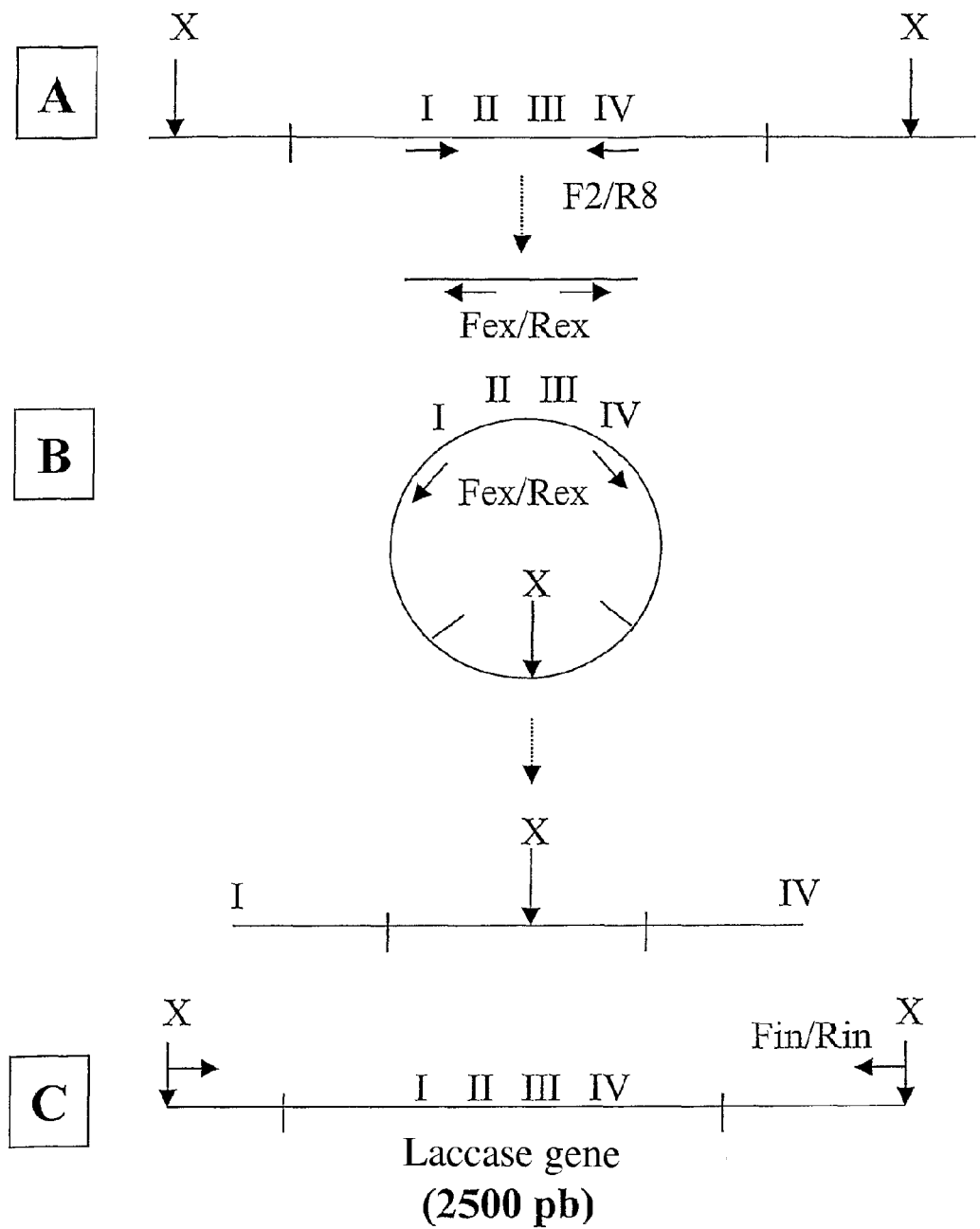
Figure 2: Isolation of the gene coding for the laccase of *Pycnoporus cinnabarinus* laccase.

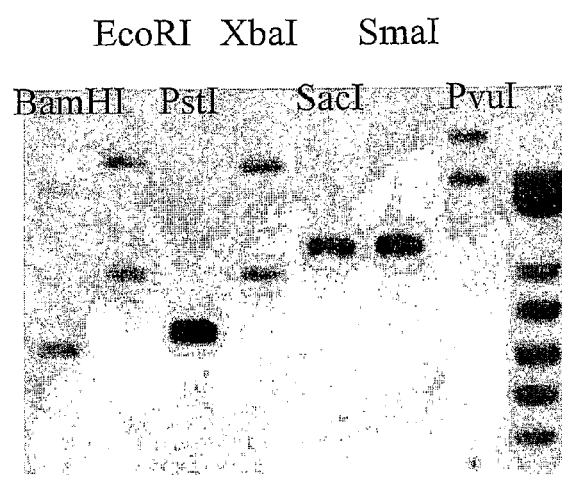
Figure 3: Southern blot study of the gene coding for the laccase of *Pycnoporus cinnabarinus*.

```
CTGCAGACATCTGGAGCGCCTGTCTTTCCCCTAGTATAAATGATGTCTGTCCGCAGGTCCTTGAAGACCGCTCGAGTCCCACTTGAGTTTTAGGTAGGAC      100
CTGTCCACCAAACCCCTCTTTCTGATCATGTCGAGGTTCCAGTCCCTCTTCTTCTTCGTCCTCGTCTCCCTCACCGCTGTGGCCAACGCAGCCATAGGGC      200
                    M  S  R  F  Q  S  L  F  F  F  V  L  V  S  L  T  A  V  A  N  A  A  I  G  P  25
CTGTGGCGGACCTGACCCTTACCAATGCCCAGGTCAGCCCCGATGGCTTCGCTCGCGAGGCCGTCGTGGTGAACGGTATCACCCCTGCCCCTCTCATCAC      300
 V  A  D  L  T  L  T  N  A  Q  V  S  P  D  G  F  A  R  E  A  V  V  V  N  G  I  T  P  A  P  L  I  T  58
AGGCAATAAGgtatgtatatgctgctcgtccctcagagctacatacatctgatccacaatcgtttagGGCGATCGATTCCAGCTCAATGTCATCGACCAG      400
 G  N  K                                                            G  D  R  F  Q  L  N  V  I  D  Q    72
                                                                                               F2
TTGACAAATCATACCATGTTGAAAACATCTAGTATTgtaaggggttcagttttcccgactaccatgttattgaccatcaccactcgtag CATTGGCACGG    500
 L  T  N  H  T  M  L  K  T  S  S  I                                                       H  W  H  G   88
                                                                                           (I)
CTTCTTCCAGCAAGGCACGAACTGGGCCGATGGTCCCGCGTTCGTGAACCAGTGTCCCATCGCTTCGGGCCACTCGTT CTTGTATGACTTTCAAGTTCCC   600
 F  F  Q  Q  G  T  N  W  A  D  G  P  A  F  V  N  Q  C  P  I  A  S  G  H  S  F  L  Y  D  F  Q  V  P    121
 (I)
GACCAAGCAGgtacgaattccgtacacgtttcattgcgtcgcaactaaacctcctcttactagGGACTTTCTGGTACCATAGCCATCTCTCCACGCAATA    700
 D  Q  A  A                                                      T  F  W  Y  H  S  H  L  S  T  Q  Y   137
 (II)                                                            (II)
CTGCGATGGTTTGAGGGGGCCTTTCGTCGTCTACGACCCCAACGATCCTCACGCTAGCCTGTATGACATTGATAACGgtgagcagatcatggtatcgcaa     800
 C  D  G  L  R  G  P  F  V  V  Y  D  P  N  D  P  H  A  S  L  Y  D  I  D  N  D                          163
tattgcgtccacttatgcttcctggcatccagACGACACTGTCATTACGCTGGCTGATTGGTATCACGTTGCTGCCAAGCTCGGACCTCGCTTCCCgtac     900
                                   D  T  V  I  T  L  A  D  W  Y  H  V  A  A  K  L  G  P  R  F  P     184
gtgtcaaatgtctacgagagatctcacatatacgactagactcacttcgctgattacagATTTGGCTCCGATTCAACCCTTATCAATGGACTTGGTCGAA    1000
                                                            F  G  S  D  S  T  L  I  N  G  L  G  R  T  198
CCACTGGCATAGCCACCGTCCGACTTGGCAGTTATCAAGGTCACGCAGGGCAAGCGgtaagtatggatggtcatcactgcacattggctctgatacatggc    1100
 T  G  I  A  P  S  D  L  A  V  I  K  V  T  Q  G  K  R                                                  216
cttgtttccacagCTACCGCTTCCGCTTGGTGTCGCTTTCTTGCGATCCGAACCATACATTCAGCATTGATAATCACACAATGACTATAATTGAGGCGGA    1200
             Y  R  F  R  L  V  S  L  S  C  D  P  N  H  T  F  S  I  D  N  H  T  M  T  I  I  E  A  D    245
CTCGATCAACACTCAACCCTCAGAGGTTGATTCAATCCAGATTTTTGCCGCGCAGCGCTACTCCTTCGTGgtaggtcgtaggctcctgtcatcaagtttg    1300
 S  I  N  T  Q  P  L  E  V  D  S  I  Q  I  F  A  A  Q  R  Y  S  F  V                                   268
cagacattcttagatacacctttttcaatgcagCTGGATGCTAGCCAGCCGGTGGATAACTACTGGATCCGCGCAAACCCTGCCTTCGGAAACACAGGTT    1400
                                 L  D  A  S  Q  P  V  D  N  Y  W  I  R  A  N  P  A  F  G  N  T  G  F  291
TTGCTGGTGGAATCAATTCTGCCATCCTGCGTTATGATGGCGCACCCGAGATCGAGCCTACGTCTGTCCAGACTACTCCTACGAAGCCTCTGAACGAGGT    1500
 A  G  G  I  N  S  A  I  L  R  Y  D  G  A  P  E  I  E  P  T  S  V  Q  T  T  P  T  K  P  L  N  E  V    324
CGACTTGCATCCTCTCTCGCCTATGCCTGTGgtacgtgtctcaaagaacctcgatcactaagtgcatgtcaactcatatggtgcatgacagCCTGGCAGC    1600
 D  L  H  P  L  S  P  M  P  V                                                                P  G  S   337
CCCGAGCCCGGAGGTGTCGACAAGCCTCTGAACTTGGTCTTCAACTTCgtgagtactggcgcgcttccgtagcacacgttcgaacaaagcctgataccat    1700
 P  E  P  G  G  V  D  K  P  L  N  L  V  F  N  F                                                       353
gcagAACGGCACCAACTTCTTCATCAACGACCACACCTTTGTCCCGCCGTCTGTCCCAGTCTTGCTACAAATCCTCAGTGGGGCGCAGGCGGCTCAGGAC    1800
     N  G  T  N  F  F  I  N  D  H  T  F  V  P  P  S  V  P  V  L  L  Q  I  L  S  G  A  Q  A  A  Q  D    385
CTGGTCCCGGAGGGCAGCGTGTTCGTTCTTCCCAGCAACTCGTCCATTGAGATATCCTT CCCTGCCACTGCCAATGCCCCTGGATTCCCCCATCCGTTCC    1900
 L  V  P  E  G  S  V  F  V  L  P  S  N  S  S  I  E  I  S  F  P  A  T  A  N  A  P  G  F  P  H  P  F  H  419
                                                                                            (III)
ACTTGCACGGTgtacgtctgccttccctcgtctaaaggcggagtcgatatctgactcccatcacagCACGCCTTCGCTGTCGTCCGGAGCGCC GGGAGC    2000
 L  H  G                                                           H  A  F  A  V  V  R  S  A  G  S    433
 (III)                                                             (III)
AGCGTCTACAACTACGACAACCCGATCTTCCGCGACGTCGTCAGCACCGGCCAGCCCGGCGACA ACGTCACGATTCGCTTCGAGACCAATAACCCAGGCC    2100
 S  V  Y  N  Y  D  N  P  I  F  R  D  V  V  S  T  G  Q  P  G  D  N  V  T  I  R  F  E  T  N  N  P  G  P  467
                                                                 R8
CGTGGTTCCTCCACTGCCACATTGACTTCCACCTCGACGCAGGCTTTGCTGTAGTCATGGCCGAGGACACTCCGGACACCAAGGCCGCGAAC CCTGTTCC    2200
 W  E  L  H  C  H  I  D  F  H  L  D  A  G  F  A  V  V  M  A  E  D  T  P  D  T  K  A  A  N  P  V  P    500
 (IV)   (IV)        (IV)
TCAGGCGTGGTCGGACTTGTGCCCCATCTATGATGCACTTGACCCCAGCGACCTCTGAGCGGGATTGTTACTGTGACCTGGT GTGGGGGAACATGTCGA     2300
 Q  A  W  S  D  L  C  P  I  Y  D  A  L  D  P  S  D  L                                                 518
GGGCTTTCATCGATCAGGGACTTTCAAGGTTGGCATAATATACCTCACGGCCTGGATGACTCGGACAGCGTGTGGGCGTGGGTGTAACTCTGCTTGATGT    2400
TGAAAAAAGGATTTTATGTAGAACAATTTATGAGCAATCAGCAATCAATAGGATTGTGTCGGTTTCGACGAAATGTCTTGTCTCCCTGACATTACTTTTG    2500
TGCGAGAAATGGGTCCATGATACACATCATTGAGCTCTCAATACCAAGAAGGATTACCCATGTCAATACCCAAGATCATGTCTTCGCTGTCCGCAATGG    2600
TCTCATGTTGCGTTGAGCAGATCGCAGTACGTTGAAAAGCGATTAGTATTACATGCAACATGCAACATTTGGAAGGGGGCATGCAGAGGTTCAGCTCGCG    2700
TCAGTCGCCAAGTAGCGACCTTTGCCGCACTGCCTGTTAACCTGAACGTATGCTTCAGAACTCCGTCGGTATCGAGAGCGATCGTGTACGTTCCGGGAT    2800
AGATCCATTGATCCCCGCTCTGGTCGGCGCGTGCGATGGCCCCGAGCGTCACCGGCAGCTTCGCGATCGCGCTTTTCCTAGGGGCGAGGCCGTGTACCCG    2900
CGTGTACGAGACGAGCTGCTTGTTCGGGTGGGGCGAAGGCCCGAAGGAGCCACTCACGAAGAGCAATGCGACGTAATCCGAGGTAGCCTTGCCCGTGTTA    3000
GTCACACGCACGGAGAACGTGTCGAGCGGCGCGAGGTCGAGGAAGGCGGCGCTCTTCTGACCGCGCTGTACGAGGTCGGAAATCGAATACGTCGATGCG    3100
GTCCTCCAAAGTCCGTGACGTTGGTCGCATCGGCCGCCGCGCCTGGAGCTGCCCAAGAGAAATCGAAGGTGGTGAAGTGCAGTCCAAAGCCAAATTCGTA    3200
GACCGGCGTGCCGGTGTACCACTTGTATGTACGCCCCGGGTTCGACCGCGCTTGGGCGAAGGGT CATGTCAGTCATCGGAACCTGATCAGCGTAGATGGCT    3300
GGGTATTGGGTGATGGGCAGGCGTCCTGCAG                                                                        3331
```

Figure 4 : Sequence of the gene coding for the laccase of *Pycnoporus cinnabarinus*

```
AGATCTCCGAACCAGAAATGCGATTGCGTTCAGGCCCAATTAAGAATAAAGCTGCGTCAGGGCAGCGACGTA
TCTTGATCCATCATTGACTCACCGGCATCGGCGTCAACACCAAAGCAAGCTCGTCCCACCCATAGGCGTGCA
CCGGCCGGCGTGCGCCATTGAGGTACATGAGCGGGGCGAAAGTCCGCCATTGGTAGCCCTGTCGTGGACGCG
CGGCGATGAAACGTTTCCCACCATTGGGAAGAAACGTCTGCGGCCCATCATCCCTTCACCGGATGACAAGGC
GGCGTCGCGCCTTTGCCGCAGAGGCCGGCGGGCGACATGCACAGCGAAGGTCCGTTGCGGATGGGAAGCAGG
CAATCAGTGGGTGTCCTACGCCGCCACGATGGTCGGGGAGCGTAGGCGCCCTCCCATAAGGCGGCAAGCATC
ATGATGCTCTCCGATTCGGGAAGCCTGGTGCGATGCTGGAGAGACTCTCTCCGAGAGACCAGTGTGCGCAAC
GTTCCTGGCCTGGAAGACTTTAAAGTGAGTGTAGAAGGGCGAGCAGAGGACGATCATCGGATTGCAGGAACC
ATCGGCATCCTCAGCCTGGGAAGGATGGCTCTTGGTAGACATTCGCGGAAGGTGTCCTAGATGTGAGCGGGC
TTCTTGGATGATCATGTCGTAACTTTTTCTGACCTCGTCGGTGGTACGCATGGCAGGATTGAGCATTACGGT
ATGCCTCCCATTCATAAACGATAACCCCTTCCTTCAGGTTGGTCATCTCCATAGAGCGGCACGCTCTCAAGG
CCTAGGCTATTCACACCTCCTTCGCAACATCCCTATTCACGGTGTCTGTAAGGAACGACTTGTCATGGGATC
ACATGAAGTGCAGCATACTGTTCGCCGGTCTCGCAGTACAGACGCTAGTACGGGAAGTCGACATCCAAGCGT
TCAGTCACCACATGGCAAAAAAGCTGCACCATACTCTTTATGGTGAGTTGTTCGTGAGTGGTATACAGTCAT
TCATGAGGGAATGCCCACCGGATAGGGTGTGGCGGCCGCAATATTCATCGCCTGGCAATAGTCGATGTGCGT
CCTTGTTCAATGAATATCATGGGTCACATGTGGAGACGGTTAAACAGCGTTGACTGTGAATCCCTGGTGTGT
GTTGGGCCGAACAGGTACGTTGCAGGAACACCAATATCTCTTCGGCAGCCCAGTTCTTTGCGAGCGGCACAG
GCAGGCATCGCGCAACAGATCCCAGCCATCCGGCCTCTGACATTCGGGATACCTGAAGCCCTTCAGGTACGG
AGCGAAGAGGTGGGCTCTCTGCAGCGATTGGCGGACGGATAGCTGTATTTCCTCTCTCACCATTGGGAAGAT
GTGAAAGGCTCCATCATATAGCGGCTCAACTCTACCTCGAATGTCCAAACACGGCGGGAATACTTATTTATG
TGGACAAGGCCGAGCTATGATAGCTTGCTCCCGAAGTTGGTAAGTCCCGCAATCTGCGGTTCAGGCAACAGT
CTCGGAAAAATAAGAAGAATATTGTAGGTGCGTGTAGGCGTATCGCCCAAATGCGCACACACGGAGGCTTTA
GGAGATGAAGCGCCCGTGAGCGGTAAGGGAGTTGGTTCACCGCCGCCCCGACCGACTCTCTCTCTTTCCCAG
CATCATGTCTCGGCGCAAACTTTACCCTCTATTGACCAACTCCACGAGAAAGCAGGAACAGCTTCCTTGTCT
CTCATGACGTCCGCAATCCAGACCCTTAGCCGGTTCGTTACTCATCGTTATCCCTGCCGCCATGGTAGTGGA
GTCAGCCTGGCCAGTGCGTAGTCCCGTCTCTCTTGCTGCACTAGAGAAGCCCCATGAGACAGCGTTTTTTGC
TTTATTTCTGCTGTTTCTATAGACACCATAGGGGCAAACGATCCTGCACGCCCAGAGGTATTGGGCTCGTCA
GATTCCCAGTTTTTCTCCTCGGTCTGAATCGGCTGCACGGCAGATAAATCGGCCGGAAATGCTATAGCCCTT
CATAGCCCGCTATGAGAGTCGCAAAAGGCTTGTCAGTCAGGTCGGTCGAGTGGCTCTCACGAAGAGCGTCAA
CTTCGCGCGACAGCCGCCTTTCAGGGCAAGATAGATCCTCCCATCATCCCCTACTGCGCTCAGCGCCGGTAC
CGAACAATTGACTTACCGACATCCTCCGGGACGCGCAAATGCTGTTCGACGGAACGTAATCCTCTTCGTCCC
GCCTCTTTTCGCTCTCACGCATTCCGTGTGGTTCGCGCGACGGCCGCTCATCAGGACCAGACCAGTCTCAAT
GTCTGGTACCGGCACAATGGTGACACTGCGGCAACTGAGTAGGTCTGGTCACTCTGGTGCACCGTCGCTTAC
GCTGACCTTCGGGATACTGTCCTGCAGACATCTGGAGCGCCTGTCTTTCCCCTAGTATAAATGATGTCTGTC
CGCAGGTCCTTGAAGACCGCTCGAGTCCCACTTGAGTTTTAGGTAGGACCTGTCCACCAAACCCCTCTTTCT
GATCATG
```

Figure 5 : Sequence of the promoter sequence of the gene coding for the laccase of *Pycnoporus cinnabarinus* (up to the ATG coding for the methionine of the laccase).

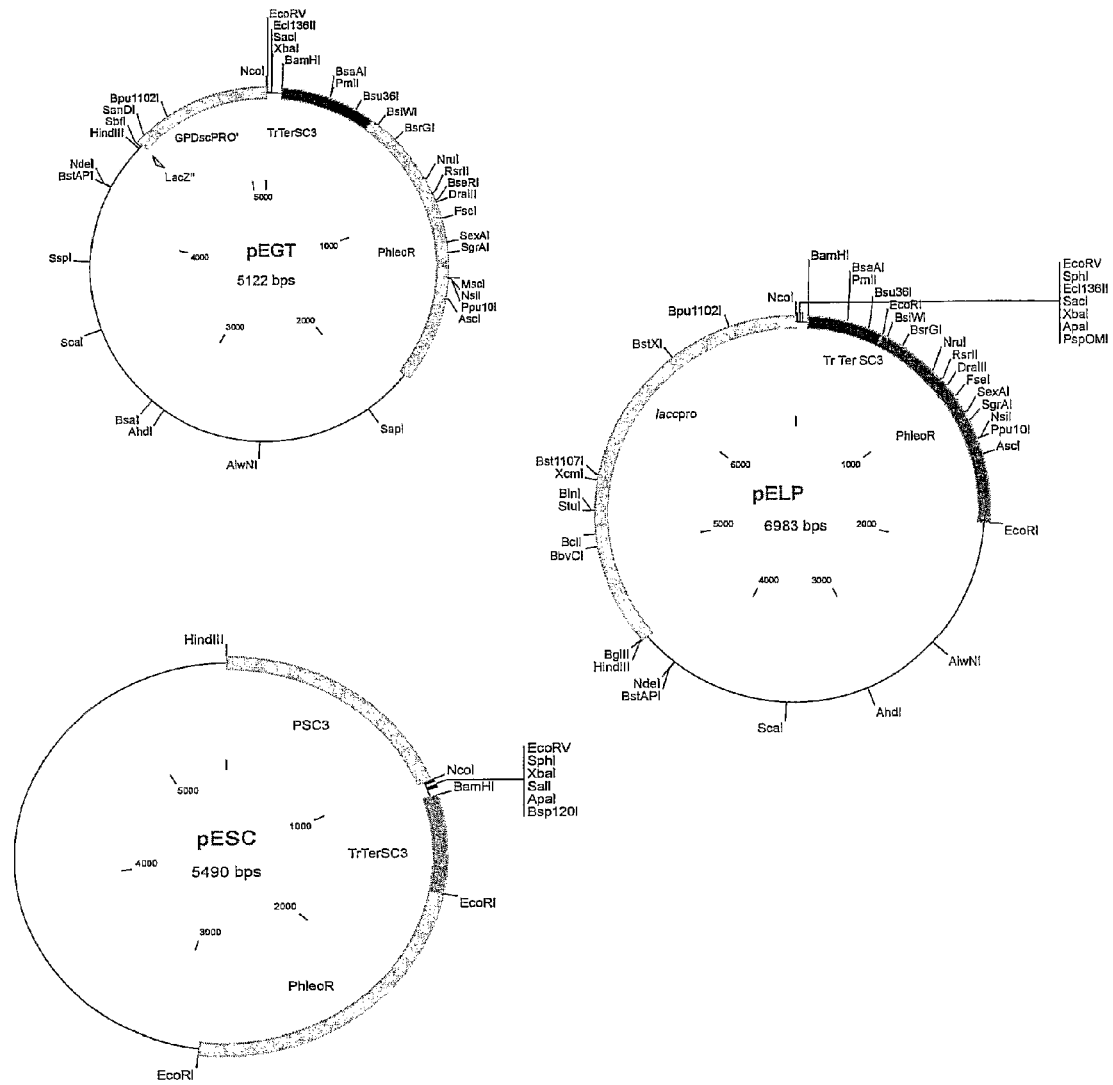
Figure 6 : Restriction map of the three expression vectors used for the production of laccase in *Pycnoporus cinnabarinus*.

```
CATGGGATATCGCATGCCTGCAGAGCTCTAGAGTCGACGGGCCCGGTACCGCGGCCGCCTTAAGACGCGTGGATCCGCAGGTGAAC
GCGCCTATCGGTGGGATATTCGGGCGACGGGAGCCTCGGCAATCTGAGCCTCGTTACTGCCTAGCAAATTCGGAATCCCTTCGATGT
CATAGGGTCGCGGACAAGTGATCGTCTTGCTACATACTCCAAGGTGTTGACTCATTCCCTCGATAATGAACATTGTTGTTGTTGTTTG
TTCTCTATCCGCTCAGTCACGCGACCCCACACGTGCATGGTTGAACTTCGCCACGCAACAACCGCATGACGACATGGCGAACCTAAG
TAAAGGCTGAGTCGTGGACTAAAGCACTCCACTTTACGGCGAGGATGCCAGTCTACGTCATGAATGAAGCCTCAGGTCCCGAAGTAA
GGGGGTACAAAAGGAGGGTGAAAGGTGGACGTTTTCTTACCATCCTTCCACCTCCCAGACCACCATGCCGGGAATTCCCAGCTTGCT
CAAAAAGGTTCTGCCCGTACGCCCGCGAAATTCCTTCGAGGTGGCCCCTATCGCATACATGCACGACTTCAAAACATCCATTCTATC
ATTTTGGGATCGTACAATTATTAGACATGTTGTACAACGTTACATTCCTTTCTTCTTTTACTCTCCGGCCCAGTCTATGTAGAGGTAAA
GTACAAGCGTCCAAAGGATCAGGCACTTAGAGCGCGCCGTCTTGCTTCGCCGCTTAGAGCGCGCCGTCCTGCTTCGCCGCGTAGACG
AGCAGGTCGCAGACACGGCGGGAGTAGCCCCACTCGTTGTCGTACCAGGCAATGAGCTTCACGAAGCTCTTGCTGATCGCGATGCCG
GGGATCGATCCACGCGTCTTAAGGCGGCCGCGCGGTACCCCCTCGGACCCGTCGGGCCGCGTCGGACCGGCGGTGTTGGTCGGCGTCGG
TCAGTCCTGCTCCTCGGCCACGAAGTGCACGCAGTTGCCGGCCGGGTCGCGCAGGGCGAACTCCCGCCCCCACGGCTGCTCGCCGAT
CTCGGTCATGGCCGGCCCGGAGGCGTCCCGGAAGTTCGTGGACACGACCTCCGACCACTCGGCGTACAGCTCGTCCAGGCCGCGCAC
CCACACCCAGGCCAGGGTGTTGTCCGGCACCACCTGGTCCTGGACCGCGCTGATGAACAGGGTCACGTCGTCCCGGACCACACCGGC
GAAGTCGTCCTCCACGAAGTCCCGGGAGAACCCGAGCCGGTCGGTCCAGAACTCGACCGCTCCGGCGACGTCGCGCGCGGTGAGCA
CCGGAACGGCACTGGTCAACTTGGCCATGCATGGTGATGGGCATTATGTGTGATGGGATGCGATGGGAGAGGGAAGTGCTCTGGATG
GGAGTGCTGGAGAAAGAGGGAGACGGCGGGCGGCGCGCCTTTTATACCCACGCCCGAAAGATCCGATCGATACTGACAAAACGGGA
TGAACACATCGGCGGCGGCCTGGACTGCGCGCCATCTGCAAATGCCCAGCCAGTCCCGTCGGGCGCCACCACCAGCCCTGGTCGAGT
CCCCCTCGAGGGCGACGCTCTATTCTATCCATGCGCGCAATTGCAGGTGCGCGGTCGAAGAACAGTCCTTCGCAGTCTTCTCGCACC
TGGGCTGCGACCCTGTCTACCTCTCATCCTAACCCCTCCGCGGCTTCGCAGTACAGTTACTAATCTCACACCGAAGAGGCTCTCGCGC
CACCCTCCGATCCCGAGCACGTTCCTTACATGCCACAGCGTCAGAATTGAACACAATGCACGTCARATCAGATCCCCGGGAATTCGT
AATCATGGTCATAGCTGTTTCCTGTGTGAAATTGTTATCCGCTCACAATTCCACACAACATACGAGCCGGAAGCATAAAGTGTAAAG
CCTGGGGTGCCTAATGAGTGAGCTAACTCACATTAATTGCGTTGCGCTCACTGCCCGCTTTCCAGTCGGGAAACCTGTCGTGCCAGCT
GCATTAATGAATCGGCCAACGCGCGGGGAGAGGCGGTTTGCGTATTGGGCGCTCTTCCGCTTCCTCGCTCACTGACTCGCTGCGCTCG
GTCGTTCGGCTGCGGCGAGCGGTATCAGCTCACTCAAAGGCGGTAATACGGTTATCCACAGAATCAGGGGATAACGCAGGAAAGAA
CATGTGAGCAAAAGGCCAGCAAAAGGCCAGGAACCGTAAAAAGGCCGCGTTGCTGGCGTTTTTCCATAGGCTCCGCCCCCCTGACG
AGCATCACAAAAATCGACGCTCAAGTCAGAGGTGGCGAAACCCGACAGGACTATAAAGATACCAGGCGTTTCCCCCTGGAAGCTCC
CTCGTGCGCTCTCCTGTTCCGACCCTGCCGCTTACCGGATACCTGTCCGCCTTTCTCCCTTCGGGAAGCGTGGCGCTTTCTCATAGCTC
ACGCTGTAGGTATCTCAGTTCGGTGTAGGTCGTTCGCTCCAAGCTGGGCTGTGTGCACGAACCCCCCGTTCAGCCCGACCGCTGCGCC
TTATCCGGTAACTATCGTCTTGAGTCCAACCCGGTAAGACACGACTTATCGCCACTGGCAGCAGCCACTGGTAACAGGATTAGCAGA
GCGAGGTATGTAGGCGGTGCTACAGAGTTCTTGAAGTGGTGGCCTAACTACGGCTACACTAGAAGGACAGTATTTGGTATCTGCGCT
CTGCTGAAGCCAGTTACCTTCGGAAAAAGAGTTGGTAGCTCTTGATCCGGCAAACAAACCACCGCTGGTAGCGGTGGTTTTTTTGTTT
GCAAGCAGCAGATTACGCGCAGAAAAAAAGGATCTCAAGAAGATCCTTTGATCTTTTCTACGGGGTCTGACGCTCAGTGGAACGAA
AACTCACGTTAAGGGATTTTGGTCATGAGATTATCAAAAAGGATCTTCACCTAGATCCTTTTAAATTAAAAATGAAGTTTTAAATCAA
TCTAAAGTATATATGAGTAAACTTGGTCTGACAGTTACCAATGCTTAATCAGTGAGGCACCTATCTCAGCGATCTGTCTATTTCGTTC
ATCCATAGTTGCCTGACTCCCCGTCGTGTAGATAACTACGATACGGGAGGGCTTACCATCTGGCCCCAGTGCTGCAATGATACCGCG
AGACCCACGCTCACCGGCTCCAGATTTATCAGCAATAAACCAGCCAGCCGGAAGGGCCGAGCGCAGAAGTGGTCCTGCAACTTTATC
CGCCTCCATCCAGTCTATTAATTGTTGCCGGGAAGCTAGAGTAAGTAGTTCGCCAGTTAATAGTTTGCGCAACGTTGTTGCCATTGCT
ACAGGCATCGTGGTGTCACGCTCGTCGTTTGGTATGGCTTCATTCAGCTCCGGTTCCCAACGATCAAGGCGAGTTACATGATCCCCCA
TGTTGTGCAAAAAAGCGGTTAGCTCCTTCGGTCCTCCGATCGTTGTCAGAAGTAAGTTGGCCGCAGTGTTATCACTCATGGTTATGGC
AGCACTGCATAATTCTCTTACTGTCATGCCATCCGTAAGATGCTTTTCTGTGACTGGTGAGTACTCAACCAAGTCATTCTGAGAATAG
TGTATGCGGCGACCGAGTTGCTCTTGCCCGGCGTCAATACGGGATAATACCGCGCCACATAGCAGAACTTTAAAAGTGCTCATCATT
GGAAAACGTTCTTCGGGGCGAAAACTCTCAAGGATCTTACCGCTGTTGAGATCCAGTTCGATGTAACCCACTCGTGCACCCAACTGA
TCTTCAGCATCTTTTACTTTCACCAGCGTTTCTGGGTGAGCAAAAACAGGAAGGCAAAATGCCGCAAAAAAGGGAATAAGGGCGAC
ACGGAAATGTTGAATACTCATACTCTTCCTTTTTCAATATTATTGAAGCATTTATCAGGGTTATTGTCTCATGAGCGGATACATATTTG
AATGTATTTAGAAAAATAAACAAATAGGGGTTCCGCGCACATTTCCCCGAAAAGTGCCACCTGACGTCTAAGAAACCATTATTATCA
TGACATTAACCTATAAAAATAGGCGTATCACGAGGCCCTTTCGTCTCGCGCGTTTCGGTGATGACGGTGAAAACCTCTGACACATGC
AGCTCCCGGAGACGGTCACAGCTTGTCTGTAAGCGGATGCCGGGAGCAGACAAGCCCGTCAGGGCGCGTCAGCGGGTGTTGGCGGG
TGTCGGGGCTGGCTTAACTATGCGGCATCAGAGCAGATTGTACTGAGAGTGCACCATATGCGGTGTGAAATACCGCACAGATGCGTA
AGGAGAAAATACCGCATCAGGCGCCATTCGCCATTCAGGCTGCGCAACTGTTGGGAAGGGCGATCGGTGCGGGCCTCTTCGCTATTA
CGCCAGCTGGCGAAAGGGGGATGTGCTGCAAGGCGATTAAGTTGGGTAACGCCAGGGTTTTCCCAGTCACGACGTTGTAAAACGAC
GGCCAGTGCCAAGCTTGCATGCCTGCAGGTCGACGACCGAGCGCGCGCCACCCAGCCTATCCCGCGCGGGTCGGGACCCAAAATAA
GCGGGCCCCGCCGCGCCCCGTCGGGCGAGCGGGTGTATCTACGAACGGAACTGGGAGGCGACTCGGAAGAGTTTGGTTAGAAAGGG
GAACACCATCGCGGACGGCCCAGTGCTCTGGCAGCTGTACTGAGAGTGCATTGTGTTCAATTCTGACCTGTGGCATGTAAGGAACGTGCTC
GGGATCGGAGGGTGGCGCGAGAGCCTCTTCGGTGTGAGATTAGTAACTGTACTGCGAAGCCGCGGAGGGGTTAGGATGAGAGGTAG
ACAGGGTCGCAGCCCAGGTGCGAGAAGGACTGCGAAGGACTGTTCTTCGACCGCGCACCTGCAATTGCGCGCATGGATAGAATAGA
GCGTCGCCCTCGAGGGGGACTCGACCAGGGCTGGTGGTGGCGCCCGACGGGACTGGCTGGGCATTTGCAGATGGCGCGCAGTCCAG
GCCGCCGCCGATGTGTTCATCCCGTTTTGTCAGTATCGATCGGATCTTTCGGGCGTGGGTATAAAAGCGCGCCGCCCGCCGTCTCCCT
CTTTCTCCAGCACTCCCATCCAGAGCACTTCCCTCTCCCATCGCATCCCATCACACAATAATGCCCATCAC
```

Figure 7: Nucleotide sequence of the vector pEGT, containing the gpd gene promoter (4480-5112), a phleomycin resistance marker (507-1822) and the sc3 gene terminater (71-507).

```
AGCTTCTCCGGCCCCGAATCGAACGGCAGGATGTGTGGGCGTGTCCAATATTGCCATGAAAATCTGTCAGAAGTGAGCCCTCTCGTCAC
CCTGTACAGCTTCGCTGAGTTGAAAAGCAGGGTTCATCTTGGGCTCACTGATGCACTGAGCTCGACCGGAGAACTAAATGACCAGCCGG
AGTGTTCACTAACTTAACGCCGGGTATTCAGGGCAGCTTCTCTATGTTGCGCCTACGACGTAGATCACCGCCCATGAACGGGGGAAACG
GGGAGGGGTGCGTTTGGTACGTCTTTACGTCTGGCTATGTTGTATTGACCAGCGTCTGCAGAAGATGGGCACGACGATGCGCCGAGCCG
GCCAGTGTCGTCGGATGTCCACTGTTGAGGCCATCCTTTTGCTAGACAGACGGAAGAGCTTTGGAGGTGCGATTCCTCTACGAATGGGA
AGGGGCTTAGATGGAGAGTGACACGTCTGAGCTCCCCAACACGCCTTCGCCGAGGGTGCGTCTCCGCGGACATTCACCTCAGTTCATTG
TTCTGACCTGCCTAATTGTATAGACCGGCCAACAACCTTGCTGACGCCCATCATAACAGTGCCCTGCACAGAGCCTTCCCACTCAGTCGG
CGCCTCCCTCAATCAATCCCACTAACTCGCCGGCTCTGCCCCTTCGCCGCTCGACACGTCGCTTGGAAGAGCCCGGGCACGGGCGTCCGC
TCCCCCCTTCCCTCCGCGTCGTCATGCACGCAGCGTTAATGTTGCTGCAGGCGAGCCGTAAGTATATTCAAAGGCGTAGCGAATGAATAG
CAGGCGCGCGGGGACCTGGCACGCGCGGCATGAACATGCAGACTTGGGTGACGATAACTTGAACTCAGACGCGGCGAATGAATATCCA
AACGCGCGGGAAGAAAATAATTTACGGGAGCCTCCCCAGGTATAAAAGCCCCTCACCCGCTCACTCTTTCTCCAGTCGAACACCCCAGT
TCAACTACCCAGCCCTTCCTTCCTTCGCTATCCTTCYTTACAACCTGCTCGCCATGGGATATCGCATGCCTGCAGAGCTCTAGAGTCGAC
GGGCCCGGTACCGCGGCCGCCTTAAGACGCGTGGATCCGCAGGTGAACGCGCCTATCGGTGGGATATTCGGGCGACGGGAGCCTCGGC
AATCTGAGCCTCGTTACTGCCTAGCAAATTCGGAATCCCTTCGATGTCATAGGGTCGCGGACAAGTGATCGTCTTGCTACATACTCCAAG
GTGTTGACTCATTCCCTCGATAATGAACATTGTTGTTGTTGTTTGTTCTCTATCCGCTCAGTCACGCACCCCACACGTGCATGGTTGAAC
TTCGCCACGCAACAACCGCATGACGACATGGCGAACCTAAGTAAAGGCTGAGTCGTGGACTAAAGCACTCCACTTTACGGCGAGGATGC
CAGTCTACGTCATGAATGAAGCCTCAGGTCCCGAAGTAAGGGGGTACAAAAGGAGGGTGAAAGGTGGACGTTTTCTTACCATCCTTCCA
CCTCCCAGACCACCATGCCGGGAATTCCCAGCTTGCTCAAAAAGGTTCTGCCCGTACGCCCGCGAAATTCCTTCGAGGTGGCCCCTATCG
CATACATGCACGACTTCAAAACATCCATTCTATCATTTTGGGATCGTACAATTATTAGACATGTTGTACAACGTTACATTCCTTTCTTCTT
TTACTCTCCGGCCCAGTCTATGTAGAGGTAAAGTACAAGCGTCCAAAGGATCAGGCACTTAGAGCGCGCCGTCTTGCTTCGCCGCTTAG
AGCGCGCCGTCCTGCTTCGCCGCGTAGACGAGCAGGTCGCAGACACGGCGGGAGTAGCCCCACTCGTTGTCGTACCAGGCAATGAGCTT
CACGAAGCTCTTGCTGATCGCGATGCCGGGGATCGATCCACGCGTCTTAAGGCGGCCGCGGTACCCCCTCGGACCCGTCGGGCCGCGTC
GGACCGGCCGGTGTTGGTCGGCGTCGGTCCTGCTCCTCGGCCACGAAGTGCACGCAGTTGCCGGCCGGGTCGCGCAGGGCGAACTC
CCGCCCCCACGGCTGCTCGCCGATCTCGGTCATGGCCGGCCCGGAGGCGTCCCGGAAGTTCGTGGACACGACCTCCGACCACTCGGCGT
ACAGCTCGTCCAGGCCGCGCACCCACACCCAGGCCAGGGTGTTGTCCGGCACCACCTGGTCCTGGACCGCGCTGATGAACAGGGTCACG
TCGTCCCGGACCACACCGGCGAAGTCGTCCTCCACGAAGTCCCGGGAGAACCCGAGCCGGTCGGTCCAGAACTCGACCGCTCCGGCGAC
GTCGCGCGCGGTGAGCACCGGAACGGCACTGGTCAACTTGGCCATGCATGGTGATGGGCATTATGTGTGATGGGATGCGATGGGAGAG
GGAAGTGCTCTGGATGGGAGTGCTGGAGAAAGAGGGAGACGGCGGGCGGCGCGCCTTTTATACCCACGCCCGAAAGATCCGATCGATA
CTGACAAAACGGGATGAACACATCGGCGGCGGCCTGGACTGCGCGCCATCTGCAAATGCCCAGCCAGTCCCGTCGGGCGCCACCACCA
GCCCTGGTCGAGTCCCCCTCGAGGGCGACGCTCTATTCTATCCATGCGCGCAATTGCAGGTGCGCGGTCGAAGAACAGTCCTTCGCAGT
CCTTCTCGCACCTGGGCTGCGACCCTGTCTACCTCTCATCCTAACCCCTCCGCGGCTTCGCAGTACAGTTACTAATCTCACACCGAAGAG
GCTCTCGCGCCACCCTCCGATCCCGAGCACGTTCCTTACATGCCACAGCGTCAGAATTGAACACAATGCACGTCARATCAGATCCCCGG
GAATTCGTAATCATGGTCATAGCTGTTTCCTGTGTGAAATTGTTATCCGCTCACAATTCCACACAACATACGAGCCGGAAGCATAAAGTG
TAAAGCCTGGGGTGCCTAATGAGTGAGCTAACTCACATTAATTGCGTTGCGCTCACTGCCCGCTTTCCAGTCGGGAAACCTGTCGTGCCA
GCTGCATTAATGAATCGGCCAACGCGCGGGAGAGGCGGTTTGCGTATTGGGCGCTCTTCCGCTTCCTCGCTCACTGACTCGCTGCGCTC
GGTCGTTCGGCTGCGGCGAGCGGTATCAGCTCACTCAAAGGCGGTAATACGGTTATCCACAGAATCAGGGGATAACGCAGGAAAGAAC
ATGTGAGCAAAAGGCCAGCAAAAGGCCAGGAACCGTAAAAAGGCCGCGTTGCTGGCGTTTTTCCATAGGCTCCGCCCCCCTGACGAGC
ATCACAAAAATCGACGCTCAAGTCAGAGGTGGCGAAACCCGACAGGACTATAAAGATACCAGGCGTTTCCCCCTGGAAGCTCCCTCGTG
CGCTCTCCTGTTCCGACCCTGCCGCTTACCGGATACCTGTCCGCCTTTCTCCCTTCGGGAAGCGTGGCGCTTTCTCATAGCTCACGCTGTA
GGTATCTCAGTTCGGTGTAGGTCGTTCGCTCCAAGCTGGGCTGTGTGCACGAACCCCCCGTTCAGCCCGACCGCTGCGCCTTATCCGGTA
ACTATCGTCTTGAGTCCAACCCGGTAAGACACGACTTATCGCCACTGGCAGCAGCCACTGGTAACAGGATTAGCAGAGCGAGGTATGTA
GGCGGTGCTACAGAGTTCTTGAAGTGGTGGCCTAACTACGGCTACACTAGAAGGACAGTATTTGGTATCTGCGCTCTGCTGAAGCCAGTT
ACCTTCGGAAAAAGAGTTGGTAGCTCTTGATCCGGCAAACAAACCACCGCTGGTAGCGGTGGTTTTTTTGTTTGCAAGCAGCAGATTACG
CGCAGAAAAAAAGGATCTCAAGAAGATCCTTTGATCTTTTCTACGGGGTCTGACGCTCAGTGGAACGAAAACTCACGTTAAGGGATTTT
GGTCATGAGATTATCAAAAAGGATCTTCACCTAGATCCTTTTAAATTAAAAATGAAGTTTTAAATCAATCTAAAGTATATATGAGTAAAC
TTGGTCTGACAGTTACCAATGCTTAATCAGTGAGGCACCTATCTCAGCGATCTGTCTATTTCGTTCATCCATAGTTGCCTGACTCCCCGTC
GTGTAGATAACTACGATACGGGAGGGCTTACCATCTGGCCCCAGTGCTGCAATGATACCGCGAGACCCACGCTCACCGGCTCCAGATTT
ATCAGCAATAAACCAGCCAGCCGGAAGGGCCGAGCGCAGAAGTGGTCCTGCAACTTTATCCGCCTCCATCCAGTCTATTAATTGTTGCC
.GGGAAGCTAGAGTAAGTAGTTCGCCAGTTAATAGTTTGCGCAACGTTGTTGCCATTGCTACAGGCATCGTGGTGTCACGCTCGTCGTTTG
GTATGGCTTCATTCAGCTCCGGTTCCCAACGATCAAGGCGAGTTACATGATCCCCCATGTTGTGCAAAAAAGCGGTTAGCTCCTTCGGTC
CTCCGATCGTTGTCAGAAGTAAGTTGGCCGCAGTGTTATCACTCATGGTTATGGCAGCACTGCATAATTCTCTTACTGTCATGCCATCCGT
AAGATGCTTTTCTGTGACTGGTGAGTACTCAACCAAGTCATTCTGAGAATAGTGTATGCGGCGACCGAGTTGCTCTTGCCCGGCGTCAAT
ACGGGATAATACCGCGCCACATAGCAGAACTTTAAAAGTGCTCATCATTGGAAAACGTTCTTCGGGGCGAAAACTCTCAAGGATCTTAC
CGCTGTTGAGATCCAGTTCGATGTAACCCACTCGTGCACCCAACTGATCTTCAGCATCTTTTACTTTCACCAGCGTTTCTGGGTGAGCAA
AAACAGGAAGGCAAAATGCCGCAAAAAAGGGAATAAGGGCGACACGGAAATGTTGAATACTCATACTCTTCCTTTTTCAATATTATTGA
AGCATTTATCAGGGTTATTGTCTCATGAGCGGATACATATTTGAATGTATTTAGAAAAATAAACAAATAGGGGTTCCGCGCACATTTCCC
CGAAAAGTGCCACCTGACGTCTAAGAAACCATTATTATCATGACATTAACCTATAAAAATAGGCGTATCACGAGGCCCTTTCGTCTCGC
GCGTTTCGGTGATGACGGTGAAAACCTCTGACACATGCAGCTCCCGGAGACGGTCACAGCTTGTCTGTAAGCGGATGCCGGGAGCAGAC
AAGCCCGTCAGGGCGCGTCAGCGGGTGTTGGCGGGTGTCGGGGCTGGCTTAACTATGCGGCATCAGAGCAGATTGTACTGAGAGTGCAC
CATATGCGGTGTGAAATACCGCACAGATGCGTAAGGAGAAAATACCGCATCAGGCGCCATTCGCCATTCAGGCTGCGCAACTGTTGGGA
AGGGCGATCGGTGCGGGCCTCTTCGCTATTACGCCAGCTGGCGAAAGGGGGATGTGCTGCAAGGCGATTAAGTTGGGTAACGCCAGGGT
TTTCCCAGTCACGACGTTGTAAAACGACGGCCAGTGCCA
```

Figure 8 : Nucleotide sequence of the vector pESC, containing the sc3 gene promoter (1-1033), a phleomycin resistance marker (1540-2855) and the sc3 gene terminater (1104-1540).

```
CATGGGATATCGCATGCCTGCAGAGCTCTAGAGTCGACGGGCCCGGTACCGCGGCCGCCTTAAGACGCGTGGATCCGCAGGTGAACGCGC
CTATCGGTGGGATATTCGGGCGACGGGAGCCTCGGCAATCTGAGCCTCGTTACTGCCTAGCAAATTCGGAATCCCTTCGATGTCATAGGGT
CGCGGACAAGTGATCGTCTTGCTACATACTCCAAGGTGTTGACTCATTCCCTCGATAATGAACATTGTTGTTGTTTGTTCTCTATCCGC
TCAGTCACGCGACCCCACACGTGCATGGTTGAACTTCGCCACGCAACAACCGCATGACGACATGGCGAACCTAAGTAAAGGCTGAGTCGT
GGACTAAAGCACTCCACTTTACGGCGAGGATGCCAGTCTACGTCATGAATGAAGCCTCAGGTCCCGAAGTAAGGGGGTACAAAAGGAGG
GTGAAAGGTGGACGTTTTCTTACCATCCTTCCACCTCCCAGACCACCATGCCGGGAATTCCCAGCTTGCTCAAAAAGGTTCTGCCCGTACG
CCCGCGAAATTCCTTCGAGGTGGCCCCTATCGCATACATGCACGACTTCAAAACATCCATTCTATCATTTTGGGATCGTACAATTATTAGA
CATGTTGTACAACGTTACATTCCTTTCTTCTTTTACTCTCCGGCCCAGTCTATGTAGAGGTAAAGTACAAGCGTCCAAAGGATCAGGCACTT
AGAGCGCGCCGTCTTGCTTCGCCGCTTAGAGCGCGCCGTCCTGCTTCGCCGCGTAGACGAGCAGGTCGCAGACACGGCGGGAGTAGCCCC
ACTCGTTGTCGTACCAGGCAATGAGCTTCACGAAGCTCTTGCTGATCGCGATGCCGGGGATCGATCCACGCGTCTTAAGGCGGCCGCGGT
ACCCCCTCGGACCCGTCGGGCCGCGTCGGACCGGCGGTGTTGGTCGGCGTGGTCAGTCCTGCTCCTCGGCCACGAAGTGCACGCAGTTG
CCGGCCGGGTCGCGCAGGGCGAACTCCCGCCCCCACGGCTGCTCGCCGATCTCGGTCATGGCCGGCCCGGAGGCGTCCCGGAAGTTCGTG
GACACGACCTCCGACCACTCGGCGTACAGCTCGTCCAGGCCGCGCACCCACACCCAGGCCAGGGTGTTGTCCGGCACCACCTGGTCCTGG
ACCGCGCTGATGAACAGGGTCACGTCGTCCCGGACCACACCGGCGAAGTCGTCCTCCACGAAGTCCCGGGAGAACCCGAGCCGGTCGGTC
CAGAACTCGACCGCTCCGGCGACGTCGCGCGCGGTGAGCACCGGAACGGCACTGGTCAACTTGGCCATGCATGGTGATGGGCATTATGTG
TGATGGGATGCGATGGGAGAGGGAAGTGCTCTGGATGGGAGTGCTGGAGAAAGAGGGAGACGGCGGGCGGCGCGCCTTTTATACCCACG
CCCGAAAGATCCGATCGATACTGACAAAACGGGATGAACACATCGGCGGCGGCCTGGACTGCGCGCCATCTGCAAATGCCCAGCCAGTC
CCGTCGGGCGCCACCACCAGCCCTGGTCGAGTCCCCCTCGAGGGCGACGCTCTATTCTATCCATGCGCGCAATTGCAGGTGCGCGGTCGA
AGAACAGTCCTTCGCAGTCCTTCTCGCACCTGGGCTGCGACCCTGTCTACCTCTCATCCTAACCCCTCCGCGGCTTCGCAGTACAGTTACTA
ATCTCACACCGAAGAGGCTCTCGCGCCACCCTCCGATCCCGAGCACGTTCCTTACATGCCACAGCGTCAGAATTGAACACAATGCACGTC
ARATCAGATCCCCGGGAATTCGTAATCATGGTCATAGCTGTTTCCTGTGTGAAATTGTTATCCGCTCACAATTCCACACAACATACGAGCC
GGAAGCATAAAGTGTAAAGCCTGGGGTGCCTAATGAGTGAGCTAACTCACATTAATTGCGTTGCGCTCACTGCCCGCTTTCCAGTCGGGA
AACCTGTCGTGCCAGCTGCATTAATGAATCGGCCAACGCGCGGGGAGAGGCGGTTTGCGTATTGGGCGCTCTTCCGCTTCCTCGCTCACTG
ACTCGCTGCGCTCGGTCGTTCGGCTGCGGCGAGCGGTATCAGCTCACTCAAAGGCGGTAATACGGTTATCCACAGAATCAGGGGATAACG
CAGGAAAGAACATGTGAGCAAAAGGCCAGCAAAAGGCCAGGAACCGTAAAAAGGCCGCGTTGCTGGCGTTTTTCCATAGGCTCCGCCCC
CCTGACGAGCATCACAAAAATCGACGCTCAAGTCAGAGGTGGCGAAACCCGACAGGACTATAAAGATACCAGGCGTTTCCCCCTGGAAG
CTCCCTCGTGCGCTCTCCTGTTCCGACCCTGCCGCTTACCGGATACCTGTCCGCCTTTCTCCCTTCGGGAAGCGTGGCGCTTTCTCATAGCT
CACGCTGTAGGTATCTCAGTTCGGTGTAGGTCGTTCGCTCCAAGCTGGGCTGTGTGCACGAACCCCCCGTTCAGCCCGACCGCTGCGCCTT
ATCCGGTAACTATCGTCTTGAGTCCAACCCGGTAAGCACGACTTATCGCCACTGGCAGCAGCCACTGGTAACAGGATTAGCAGAGCGAG
GTATGTAGGCGGTGCTACAGAGTTCTTGAAGTGGTGGCCTAACTACGGCTACACTAGAAGGACAGTATTTGGTATCTGCGCTCTGCTGAAG
CCAGTTACCTTCGGAAAAAGAGTTGGTAGCTCTTGATCCGGCAAACAAACCACCGCTGGTAGCGGTGGTTTTTTGTTTGCAAGCAGCAGA
TTACGCGCAGAAAAAAAGGATCTCAAGAAGATCCTTTGATCTTTTCTACGGGGTCTGACGCTCAGTGGAACGAAAACTCACGTTAAGGGA
TTTTGGTCATGAGATTATCAAAAAGGATCTTCACCTAGATCCTTTTAAATTAAAAATGAAGTTTTAAATCAATCTAAAGTATATATGAGTA
AACTTGGTCTGACAGTTACCAATGCTTAATCAGTGAGGCACCTATCTCAGCGATCTGTCTATTTCGTTCATCCATAGTTGCCTGACTCCCG
TCGTGTAGATAACTACGATACGGGAGGGCTTACCATCTGGCCCCAGTGCTGCAATGATACCGCGAGACCCACGCTCACCGGCTCCAGATT
TATCAGCAATAAACCAGCCAGCCGGAAGGGCCGAGCGCAGAAGTGGTCCTGCAACTTTATCCGCCTCCATCCAGTCTATTAATTGTTGCC
GGGAAGCTAGAGTAAGTAGTTCGCCAGTTAATAGTTTGCGCAACGTTGTTGCCATTGCTACAGGCATCGTGGTGTCACGCTCGTCGTTTGG
TATGGCTTCATTCAGCTCCGGTTCCCAACGATCAAGGCGAGTTACATGATCCCCCATGTTGTGCAAAAAAGCGGTTAGCTCCTTCGGTCCT
CCGATCGTTGTCAGAAGTAAGTTGGCCGCAGTGTTATCACTCATGGTTATGGCAGCACTGCATAATTCTCTTACTGTCATGCCATCCGTAA
GATGCTTTTCTGTGACTGGTGAGTACTCAACCAAGTCATTCTGAGAATAGTGTATGCGGCGACCGAGTTGCTCTTGCCCGGCGTCAATACG
GGATAATACCGCGCCACATAGCAGAACTTTAAAAGTGCTCATCATTGGAAAACGTTCTTCGGGGCGAAAACTCTCAAGGATCTTACCGCT
GTTGAGATCCAGTTCGATGTAACCCACTCGTGCACCCAACTGATCTTCAGCATCTTTTACTTTCACCAGCGTTTCTGGGTGAGCAAAAACA
GGAAGGCAAAATGCCGCAAAAAAGGGAATAAGGGCGACACGGAAATGTTGAATACTCATACTCTTCCTTTTTCAATATTATTGAAGCATT
TATCAGGGTTATTGTCTCATGAGCGGATACATATTTGAATGTATTTAGAAAAATAAACAAATAGGGGTTCCGCGCACATTTCCCCGAAAAG
TGCCACCTGACGTCTAAGAAACCATTATTATCATGACATTAACCTATAAAAATAGGCGTATCACGAGGCCCTTTCGTCTCGCGCGTTTCGG
TGATGACGGTGAAAACCTCTGACACATGCAGCTCCCGGAGACGGTCACAGCTTGTCTGTAAGCGGATGCCGGGAGCAGACAAGCCCGTCA
GGGCGCGTCAGCGGGTGTTGGCGGGTGTCGGGGCTGGCTTAACTATGCGGCATCAGAGCAGATTGTACTGAGAGTGCACCATATGCGGTG
TGAAATACCGCACAGATGCGTAAGGAGAAAATACCGCATCAGGCGCCATTCGCCATTCAGGCTGCGCAACTGTTGGGAAGGGCGATCGGT
GCGGGCCTCTTCGCTATTACGCCAGCTGGCGAAAGGGGGATGTGCTGCAAGGCGATTAAGTTGGGTAACGCCAGGGTTTTCCCAGTCACG
ACGTTGTAAAACGACGGCCAGTGCCAAGCTTAGATCTCCGAACCAGAAATGCGATTGCGTTCAGGCCCAATTAAGAATAAAGCTGCGTCA
GGGCAGCGACGTATCTTGATCCATCATTGACTCACCGGCATCGGCGTCAACACCAAAGCAAGCTCGTCCCACCCATAGGCGTGCACCGGC
CGGCGTGCGCCATTGAGGTACATGAGCGGGGCGAAAGTCCGCCATTGGTAGCCCTGTCGTGGACGCGCGGCGATGAAACGTTTCCCACCA
TTGGGAAGAAACGTCTGCGGCCCATCATCCCTTCACCGGATGACAAGGCGGCGTCGCGCCTTTGCCGCAGAGGCCGGCGGGCGACATGCA
```

Figure 9 : Nucleotide sequence of the vector pELP, containing the laccase gene (promoter 4457-6983), a phleomycin resistance marker (507-1822) and the sc3 gene terminater (71-507) (continuation of the sequence on the following page).

```
CAGCGAAGGTCCGTTGCGGATGGGAAGCAGGCAATCAGTGGGTGTCCTACGCCGCCACGATGGTCGGGGAGCGTAGGCGCCCTCCCA
TAAGGCGGCAAGCATCATGATGCTCTCCGATTCGGGAAGCCTGGTGCGATGCTGGAGAGACTCTCTCCGAGAGACCAGTGTGCGCAAC
GTTCCTGGCCTGGAAGACTTTAAAGTGAGTGTAGAAGGGCGAGCAGAGGACGATCATCGGATTGCAGGAACCATCGGCATCCTCAGC
CTGGGAAGGATGGCTCTTGGTAGACATTCGCGGAAGGTGTCCTAGATGTGAGCGGGCTTCTTGGATGATCATGTCGTAACTTTTTCTGA
CCTCGTCGGTGGTACGCATGGCAGGATTGAGCATTACGGTATGCCTCCCATTCATAAACGATAACCCCTTCCTTCAGGTTGGTCATCTC
CATAGAGCGGCACGCTCTCAAGGCCTAGGCTATTCACACCTCCTTCGCAACATCCCTATTCACGGTGTCTGTAAGGAACGACTTGTCAT
GGGATCACATGAAGTGCAGCATACTGTTCGCCGGTCTCGCAGTACAGACGCTAGTACGGGAAGTCGACATCCAAGCGTTCAGTCACCA
CATGGCAAAAAAGCTGCACCATACTCTTTATGGTGAGTTGTTCGTGAGTGGTATACAGTCATTCATGAGGGAATGCCCACCGGATAGG
GTGTGGCGGCCGCAATATTCATCGCCTGGCAATAGTCGATGTGCGTCCTTGTTCAATGAATATCATGGGTCACATGTGGAGACGGTTAA
ACAGCGTTGACTGTGAATCCCTGGTGTGTGTTGGGCCGAACAGGTACGTTGCAGGAACACCAATATCTCTTCGGCAGCCCAGTTCTTTG
CGAGCGGCACAGGCAGGCATCGCGCAACAGATCCCAGCCATCCGGCCTCTGACATTCGGGATACCTGAAGCCCTTCAGGTACGGAGC
GAAGAGGTGGGCTCTCTGCAGCGATTGGCGGACGGATAGCTGTATTTCCTCTCTCACCATTGGGAAGATGTGAAAGGCTCCATCATAT
AGCGGCTCAACTCTACCTCGAATGTCCAAACACGGCGGGAATACTTATTTATGTGGACAAGGCCGAGCTATGATAGCTTGCTCCCGAA
GTTGGTAAGTCCCGCAATCTGCGGTTCAGGCAACAGTCTCGGAAAAATAAGAAGAATATTGTAGGTGCGTGTAGGCGTATCGCCCAAA
TGCGCACACACGGAGGCTTTAGGAGATGAAGCGCCCGTGAGCGGTAAGGGAGTTGGTTCACCGCCGCCCCGACCGACTCTCTCTCTTT
CCCAGCATCATGTCTCGGCGCAAACTTTACCCTCTATTGACCAACTCCACGAGAAAGCAGGAACAGCTTCCTTGTCTCTCATGACGTCC
GCAATCCAGACCCTTAGCCGGTTCGTTACTCATCGTTATCCCTGCCGCCATCGTAGTGGAGTCAGCCTGGCCAGTGCGTAGTCCCGTCT
CTCTTGCTGCACTAGAGAAGCCCCATGAGACAGCGTTTTTTGCTTTATTTCTGCTGTTTCTATAGACACCATAGGGGCAAACGATCCTG
CACGCCCAGAGGTATTGGGCTCGTCAGATTCCCAGTTTTTCTCCTCGGTCTGAATCGGCTGCACGGCAGATAAATCGGCCGGAAATGCT
ATAGCCCTTCATAGCCCGCTATGAGAGTCGCAAAAGGCTTGTCAGTCAGGTCGGTCGAGTGGCTCTCACGAAGAGCGTCAACTTCGCG
CGACAGCCGCCTTTCAGGGCAAGATAGATCCTCCCATCATCCCCTACTGCGCTCAGCGCCGGTACCGAACAATTGACTTACCGACATC
CTCCGGGACGCGCAAATGCTGTTCGACGGAACGTAATCCTCTTCGTCCCGCCTCTTTTCGCTCTCACGCATTCCGTGTGGTTCGCGCGA
CGGCCGCTCATCAGGACCAGACCAGTCTCAATGTCTGGTACCGGCACAATGGTGACACTGCGGCAACTGAGTAGGTCTGGTCACTCTG
GTGCACCGTCGCTTACGCTGACCTTCGGGATACTGTCCTGCAGACATCTGGAGCGCCTGTCTTTCCCCTAGTATAAATGATGTCTGTCC
GCAGGTCCTTGAAGACCGCTCGAGTCCCACTTGAGTTTTAGGTAGGACCTGTTCCTCCACAACCCCTCTTTC
```

Figure 9 Cont'd: Nucleotide sequence of the vector pELP (continuation), containing the laccase gene (promoter4457-6983), a phleomycin resistance marker (507-1822) and the sc3 gene ternminator (71-507).

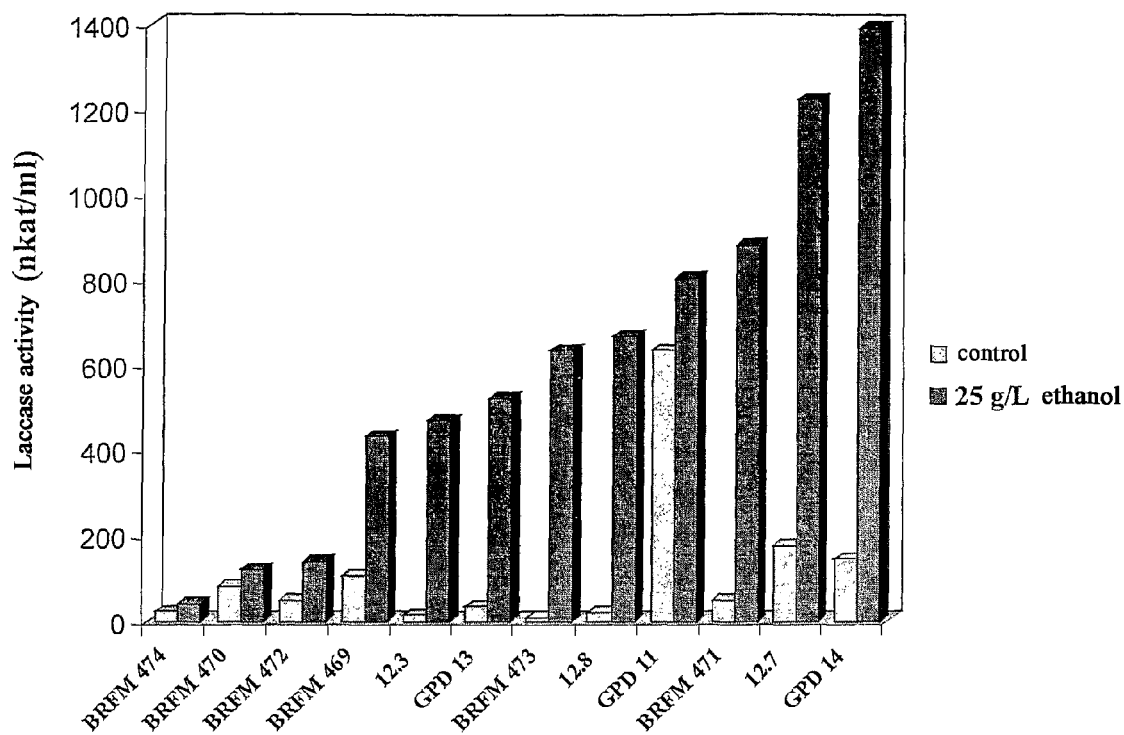
Figure 10 : Results of production of the transformants having the most significant activities. The culture was carried out with or without (control) ethanol.

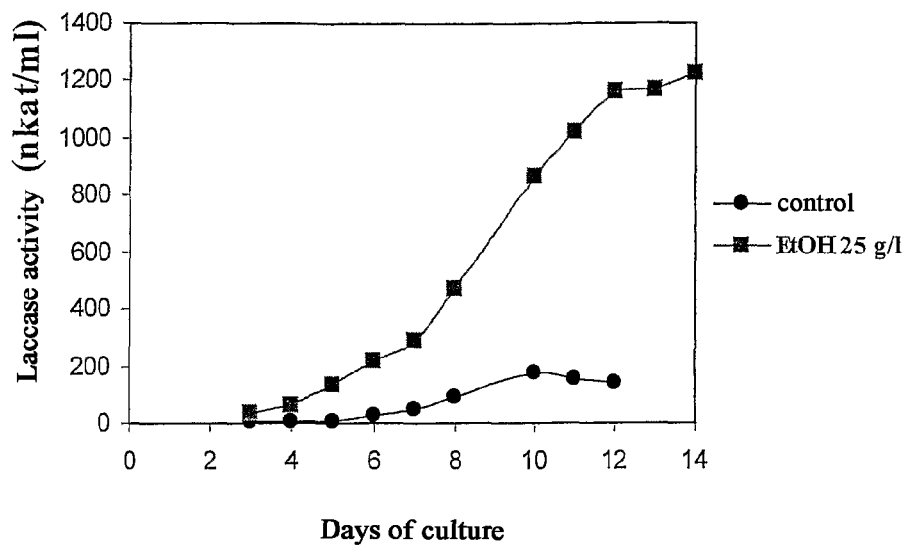
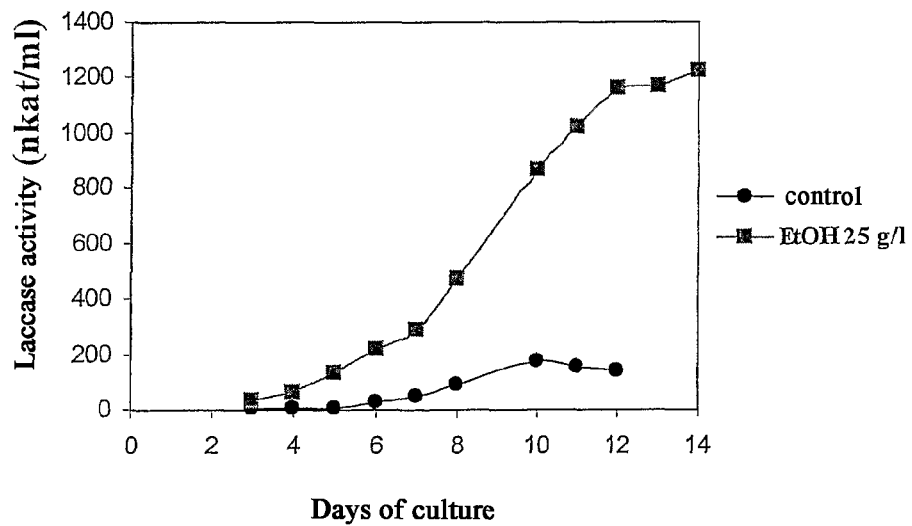
Figure 11 : Monitoring of the laccase activities of the transformants GPD 14 and 12.7 as a function of time with or (control) without ethanol

```
TGGGGAGATGGTTCTATATATCAAAATGATCTTCTGTCCTGAGCTTTCCTCGTCCTTGTTTTCGTCTTGTCAGTGCCGCGACATGCTTTTATTAAACCAT    100
TGGCGAGCTGCCCGCGCCCAAGGAGATAGCATAATCGCCTGAGAAACCTAGTCGTCTCATGGCCGTGTAACCGTTCTTGCGACTTATTTTCGCACTTCTC    200
TCAGAATATAAAGGCCTATTGTGATACGGTTCATCTAACCCCAGCGTCCCCTCCGAAAGATGGGCTGCCTCTCACTCTTCGCATTCCTTACTGCTTTAAA    300
                                                                       M  G  C  L  S  L  F  A  F  L  T  A  L  N       14
CTCAGTTCATGCCGCTGTGGGTCCCGTTACGGACTTAACACTGATCGTAGATACTGTCGCCCCCGACGGTGCTGCTTTCGCGCGGGAAGGTGAGACTTTG    400
  S  V  H  A  A  V  G  P  V  T  D  L  T  L  I  V  D  T  V  A  P  D  G  A  A  F  A  R  E                                43
CGACTGTAAATGCGGATTTGAGTTTCTAATTATAATCTTCCAGCCATTGTCGTCCAAGAGGAACCAAACTCCGTCATTGGTCCGGTCATCGTAGGTGGG    500
                          A  I  V  V  Q  E  E  P  N  S  V  I  G  P  V  I  V                                            60
TAGCTACGAGTCTTCCTCCTTCATTTAGCTCATCACCAAGTGATATGATATTAATTAAGGTCAAAAGGGGGACAACTTTCGGCTCAATGTTATCAACAAT    600
                                                                G  Q  K  G  D  N  F  R  L  N  V  I  N  N              74
TTGGATTCTCCGAACATGCGCCAATCTACTTCCATTCATTGGCATGGCATCTTCCAAGGAAACGGTACGTGGTATATCGGATAATCTATCTGTATCCATT    700
  L  D  S  P  N  M  R  Q  S  T  S  I  H  W  H  G  I  F  Q  G  N                                                      95
GACTCGAATATAGGTCAGAATTGGGCTGGTGCGTTGGCCTTCCTGAAGCCTGCTCGAATTTATCTTCCTGAATTTTTAGATGGCGCCGCATTCGTTAACC    800
                      G  Q  N  W  A                               D  G  A  A  F  V  N                                107
AGGTAAGGAGATGTTCCTGCCTTCGTTTCCCCAGAACTAATTATCCTAGTGCCCCATTGCCCCCGGAGGGGACTCGTTCTTGTACGACTTTACCGAACCT    900
Q                                                        C  P  I  A  P  G  G  D  S  F  L  Y  D  F  T  E  P            125
TTCCAGACTGGCACATTTTGGTATCATTCCCATTTATCAACTCAATACTGCGATGGACTGAGGGGAGCATTCGTCGTTCGTTCTCTTCTTCATCAAGTCA   1000
  F  Q  T  G  T  F  W  Y  H  S  H  L  S  T  Q  Y  C  D  G  L  R  G  A  F  V                                         150
CCGCTTTCTTCTCACTTATCTAGATCTACGATCCGCTCGACCCTTACCGGTTGCTCTACGATGTCGACGACGAGTCGACTGTGATTACTCTGGCGGACTG   1100
                    I  Y  D  P  L  D  P  Y  R  L  L  Y  D  V  D  D  E  S  T  V  I  T  L  A  D  W                     176
GTACCACAGCTATGCGGAGGACATTCTAATCGCGTAGGAGATTTTCCCAAGATGTCTCCTCTGCCTCTCTGAAATCCATGAACTAGTGCAGGCGACACTA   1200
  Y  H  S  Y  A  E  D  I  L  I  A                                                          A  G  D  T               191
TCCTCATCAATGGTCACGGAAGATTCGCCGGAGCCGGCGGAACGGCAACAGAACTATCTGTCATTACTGTTGAGCATGGAAAGCGGTAGGCATTCTCCCT   1300
  I  L  I  N  G  H  G  R  F  A  G  A  G  G  T  A  T  E  L  S  V  I  T  V  E  H  G  K  R                             220
CGGCTTTGTAGATGTGTCTAATTTGTGATAGCTACCGATTGCGATTTGCCAATATCGCTTGTGACCCTTGGTTTGCCGTGAAAATCGATAGCCATACGAA   1400
                          Y  R  L  R  F  A  N  I  A  C  D  P  W  F  A  V  K  I  D  S  H  T  N                        243
CCTTCGCGTTATCGAAGCTGACGGTATTACTACTGTGCCTGTCACGGTGGACTCCTTCAATGTAGGCTTACCCTTAGCACTTTCCCACTCTGGATCCTCT   1500
  L  R  V  I  E  A  D  G  I  T  T                                                                                    254
TATGACTTCCCAAGATCTTTGTGGGCCAACGATATAGTGTCATCCTCCATGCCAACCAGCCTGTTGGAAAACTACTGTAAGCTGCCTAAATGTTGCATGAC   1600
        I  F  V  G  Q  R  Y  S  V  I  L  H  A  N  Q  P  V  G  N  Y                                                   274
TGTCCATGATTCTAACCCCGCCAGGGATTCGGGCCGCTCCGAACGGCGTGAGCAATTTCGGGGTGGGATCGACTCGGCTATTCTCCGTTATGTTGGCGC   1700
                    W  I  R  A  A  P  N  G  V  S  N  F  A  G  G  I  D  S  A  I  L  R  Y  V  G  A                    300
CCCAGAAGAAGAGCCCAACACTAGTGAGGATACTCCATCCGACACACTTCAAGAGCAGGATCTTCACCCGCTGATCCTACCCGGCGCGCCAGGCATCCAC   1800
  P  E  E  E  P  N  T  S  E  D  T  P  S  D  T  L  Q  E  Q  D  L  H  P  L  I  L  P  G  A  P  G  I  H                333
TCCCGTGGGGCCGCCGACGTTGTCCACACCGTATCAATGGAGTTTGTGAGTGTGGCGACTTTCTGGCCCCCTTTATTAATATAATCTGGTTAGGATGGC   1900
  S  R  G  A  A  D  V  V  H  T  V  S  M  E  F                                                                       348
GCAAACTTCCAATTCCTCCTGGATGGCGTGGCCTTCCAGCCGTGCGTCATCTCTTTCAAAGAATTTATCTAGCTGACGATTTTGAAATGTAGCCCGACCA   2000
                                                                          L  T  I  L  K  C  S  P  T                  357
TGCCCGTCCTTCTGCAAATATTATCGGGAGCGCAGACTGCTAATACCCTTCTCCCGGCGGGATCCTTTATCCAAGCGTCGCACAATGACATCGTGGAGCT   2100
  M  P  V  L  L  Q  I  L  S  G  A  Q  T  A  N  T  L  L  P  A  G  S  F  I  Q  A  S  H  N  D  I  V  E  L              391
CAATTTCCCAGCTGTCAACGTAGCCGCTGTCGGTGGACCGTGCGTCCCATCTTTCCTTGCCAGCTTGAAATTTACGCTCTTTTAGACATCCAATCCATCT   2200
  N  F  P  A  V  N  V  A  A  V  G  G  P                                       H  P  I  H  L                          409
GTGAGCGCAGCGGGACCTTTGGCTTATGGCATATGACTTATTATTAGCCATGGCCATGCATTCGACGTTATACGCTCTGCTGGAACGAACTCCGATAACT   2300
                                                    H  G  H  A  F  D  V  I  R  S  A  G  T  N  S  D  N                426
GGTTCAATCCGGTATTTTCATTCGACTTCCATAAGATGACGATGGCTCACTATGGTTTTTACCCAGCCTCGCAGAGATGTCGTATCCACCGGTACCGATC   2400
  W  F  N  P                                        P  R  R  D  V  V  S  T  G  T  D                                 441
CTAATGACAATGTGTACGTGTTTCGCTATTGATTGTCCGTTTTGATTTGACTGTTGGACAGCACCATTCGCTTCCGGGCCGACAACCCGTACGTAAACTG   2500
  P  N  D  N  V                                T  I  R  F  R  A  D  N  P                                            455
CTGAATCTCTCGTTGTCTTTGGTTCTCATAATCTCATCAGAGGTCCATGGTTCCTTCACTGCCACATTGACTGGCACCTTGAACTCGGCTTTGCTTTGGT   2600
                                                  G  P  W  F  L  H  C  I  D  W  H  L  E  L  G  F  A  L  V            475
GATTGCAGAAGCGCCTAGCGAATGGGACAGCGACATTAACCCTCCTGGTGCGCTGCCTGTGAACCTTTTCTCCCTACACTTGCTAAGATCGCTCTAGCTG   2700
  I  A  E  A  P  S  E  W  D  S  D  I  N  P  P                                                          A            491
CGTGGGATGACCTATGCCCTACGTTCGCTTGGCTCTTCTCTTTTACTATTTCAAGTTTCCTCACATTCTCAACTTCACAGATATGATGCCCTGCCGCCTGAG   2800
  A  W  D  D  L  C  P  T  F  A  W  L  L  F  Y  Y  F  K  F  P  H  I  L  N  F  T  D  M  M  P  C  R  L  S             525
CAGCAGTAATCGAGTTAAGAACCTCAACGTTGACTAAGGAAAAAGCAAAGCAGAATATGAAACTTCTCATTTATCTTTATATCGACACATTCACTATTCAA   2900
  S  S  N  R  V  K  N  L  N  V  D                                                                                    536
CCTACGGATTTTCCCTCGCACCTGAATTTCGGTGCTAGATCCCCATCCTTGGTGGAGTAGGAAAGAAATTTCTTGTATAAAACCCATGGGTTCTTCTACC   3000
AATATATACATAACGGTCCGTGGGGTTAGTTAATTCGT                                                                             3037
```

Gene of the laccase of *Halocyphina villosa*

Figure 12

METHOD FOR OVERPRODUCING SPECIFIC RECOMBINANT PROTEIN WITH *P. CINNABARINUS* MONOKARYOTIC STRAINS

BACKGROUND OF THE INVENTION

1. Field of the Invention

The present invention relates to the use of monokaryotic strains of filamentous fungi of the species *Pycnoporus* of the basidiomycete group, for the implementation of a method for preparing a specific recombinant protein, said method being carried out by overexpression of the gene encoding for this protein in the abovementioned monokaryotic strain of *Pycnoporus*.

2. Description of Related Art

At present, two fungal models are preferentially used by the large industrial groups within the framework of the production of enzymes involved in plant biotransformations, such as the metalloenzymes. These are *Aspergillus*, and *Trichoderma*, which belong to the deuteromycete group. However, production yields using these models, in particular in the production of laccases, do not exceed 150 mg/l.

BRIEF SUMMARY OF THE INVENTION

The present invention results from the demonstration by the Inventors of the fact that the transformation of monokaryotic strains of *P. cinnabarinus* deficient in laccase activity using vectors containing the gene encoding for this laccase and the expression of which is under the control of a promoter identical to the endogenous pLac promoter of the laccase of *P. cinnabarinus*, leads to an equivalent production of laccase as during the implementation of a method for overproducing laccase by induction of the endogenous promoter of this laccase by the action of ethanol on monokaryotic strains of *P. cinnabarinus* not deficient in laccase activity, and which equals one g/l.

Similar results have been obtained by the Inventors by using the gpd promoter, and the sc3 promoter of *Schizophyllum commune*, instead of the abovementioned pLac promoter.

BRIEF DESCRIPTION OF THE DRAWINGS

FIG. 1: Isolation of monokaryotic strain deficient in laccase activity.

FIG. 2: Isolation of the gene encoding for the laccase of *Pycnoporus cinnabarinus* laccase.

FIG. 3: Southern blot study of the gene encoding for the laccase of *Pycnoporus cinnabarinus*.

FIG. 4: Sequence of the gene encoding for the laccase of *Pycnoporus cinnabarinus* represented by SEQ ID NO: 1.

FIG. 5: Sequence of the pLac promoter sequence of the gene encoding for the laccase of *Pycnoporus cinnabarinus* (up to the ATG encoding for the methionine of the laccase), the pLac promoter being represented by SEQ ID NO: 3.

FIG. 6: Restriction map of the three expression vectors pEGT, pESC, pELP, used for the production of laccase in *Pycnoporus cinnabarinus*.

FIG. 7: Nucleotide sequence of the vector pEGT represented by SEQ ID NO: 12, containing the gpd gene promoter (4480-5112), a phleomycin resistance marker (507-1822) and the sc3 gene terminator (71-507).

FIG. 8: Nucleotide sequence of the vector pESC represented by SEQ ID NO: 13, containing the sc3 gene promoter (1-1033), a phleomycin resistance marker (1540-2855) and the sc3 gene terminator (1104-1540).

FIG. 9: Nucleotide sequence of the vector pELP represented by SEQ ID NO: 14, containing the laccase gene (promoter 4457-6983), a phleomycin resistance marker (507-1822) and the sc3 gene terminator (71-507)

FIG. 10: Results of production of the transformants having the most significant activities. The culture was carried out with or without (control) ethanol.

FIG. 11: Monitoring of the laccase activities of the transformants GPD 14 and 12.7 as a function of time with or (control) without ethanol.

FIG. 12: Sequence of the gene encoding for the laccase of *halocyphina villosa* represented by SEQ ID NO: 18.

DETAILED DESCRIPTION OF THE INVENTION

A subject of the present invention is a method for preparing a specific recombinant protein, said method being carried out by overexpression of the gene encoding for this specific protein in a monokaryotic strain of filamentous fungi of the species *Pycnoporus* of the basidiomycete group, and comprises:

- a stage of culturing the abovementioned monokaryotic strain of *Pycnoporus*, said strain being transformed using an expression vector containing the gene encoding for the specific recombinant protein, the expression of which is placed under the control of a promoter corresponding to an endogenous promoter of the abovementioned fungi, or of a different promoter (also designated exogenous promoter), said promoter being constitutive or inducible,
- if appropriate a stage of induction of the abovementioned promoter, when the latter is inducible,
- the recovery, and, if appropriate, the purification of the specific recombinant protein, produced in the culture medium.

A more particular subject of the invention is a method as described above, characterized in that the monokaryotic strain of *Pycnoporus* used for the overexpression of the gene encoding for the specific recombinant protein, is as obtained by culturing the original dikaryotic strain at 30° C. in the dark for 15 days, followed by a stage of exposure to daylight for 2 to 3 weeks at ambient temperature until the formation of fruiting organs corresponding to differentiated hyphas called basidia, within which karyogamy (fusion of nuclei) then takes place, followed by meiosis which leads to the formation of four sexual spores, or genetically different haploid basidiospores, which, after germination, produces a monokaryotic mycelium.

Advantageously, the monokaryotic strain of *Pycnoporus* used in the abovementioned method of the invention, is a strain of *Pycnoporus cinnabarinus*.

The specific recombinant proteins overexpressed within the framework of the implementation of the method according to the invention, correspond either to endogenous proteins of *Pycnoporus*, or to different exogenous proteins of the endogenous proteins of the strain of *Pycnoporus* used for the production of said proteins. In particular these exogenous proteins correspond to endogenous proteins of basidiomycetes other than *Pycnoporus*, such as the basidiomycete enzymes involved in plant biotransformations, or correspond to endogenous proteins of strains of *Pycnoporus* different from the strain of *Pycnoporus* used for the production of said proteins.

A more particular subject of the invention is a method as described above, characterized in that the specific recombinant proteins correspond:

- to the following endogenous proteins of *Pycnoporus*:
  - the metalloenzymes, such as laccase, or tyrosinase,
  - or cellobiose dehydrogenase, xylanase, β-glycosidase, invertase, or α-amylase,
- to the exogenous proteins chosen from the following:
  - the tyrosinases of strains of *Pycnoporus* different from the strain of *Pycnoporus* used for the production of said proteins, such as the tyrosinase of *Pycnoporus sanguineus* when the strain of *Pycnoporus* used for the production of this tyrosinase is different from *Pycnoporus sanguineus*,
  - the laccases of basidiomycetes other than *Pycnoporus*, such as the laccase of *halocyphina villosa* (halophilic basidiomycete),
  - the cinnamoyl esterases A (number EMBL Y09330) and B (number EMBL ANI309807) of *Aspergillus niger*.

Advantageously, in particular in the case of the preparation of specific recombinant proteins corresponding to the endogenous proteins of *Pycnoporus*, the monokaryotic strain of *Pycnoporus* used is deficient in the gene encoding for the endogenous protein to which the specific recombinant protein corresponds, in order not to have to separate the specific recombinant protein from the endogenous protein to which it corresponds during the purification of said recombinant protein.

As a variant, in particular in the case of the preparation of specific recombinant proteins corresponding to the endogenous proteins of *Pycnoporus*, the monokaryotic strain of *Pycnoporus* used may not be deficient in the gene encoding for the endogenous protein to which the specific recombinant protein corresponds, said strain then being transformed using an expression vector containing the gene encoding for the specific recombinant protein labelled in order to distinguish it from the endogenous protein during the purification stage. By way of illustration, the specific recombinant protein can be labelled by a histidine label (His-tag).

A more particular subject of the invention is therefore a method for preparing recombinant laccases corresponding to the endogenous laccases of *Pycnoporus*, characterized in that it comprises:

- a stage of culturing a monokaryotic strain of *Pycnoporus*, if appropriate deficient in the gene encoding for the endogenous laccase of *Pycnoporus*, transformed using an expression vector containing the gene encoding for a laccase of *Pycnoporus*, if appropriate labelled, and the expression of which is placed under the control of a promoter corresponding to the endogenous promoter of this laccase,
- a stage of induction of the abovementioned promoter, in particular by adding ethanol, or agricultural by-products containing lignocellulose such as wheat straw, corn bran and beet pulp, or compounds with an aromatic ring such as 2,5-xylidine, veratrylic acid, guaiacol, veratrylic alcohol, syringaldazine, ferulic acid, caffeic acid and the lignosulphonates,
- the recovery, and, if appropriate, the purification of the recombinant laccase, if appropriate labelled, corresponding to the abovementioned endogenous laccase of *Pycnoporus* produced in the culture medium, in particular according to the method described in Sigoillot J. C., Herpoel I., Frasse P., Moukha S., Lesage-Meessen L., Asther M. 1999; Laccase production by a monokaryotic strain *Pycnoporus cinnabarinus* derived from a dikaryotic strain; World Journal of Microbiology and Biotechnology 15, 481-484.

The invention relates more particularly to a method as defined above, for preparing the recombinant laccase corresponding to the endogenous laccase of *Pycnoporus cinnabarinus* represented by SEQ ID NO: 2, characterized in that it comprises:

- a stage of culturing a monokaryotic strain of *Pycnoporus cinnabarinus*, if appropriate deficient in the gene encoding for the endogenous laccase of *Pycnoporus cinnabarinus*, transformed using an expression vector containing the nucleotide sequence (or nucleic acid) SEQ ID NO: 1 encoding for the recombinant laccase represented by SEQ ID NO: 2, if appropriate labelled, in particular by a His-tag label, and the expression of which is placed under the control of the pLac promoter corresponding to the endogenous promoter of the abovementioned laccase, the sequence of said pLac promoter being represented by SEQ ID NO: 3,
- a stage of induction by ethanol of the abovementioned pLac promoter,
- the recovery, and, if appropriate, the purification of the recombinant laccase, if appropriate labelled, represented by SEQ ID NO: 2 produced in the culture medium, in particular according to the method described in Sigoillot J. C., et al. (1999) mentioned above.

A more particular subject of the invention is a method for preparing recombinant laccases corresponding to the endogenous laccases of *Pycnoporus*, characterized in that it comprises:

- a stage of culturing a monokaryotic strain of *Pycnoporus*, if appropriate deficient in the gene encoding for the endogenous laccase of *Pycnoporus*, transformed using an expression vector containing the gene encoding for a laccase of *Pycnoporus* the expression of which is placed under the control of an exogenous promoter chosen from:
  - the gpd promoter of the expression of the gene encoding for the glyceraldehyde 3-phosphate dehydrogenase of *Schizophyllum commune*, the nucleotide sequence of which is represented by SEQ ID NO: 4,
  - or the sc3 promoter of the expression of the gene encoding for the hydrophobin of *Schizophyllum commune*, the nucleotide sequence of which is represented by SEQ ID NO: 5,
- the recovery, and, if appropriate, the purification of the recombinant laccase corresponding to the abovementioned endogenous laccase of *Pycnoporus* produced in the culture medium, in particular according to the method described in Sigoillot J. C., et al. (1999) mentioned above.

The invention relates more particularly to a method as defined above, for preparing the laccase corresponding to the endogenous laccase of *Pycnoporus cinnabarinus* represented by SEQ ID NO: 2, characterized in that it comprises:

- a stage of culturing a monokaryotic strain of *Pycnoporus cinnabarinus*, if appropriate deficient in the gene encoding for the endogenous laccase of *Pycnoporus cinnabarinus*, transformed using an expression vector containing the nucleotide sequence SEQ ID NO: 1 encoding for the recombinant laccase represented by SEQ ID NO: 2, if appropriate labelled, in particular by a His-tag label, the expression of which is placed under the control of the exogenous gpd or sc3 promoter,
- the recovery, and, if appropriate, the purification of the recombinant laccase, if appropriate labelled, represented by SEQ ID NO: 2 produced in the culture medium, in particular according to the method described in Sigoillot J. C., et al. (1999) mentioned above.

A more particular subject of the invention is a method as defined above, for preparing recombinant tyrosinase corresponding to the tyrosinase of *Pycnoporus sanguineus* represented by SEQ ID NO: 16, characterized in that it comprises:
- a stage of culturing a monokaryotic strain of *Pycnoporus cinnabarinus* transformed using an expression vector containing the nucleotide sequence SEQ ID NO: 15 encoding for the recombinant tyrosinase represented by SEQ ID NO: 16, if appropriate labelled, the sequence SEQ ID NO: 15 being advantageously preceded by the nucleotide sequence delimited by the nucleotides situated at positions 128 and 190 of SEQ ID NO: 1 encoding for the peptide signal of *Pycnoporus cinnabarinus* delimited by the first 21 amino acids of SEQ ID NO: 2, and the expression of which is placed under the control of the pLac promoter corresponding to the endogenous promoter of the laccase of *Pycnoporus cinnabarinus*, the sequence of said pLac promoter being represented by SEQ ID NO: 3,
- a stage of induction by ethanol of the abovementioned pLac promoter,
- the recovery, and, if appropriate, the purification of the recombinant tyrosinase, if appropriate labelled, represented by SEQ ID NO: 16 produced in the culture medium.

The invention relates more particularly to a method as defined above, for preparing recombinant laccase corresponding to the laccase of *halocyphina villosa* represented in FIG. 12 (SEQ ID NO: 18), characterized in that it comprises:
- a stage of culturing a monokaryotic strain of *Pycnoporus cinnabarinus*, if appropriate deficient in the gene encoding for the endogenous laccase of *Pycnoporus cinnabarinus*, transformed using an expression vector containing the nucleotide sequence represented in FIG. 12 (SEQ ID NO: 17) encoding for the recombinant laccase represented by SEQ ID NO: 18, if appropriate labelled, and the expression of which is placed under the control of the pLac promoter corresponding to the end promoter of the laccase of *Pycnoporus cinnabarinus*, the sequence of said pLac promoter being represented by SEQ ID NO: 3,
- a stage of induction by ethanol of the abovementioned pLac promoter,
- the recovery, and, if appropriate, the purification of the recombinant laccase, if appropriate labelled, represented by SEQ ID NO: 18 produced in the culture medium.

A subject of the invention is also the nucleotide sequence encoding for the pLac promoter of the endogenous laccase of *Pycnoporus cinnabarinus*, and corresponding to the sequence SEQ ID NO: 3, or any sequence derived from this promoter by substitution, addition or suppression of one or more nucleotides and retaining the property of being a promoter of the expression of sequences.

The invention also relates to any expression vector, such as the plasmid pELP, characterized in that it comprises the sequence SEQ ID NO: 3 of the abovementioned pLac promoter, or a derived sequence as defined above.

A more particular subject of the invention is any expression vector as defined above, characterized in that it comprises a gene encoding for a specific recombinant protein, and the expression of which is placed under the control of the abovementioned pLac promoter, or of a derived sequence as defined above.

The invention relates more particularly to any expression vector as defined above, characterized in that the specific recombinant protein is a protein corresponding:
- to the following endogenous proteins of *Pycnoporus:*
  - the metalloenzymes, such as laccase, or tyrosinase, or cellobiose dehydrogenase, xylanase, β-glycosidase, invertase, or α-amylase,
- to the exogenous proteins chosen from the following:
  - the tyrosinases of strains of *Pycnoporus* different from the strain of *Pycnoporus* used for the production of said proteins, such as the tyrosinase of *Pycnoporus sanguineus* when the strain of *Pycnoporus* used for the production of this tyrosinase is different from *Pycnoporus sanguineus*,
  - the laccases of basidiomycetes other than *Pycnoporus*, such as the laccase of *halocyphina villosa* (halophilic basidiomycete),
  - the cinnamoyl esterases A and B of *Aspergillus niger*.

The invention also relates to any host cell transformed using an expression vector as defined above.

A more particular subject of the invention is any abovementioned host cell, corresponding to monokaryotic cells of strains of *Pycnoporus*, such as strains of *Pycnoporus cinnabarinus*.

A subject of the invention is also the use of expression vectors as defined above, or of abovementioned host cells, for the implementation of a method for overproducing a specific recombinant protein as defined above.

The invention is further illustrated by means of the following detailed description of the PCES: *Pycnoporus cinnabarinus* Expression System, namely the development of an efficient model of fungal expression making it possible to get rid of the industrial models currently used by the large European groups (*Aspergillus* and *Trichoderma*).

In summary, this is a system of eukaryotic expression and more specifically of filamentous fungi of the basidiomycete group, *Pycnoporus cinnabarinus*, which has been developed by the Inventors for the overexpression of proteins of industrial interest. This work was carried out within the framework of the study of metalloenzymes, such as the laccases, and has in particular made it possible to clone the genes involved in their overexpression, and overproduction of the laccases in large quantities using fermenters, in order to use them in industrial applications for food use (bread making, preparation of drinks in order to modulate the colour of tea, assist in the clarification of fruit juices and alcoholic drinks, formation of agropolymers) and non-food use (treatment of "jeans", degradation of aromatic pollutants in soil, bio-bleaching of lignocellulose fibres in the field of papermaking pulp).

I) Obtaining Monokaryotic Lines of *Pycnoporus Cinnabarinus* for the Transformation of the Fungus and the Overproduction of Genes of Interest.

The purpose of this stage is to isolate then select the haploid cell lines originating from sexual spores of a filamentous fungus, *Pycnoporus cinnabarinus*, which are used at times as host for the expression of the genes of interest. *P. cinnabarinus* is a heterothallic fungus which is found in the wild state in the dikaryotic form (two non-paired nuclei per cell) from which monokaryotic lines are selected (one nucleus per cell), which are potentially more stable and can therefore be used for genetic transformation. Within the framework of this study the Inventors undertook to select monokaryotic lines deficient in laccase activity (lac⁻). In the dikaryotic state, the fungus can multiply by vegetative route (FIG. 1). But, under the influence of particular environmental conditions, it is possible, in the laboratory, to induce the formation of fruiting organs. Within differentiated hyphas called basidia, karyogamy (fusion of the nuclei) then took place, followed by meiosis which leads to the formation of four sexual spores, or genetically different haploid basidiospores. After germination, each basidiospore produces a monokaryotic mycelium. A simple colorimetric test then makes it possible to select only strains devoid of laccase activity.

1) Isolation of the Monokaryotic Strains

The fruiting medium is composed of 2% malt extract (W/V) and agar (1.6% W/V). The cultures are seeded in Petri dishes and kept at 30° C. in the dark for 15 days before being exposed to daylight for 2 to 3 weeks at ambient temperature. The fruiting body appears orange-red. The monospores are then harvested with sterile water on the lid of the Petri dish. The suspension is diluted and cultured in Petri dishes containing an MA2 medium (2% malt W/V and 2% agar W/V) for the purpose of isolating colonies. Isolated pure cultures are seeded and kept in MA2 medium at 30° C. for 5 days and stored at 4° C.

Under these conditions, a monokaryotic strain deficient in laccase activity was selected for transformation with the expression vector for the purpose of overexpressing the laccase gene. A Southern blot study was carried out and made it possible to demonstrate that this strain is deficient in the gene encoding for laccase in *P. cinnabarinus*.

2) Rapid Test for Detecting Laccase Activity of Monospore Colonies

A piece of mycelium is placed in a Petri dish and covered with a drop of 0.1% syringaldazine (W/V) in ethanol solution; After 15 minutes, a change in colour is observed. The 2,2-azino-bis-[3-ethylthiazoline-6-sulphonate] (ABTS) can also be used as substrate in order to reveal laccase activity.

3) Cultures Conditions for Producing Laccase

An inoculum is removed from the precultures which have been growing for 10 days at 30° C. in Roux flasks containing 200 mL of a synthetic medium with the following composition for 1L : maltose (20 g), diammonium tartrate (1.84 g), disodium tartrate (2.3 g), $KH_2PO_4$ (1.33 g), $CaCl_2, H_2O$ (0.1 g), $MgSO_4, 7H_2O$ (0.5 g), $FeSO_4, 7H2O$ (0.07 g), $ZnSO_4, 7H_2O$ (0.046 g), $MnSO_4, H_2O$ (0.035 g), $CuSO_4, 5H_2O$ (0.1 g), yeast extract (1 g), vitamin solution (1 mL/L) according to Tatum et al. (Biochemical mutant strains of *Neurospora* produced by physical and chemical treatment. American Journal of Botany, 37: 38-46, 1950). The mycelium from two flasks is collected, mixed with 100 mL of sterile water and homogenized with an Ultraturax mixer for 60 seconds. In order to produce laccase, the synthetic medium is inoculated with 1 mL of the mycelium suspension. The medium (100 mL) is then incubated at 30° C. in baffled 250-mL Erlenmeyer flasks under stirring (120 rpm).

II) Cloning of the Gene Encoding for the Laccase of *Pycnoporus Cinnabarinus* and its Promoter with a View to the Construction of an Expression Vector This involves a eukaryotic expression system and more particularly of filamentous fungus, *Pycnoporus cinnabarinus*, of the basidiomycete group for the overproduction of specific recombinant proteins. The study model selected is that of the laccase of *P. cinnabarinus*. At present, two fungal models are preferentially used by the large industrial groups. These are *Aspergillus* and *Trichoderma* which belong to the Deuteromycete group. This expression system is therefore completely original and should bridge the gap with regard to development of basidiomycete expression systems compatible with industrial requirements (possibility of large-scale production of proteins secreted in the extracellular medium and culture of the producer fungus in a fermenter).

1) Cloning of the *Pycnoporus Cinnabarinus* Laccase Gene and its Promoter

In a first stage, the Inventors amplified a fragment of the gene encoding for laccase using degenerated nucleotide primers (FIG. 2). The upstream F2 (SEQ ID NO: 6; CAYTG-GCAYGGRTTCTTCC) and downstream R8 (SEQ ID NO: 7; GAGRTGGAAGTCRATGTGRC) degenerated primers were deduced, respectively, from the copper I and IV binding regions of the laccases of related organisms and used in a PCR reaction (Polymerase Chain Reaction) using the genomic DNA of *P. cinnabarinus* I-937. 100 ng of genomic DNA; 0.2 mM of dATP, dCTP, dTTP, and dGTP; 25 pmol of each nucleotide primer; 0.1 volume of 10×Pfu polymerase buffer (100 mM Tris-HCl, 15 mM $MgCl_2$, 500 mM KCl, pH 8.3) and 1 U of Pfu polymerase are added to 10 μl of reaction mixture. The mixture is heated at 94° C. for 5 minutes before adding the polymerase. The reaction conditions are the following: 5 cycles at 94° C., 5 minutes; 55° C., 30 seconds; and 72° C., 4 minutes; then 25 cycles at 94° C., 30 seconds; 55° C., 30 seconds, and 72° C., 3 minutes. A stage of 10 minutes at 72° C. is carried out in order to complete the reaction. A 1.64 kpb band was obtained corresponding to the central part of the laccase gene. The DNA sequence was cloned in pGEM-T in order to sequence this part of the gene.

By a Southern blot technique (FIG. 3), we defined the restriction sites suitable for obtaining a minimum DNA fragment, being able to contain the whole of the laccase gene, and which are capable of serving to amplify the missing 5' and 3' ends. A Southern blot was carried out with the genomic DNA of *P. cinnabarinus* with the BamHI, EcoRI, PstI, PvuII, SacI, SmaI and Xba I enzymes and made it possible to select PstI which produces a 3.5 kpb band by digestion of the genomic DNA. In order to amplify the missing parts of the gene, an inverse PCR technique was used with a mixture of PCR containing nucleotide primers specific to the central part previously isolated and the genomic DNA of *P. cinnabarinus*. The PCR reaction is carried out with 150 ng of DNA cleaved by PstI and looped back on itself by ligation and the nucleotide primers Fex (SEQ ID NO: 8; GGATAACTACTG-GATCCGCG) and Rex (SEQ ID NO: 9; CGCAGTAT-TGCGTGGAGAG). The reaction conditions are the following: 5 cycles at 94° C., 5 minutes; 55° C., 30 seconds; and 72° C., 5 minutes; then 25 cycles at 94° C., 30 seconds; 55° C., 30 seconds, and 72° C., 4 minutes with a final stage of 10 minutes at 72° C. The amplified DNA fragment corresponds to a 2.7 kpb band which was cloned in pGEM-T and sequenced.

The whole of the gene encoding for laccase was then defined by combining the central part and the amplified 5' and 3' parts. In order to verify this sequence, the whole of the gene was amplified (3.331 kpb, FIG. 4) with the nucleotide primers Fin (SEQ ID NO: 10; GACATCTGGAGCGCCTGTC) and Rin (SEQ ID NO: 11; ATCGAAGGTTCCGATGACTGA-CATGAC) from the genomic DNA of *P. cinnabarinus*. This gene was also cloned from the genomic DNA of *P. cinnabarinus* ss3 and proved to be identical to that isolated from *P. cinnabarinus* I-937.

2) Construction of the Expression Vector Using the Laccase Gene Promoter

Starting with the laccase gene sequence, the Inventors cloned the promoter of this gene using the same strategy used previously to isolate the gene, i.e. with an inverse PCR technique on a fragment of genomic DNA (3.5 kpb) cleaved this time by the restriction enzyme BglII (FIG. 5). Two thousand five hundred and twenty seven kpb in front of the laccase gene were thus cloned by inverse PCR and sequenced. This promoter was placed in a vector with a resistance to ampicillin for its sub-cloning in the bacterium and a resistance to the phleomycin used as a selection marker in the fungus. A terminator of the gene encoding for the hydrophobin sc3 of *Schizophyllum commune* was placed downstream in order to terminate the transcription stage. This vector called pELP is used for the homologous expression of laccase (FIG. 6). Two other heterologous promoters were used in this study. These are the promoters of the genes encoding for the glyceraldehyde 3-phosphate dehydrogenase (gpd) and hydrophobin (sc3) of *Schizophyllum commune* (FIG. 6), constituting the expression vectors pEGT and pESC respectively. The whole of the nucleotide sequences of vectors pEGT (SEQ ID NO: 12), pESC (SEQ ID NO: 13), and pELP (SEQ ID NO: 14), are to be found in FIGS. 7, 8 and 9 with the positions of promoter, selection-marker and terminator.

III) Transformation of the Monokaryotic Strain with the Expression Vectors (Study Model: The Laccase of *Pycnoporus Cinnabarinus*)

1) Preparation of the Mycelium for Obtaining Protoplasts

A quarter of a colony cultured in solid medium (10 days) is homogenized with a mixer (Ultraturax type, slow speed) for one minute in 50 ml of YM medium (per litre: glucose 10 g, peptone 5 g, yeast extract 3 g, malt extract 3 g). The homogenate is transferred to a sterile 250-ml Erlenmeyer, to which 50 ml of YM medium is added, then incubated at 30° C. and under stirring (225 rpm) for 20 hours. The culture is once again homogenized for 1 minute (slow speed) and 100 ml of YM medium is added. The homogenate is transferred to a 500-ml Erlenmeyer and cultured overnight at 30° C.

2) Preparation of the Protoplasts

The fungus culture is centrifuged for 10 minutes at 2000 rpm in an oscillating rotor (50 ml tube). 16 g (moist weight) are washed in 40 ml of a 0.5 M $MgSO_4$ or 0.5 M saccharose solution. In the case where saccharose is used, the lytic enzyme used in order to digest the walls is diluted in the saccharose. The mycelium is then centrifuged for 10 minutes at 2000 rpm and the supernatant eliminated. As regards the lysis of the fungal walls, 10 ml of lytic enzyme (Glucanex, Sigma) diluted 1 mg/ml in a 0.5 M $MgSO_4$ solution is added to the mycelium originating from 50 ml of culture. Digestion takes place in a 500-ml Erlenmeyer at 30° C. under gentle stirring over 3 to 4 hours. During this incubation, the appearance of the protoplasts is monitored with a microscope. Ten ml of sterile water are added, then mixed gently. The protoplasts are left for 10 minutes, the time taken for water equilibrium to occur (the protoplasts will float on the surface). They are then centrifuged for 10 minutes at 2000 rpm in an oscillating rotor. The supernatant containing the protoplasts is gently transferred into a new 50 ml of solution. The remaining pellet can be re-incubated with 25 ml of a 0.5M $MgSO_4$ solution in order to recover the maximum amount of protoplasts (the centrifugation stage is then repeated). A volume of 1 M sorbitol, equal to that of the protoplast preparation, is added to it. For 10 minutes, the protoplasts are left to release water. This preparation is then centrifuged for 10 minutes at 2000 rpm. The supernatant is eliminated, leaving a little sorbitol. The protoplasts are transferred into a new tube. The previous tube is rinsed with the 1M sorbitol solution and the protoplasts recovered, added to the new tube. The protoplasts are counted and centrifuged for 10 minutes at 2000 rpm. They are then diluted to a concentration of $2.10^7$ protoplasts per ml in the 1M sorbitol solution. A 0.5 M CaCl2 solution (1/10) is added to the protoplasts.

3) Transformation of the Protoplasts

For the transformation, 100 µl of protoplasts are transformed with 5 to 10 µg of vector (maximum volume of 10 µl) in a sterile 10 ml tube. They are then incubated for 10 to 15 minutes in ice. A volume of a 40% PEG 4000 solution is added, then mixed and the protoplasts are incubated for 5 minutes at ambient temperature. Two and a half ml of regeneration medium (for 100 ml: glucose 2 g, $MgSO_4$, $7H_2O$ 12.5 g, $KH_2PO_4$ 0.046 g, $K_2HPO_4$ 0.1 g, bacto peptone 0.2 g, yeast extract 0.2 g) are added to the protoplasts which are incubated overnight at 30° C. Selection dishes (YM medium containing 7 µg/ml phleomycin, square dishes) are preheated at 37° C. Seven and a half ml of a top agar mixture (1% Low Melting Point agarose diluted in a YM medium containing 7 to 10 µg/ml phleomycin) are added to the regeneration medium containing the protoplasts and are poured into the preheated selection dishes. When the top agar solution has solidified, the dishes are incubated at 30° C. for 4 days. The transformants are then transferred to new selection dishes.

4) Targeting the Transformants

Starting with 16 g of mycelium, approximately 1 to $2.10^7$ protoplasts are generally obtained. The regeneration percentage is 10%. As regards the vector pESC, the monokaryons were transformed with the vector containing the cDNA (BRFM 472, 473 and 474) or the gene encoding for the laccase of *P. cinnabarinus* (BRFM 470 and 471) (FIG. 10). In parallel, other monokaryons were transformed with the promoters pEGT (GPD11, 12 and 13) or with the vector pELP (12.3, 12.7 and 12.8) containing the gene encoding for the laccase (FIG. 10). In view of the results two transformants emerge from the batch with equivalent activities, the transformants 12.7 and GPD14. The activity over time was monitored for the transformants GPD14 and 12.7 (FIG. 11). The activity is detectable from 3-4 days and increases up to 12 days to reach approximately 1200 nkatal/ml i.e. 72000 U/l with the addition of ethanol to the culture medium.

The invention claimed is:

1. A method for preparing a specific recombinant protein, said method being carried out by overexpression of a gene encoding for the specific recombinant protein in a monokaryotic strain of filamentous fungi of the species *Pycnoporus* of the basidiomycete group, comprising:
   (a) culturing the monokaryotic strain of *Pycnoporus*, said strain being transformed with an expression vector containing a gene encoding for the specific recombinant protein, the expression of said gene being placed under the control of pLac3 promoter as set forth in SEQ ID NO: 3,
   (b) inducing the pLac3 promoter, and
   (c) recovering and purifying the specific recombinant protein, produced in the culture medium.

2. The method according to claim 1, wherein the monokaryotic strain of *Pycnoporus* is a strain of *Pycnoporus cinnabarinus*.

3. The method according to claim 1, wherein the specific recombinant proteins overexpressed correspond to endogenous proteins of *Pycnoporus*, or to exogenous proteins corresponding to endogenous proteins of strains of *Pycnoporus* different from the strain of *Pycnoporus* used for the production of said proteins.

4. The method according to claim 1, wherein the specific recombinant proteins correspond:
   (I) to the following endogenous proteins of *Pycnoporus*:
      (i) the metalloenzymes, or
      (ii) cellobiose dehydrogenase, xylanase, β-glycosidase, invertase, or α-amylase, or
   (II) to the exogenous proteins selected from the group consisting of:
      (i) tyrosinases of strains of *Pycnoporus* different from the strain of *Pycnoporus* used for the production of said proteins,
      (ii) laccases of basidiomycetes other than *Pycnoporus*, and
      (iii) cinnamoyl esterases A and B of *Aspergillus niger*.

5. The method according to claim 1, wherein
specific recombinant proteins corresponding to the endogenous proteins of *Pycnoporus* are prepared, and
the monokaryotic strain of *Pycnoporus* is deficient in the gene encoding for the endogenous protein to which the specific recombinant protein corresponds.

6. The method according to claim 1, wherein
specific recombinant proteins corresponding to the endogenous proteins of *Pycnoporus* are prepared, and
the monokaryotic strain of *Pycnoporus* is transformed with an expression vector containing the gene encoding for the specific recombinant protein labelled by a histidine label.

7. The method according to claim 1, wherein recombinant laccases corresponding to the endogenous laccases of *Pycnoporus* are prepared, the method comprising:
   (a) culturing a monokaryotic strain of *Pycnoporus* deficient in the gene encoding for the endogenous laccase of *Pycnoporus* transformed with an expression vector containing the gene encoding for a laccase of *Pycnoporus*, the expression of said gene being under the control of said pLac promoter, (b) inducing the pLac promoter by adding ethanol, or agricultural by-products containing lignocellulose or compounds with an aromatic ring, and
(c) recovering and purifying the recombinant laccase, corresponding to the endogenous laccase of *Pycnoporus* produced in the culture medium.

8. The method according to claim 7, wherein recombinant laccases corresponding to the endogenous laccase of *Pycnoporus cinnabarinus* as set forth in SEQ ID NO: 2 are prepared, the method comprising:
(a) culturing a monokaryotic strain of *Pycnoporus cinnabarinus* deficient in the gene encoding for the endogenous laccase of *Pycnoporus cinnabarinus*, transformed with an expression vector containing the nucleotide sequence as set forth in SEQ ID NO: 1 encoding for the recombinant laccase as set forth in SEQ ID NO: 2, the expression of said laccase being placed under the control of said pLac3 promoter as set forth in SEQ ID NO: 3,
(b) inducing by ethanol the pLac3 promoter, and
(c) recovering and purifying the recombinant laccase as set forth in SEQ ID NO: 2 produced in the culture medium.

9. The method according to claim 1, wherein recombinant tyrosinase corresponding to the tyrosinase of *Pycnoporus sanguineus* as set forth in SEQ ID NO: 16 is prepared, the method comprising:
(a) culturing a monokaryotic strain of *Pycnoporus cinnabarinus* transformed using an expression vector containing the nucleotide sequence as set forth in SEQ ID NO: 15 encoding for the recombinant tyrosinase as set forth in SEQ ID NO: 16, the sequence SEQ ID NO: 15 being preceded by a nucleotide sequence encoding the first 21 amino acids, which is a peptide signal of SEQ ID NO: 2, the expression of said tyrosinase being placed under the control of the pLac3 promoter corresponding to the endogenous promoter of the laccase of *Pycnoporus cinnabarinus*, the sequence of said pLac3 promoter is as set forth in SEQ ID NO: 3,
(b) inducing by ethanol the pLac3 promoter, and
(c) recovering and purifying the recombinant tyrosinase, as set forth in SEQ ID NO: 16 produced in the culture medium.

10. The method according to claim 1, wherein recombinant laccase corresponding to the laccase of *halocyphina villosa* as set forth in SEQ ID NO: 18 is prepared, the method comprising:
(a) culturing a monokaryotic strain of *Pycnoporus cinnabarinus* deficient in the gene encoding for the endogenous laccase of *Pycnoporus cinnabarinus*, transformed using an expression vector containing the nucleotide sequence as set forth in SEQ ID NO: 17 encoding for the recombinant laccase as set forth in SEQ ID NO: 18, the expression of said laccase being placed under the control of the pLac3 promoter corresponding to the endogenous promoter of the laccase of *Pycnoporus cinnabarinus*, the sequence of said pLac3 promoter is as set forth in SEQ ID NO: 3,
(b) inducing by ethanol the pLac3 promoter, and
(c) recovering and purifying the recombinant laccase as set forth in SEQ ID NO: 18 produced in the culture medium.

11. An isolated nucleic acid comprising pLac3 promoter of the endogenous laccase of *Pycnoporus cinnabarinus* as set forth in SEQ ID NO: 3.

12. An expression vector comprising the isolated nucleic acid of claim 11.

13. The expression vector according to claim 12, further comprising a gene encoding for a specific recombinant protein, the expression of which is placed under the control of the pLac3 promoter.

14. The expression vector according to claim 13, wherein the specific recombinant protein is a protein corresponding to
(1) the following endogenous proteins of *Pycnoporus*: the metalloenzymes, laccase, tyrosinase, cellobiose dehydrogenase, xylanase, beta-glycosidase, invertase, alpha-amylase,
(2) the following exogenous proteins: the tyrosinases of strains of *Pycnoporus* different from the strain of *Pycnoporus* used for the production of said proteins, the tyrosinase of *Pycnoporus sanguineus* when the strain of *Pycnoporus* used for the production of this tyrosinase is different from *Pycnoporus sanguineus*, the laccases of basidiomycetes other than *Pycnoporus*, the laccase of *halocyphina villosa* (*halophilic basidiomycete*), the cinnamoyl esterases A and B of *Aspergillus niger*.

15. An isolated host cell transformed with the expression vector according to claim 13.

16. The isolated host cell according to claim 15, corresponding to monokaryotic cells of strains of *Pycnoporus*, or strains of *Pycnoporus cinnabarinus*.

17. The method according to claim 4, wherein the metalloenzymes are chosen from laccase or tyrosinase.

18. The method according to claim 4, wherein the tyrosinases of strains of *Pycnoporus* different from the strain of *Pycnoporus* used for the production of said proteins, is the tyrosinase of *Pycnoporus sanguineus*.

19. The method according to claim 4, wherein the laccases of basidiomycetes other than *pycnoporus* is the laccase of *halocyphina villosa*.

20. The method according to claim 7, wherein the lignocellulose is selected from the group consisting of wheat straw, corn bran and beet pulp.

21. The method according to claim 7, wherein the compounds with an aromatic ring is selected from the group consisting of 2,5-xylidine, veratrylic acid, guaicol, veratrylic alcohol, syringaldazine, ferulic acid, caffeic acid and the lignosulphonates.

22. The method according to claim 1, for preparing recombinant laccases corresponding to the endogenous laccases of *Pycnoporus*, the method comprising:
(a) culturing a monokaryotic strain of *Pycnoporus* transformed with an expression vector containing a gene encoding for a laccase of *Pycnoporus*, the expression of said gene being under the control of the pLac3 promoter,
(b) inducing the pLac3 promoter by adding ethanol, or agricultural by-products containing lignocellulose, or compounds with an aromatic ring, and
(c) recovering and purifying the recombinant laccases corresponding to the endogenous laccase of *Pycnoporus* produced in the culture medium.

23. The method according to claim 7, for preparing the recombinant laccases corresponding to endogenous laccases of *Pycnoporus cinnabarinus* as set forth in SEQ ID NO: 2, the method comprising:
(a) culturing a monokaryotic strain of *Pycnoporus cinnabarinus*, transformed using an expression vector containing the nucleotide sequence as set forth in SEQ ID NO: 1 encoding the recombinant laccase as set forth in SEQ ID NO: 2, the expression of said recombinant laccase being under the control of the pLac3 promoter corresponding to the endogenous promoter of the laccase, the sequence of said pLac3 promoter is as set forth in SEQ ID NO: 3, (b) inducing by ethanol the pLac3 promoter,
(c) recovering and purifying the recombinant laccase, as set forth in SEQ ID NO: 2 produced in the culture medium.

24. The method according to claim 1, for preparing recombinant laccases corresponding to the laccase of *Halocyphina villosa* as set forth in SEQ ID NO: 18, the method comprising:
   (a) culturing a monokaryotic strain of *Pycnoporus cinnabarinus* transformed using an expression vector containing the nucleotide sequence as set forth in SEQ ID NO: 17 encoding for the recombinant laccase as set forth in SEQ ID NO: 18, the expression of said laccase being placed under the control of the pLac3 promoter corresponding to the endogenous promoter of the laccase of *Pycnoporus cinnabarinus*, the sequence of said pLac3 promoter is as set forth in SEQ ID NO: 3,
   (b) inducing by ethanol the pLac3 promoter,
   (c) recovering and purifying the recombinant laccase as set forth in SEQ ID NO: 18 produced in the culture medium.

* * * * *

UNITED STATES PATENT AND TRADEMARK OFFICE
CERTIFICATE OF CORRECTION

PATENT NO. : 8,481,706 B2  Page 1 of 1
APPLICATION NO. : 10/586348
DATED : July 9, 2013
INVENTOR(S) : Alves et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1847 days.

Signed and Sealed this
Eighth Day of September, 2015

Michelle K. Lee
*Director of the United States Patent and Trademark Office*

SEQUENCE LISTING

<160> NUMBER OF SEQ ID NOS: 18

<210> SEQ ID NO 1
<211> LENGTH: 3330
<212> TYPE: DNA
<213> ORGANISM: Pycnoporus cinnabarinus
<220> FEATURE:
<221> NAME/KEY: CDS
<222> LOCATION: (128)..(310)
<220> FEATURE:
<221> NAME/KEY: CDS
<222> LOCATION: (368)..(436)
<220> FEATURE:
<221> NAME/KEY: CDS

```
<222> LOCATION: (490)..(610)
<220> FEATURE:
<221> NAME/KEY: CDS
<222> LOCATION: (664)..(777)
<220> FEATURE:
<221> NAME/KEY: CDS
<222> LOCATION: (833)..(896)
<220> FEATURE:
<221> NAME/KEY: CDS
<222> LOCATION: (960)..(1055)
<220> FEATURE:
<221> NAME/KEY: CDS
<222> LOCATION: (1114)..(1270)
<220> FEATURE:
<221> NAME/KEY: CDS
<222> LOCATION: (1334)..(1531)
<220> FEATURE:
<221> NAME/KEY: CDS
<222> LOCATION: (1592)..(1648)
<220> FEATURE:
<221> NAME/KEY: CDS
<222> LOCATION: (1705)..(1911)
<220> FEATURE:
<221> NAME/KEY: CDS
<222> LOCATION: (1968)..(2255)

<400> SEQUENCE: 1
ctgcagacat ctggagcgcc tgtctttccc ctagtataaa tgatgtctgt ccgcaggtcc      60
ttgaagaccg ctcgagtccc acttgagttt taggtaggac ctgtccacca aaccctctt     120 tctgatc atg tcg agg ttc cag tcc ctc ttt ttc ttc gtc ctc gtc tcc     169
        Met Ser Arg Phe Gln Ser Leu Phe Phe Phe Val Leu Val Ser
        1               5                   10 ctc acc gct gtg gcc aac gca gcc ata ggg cct gtg gcg gac ctg acc     217
Leu Thr Ala Val Ala Asn Ala Ala Ile Gly Pro Val Ala Asp Leu Thr
15                  20                  25                  30 ctt acc aat gcc cag gtc agc ccc gat ggc ttc gct cgc gag gcc gtc     265
Leu Thr Asn Ala Gln Val Ser Pro Asp Gly Phe Ala Arg Glu Ala Val
                35                  40                  45 gtg gtg aac ggt atc acc cct gcc cct ctc atc aca ggc aat aag         310
Val Val Asn Gly Ile Thr Pro Ala Pro Leu Ile Thr Gly Asn Lys
            50                  55                  60 gtatgtatat gctgctcgtc cctcagagct acatacatct gatccacaat cgtttag      367 ggc gat cga ttc cag ctc aat gtc atc gac cag ttg aca aat cat acc     415
Gly Asp Arg Phe Gln Leu Asn Val Ile Asp Gln Leu Thr Asn His Thr
                65                  70                  75 atg ttg aaa aca tct agt att gtaagggttc agttttctccc gactaccatg       466
Met Leu Lys Thr Ser Ser Ile
                80 ttattgacca tcaccactcg tag cat tgg cac ggc ttc ttc cag caa ggc acg   519
                        His Trp His Gly Phe Phe Gln Gln Gly Thr
                            85                  90 aac tgg gcc gat ggt ccc gcg ttc gtg aac cag tgt ccc atc gct tcg     567
Asn Trp Ala Asp Gly Pro Ala Phe Val Asn Gln Cys Pro Ile Ala Ser
95                  100                 105                 110 ggc cac tcg ttc ttg tat gac ttt caa gtt ccc gac caa gca g           610
Gly His Ser Phe Leu Tyr Asp Phe Gln Val Pro Asp Gln Ala
                115                 120 gtacgaattc cgtacacgtt tcattgcgtc gcaactaaac ctcctcttac tag gg       665
                                                            Gly
                                                            125 act ttc tgg tac cat agc cat ctc tcc acg caa tac tgc gat ggt ttg     713
Thr Phe Trp Tyr His Ser His Leu Ser Thr Gln Tyr Cys Asp Gly Leu
            130                 135                 140 agg ggg cct ttc gtc gtc tac gac ccc aac gat cct cac gct agc ctg     761
Arg Gly Pro Phe Val Val Tyr Asp Pro Asn Asp Pro His Ala Ser Leu
```

-continued

```
                 145                 150                 155
tat gac att gat aac g gtgagcagat catggtatcg caatattgcg tccacttatg     817
Tyr Asp Ile Asp Asn
        160 cttcctggca tccag ac  gac act gtc att acg ctg gct gat tgg tat cac     867
                    Asp Asp Thr Val Ile Thr Leu Ala Asp Trp Tyr His
                            165                 170 gtt gct gcc aag ctc gga cct cgc ttc cc  gtacgtgtca aatgtctacg        916
Val Ala Ala Lys Leu Gly Pro Arg Phe Pro
175                 180 agagatctca catatacgac tagactcact tcgctgatta cag a ttt ggc tcc gat    972
                                                Phe Gly Ser Asp
                                                        185 tca acc ctt atc aat gga ctt ggt cga acc act ggc ata gca ccg tcc     1020
Ser Thr Leu Ile Asn Gly Leu Gly Arg Thr Thr Gly Ile Ala Pro Ser
        190                 195                 200 gac ttg gca gtt atc aag gtc acg cag ggc aag cg  gtaagtatgg          1065
Asp Leu Ala Val Ile Lys Val Thr Gln Gly Lys Arg
205                 210                 215 atggtcatca ctgcacattg gctctgatac atggccttgt ttccacag c tac cgc      1120
                                                       Tyr Arg ttc cgc ttg gtg tcg ctt tct tgc gat ccg aac cat aca ttc agc att     1168
Phe Arg Leu Val Ser Leu Ser Cys Asp Pro Asn His Thr Phe Ser Ile
        220                 225                 230 gat aat cac aca atg act ata att gag gcg gac tcg atc aac act caa     1216
Asp Asn His Thr Met Thr Ile Ile Glu Ala Asp Ser Ile Asn Thr Gln
235                 240                 245                 250 ccc cta gag gtt gat tca atc cag att ttt gcc gcg cag cgc tac tcc     1264
Pro Leu Glu Val Asp Ser Ile Gln Ile Phe Ala Ala Gln Arg Tyr Ser
                255                 260                 265 ttc gtg gtaggtcgta ggctcctgtc atcaagtttg cagacattct tagatacacc      1320
Phe Val tttttcaatg cag ctg gat gct agc cag ccg gtg gat aac tac tgg atc     1369
            Leu Asp Ala Ser Gln Pro Val Asp Asn Tyr Trp Ile
                    270                 275                 280 cgc gca aac cct gcc ttc gga aac aca ggt ttt gct ggt gga atc aat     1417
Arg Ala Asn Pro Ala Phe Gly Asn Thr Gly Phe Ala Gly Gly Ile Asn
                285                 290                 295 tct gcc atc ctg cgt tat gat ggc gca ccc gag atc gag cct acg tct     1465
Ser Ala Ile Leu Arg Tyr Asp Gly Ala Pro Glu Ile Glu Pro Thr Ser
                300                 305                 310 gtc cag act act cct acg aag cct ctg aac gag gtc gac ttg cat cct     1513
Val Gln Thr Thr Pro Thr Lys Pro Leu Asn Glu Val Asp Leu His Pro
        315                 320                 325 ctc tcg cct atg cct gtg gtacgtgtct caaagaacct cgatcactaa            1561
Leu Ser Pro Met Pro Val
        330 gtgcatgtca actcatatgg tgcatgacag cct ggc agc ccc gag ccc gga ggt   1615
                                    Pro Gly Ser Pro Glu Pro Gly Gly
                                            335                 340 gtc gac aag cct ctg aac ttg gtc ttc aac ttc gtgagtactg gcgcgcttcc   1668
Val Asp Lys Pro Leu Asn Leu Val Phe Asn Phe
345                 350 gtagcacacg ttcgaacaaa gcctgatacc atgcag aac ggc acc aac ttc ttc     1722
                                        Asn Gly Thr Asn Phe Phe
                                                355 atc aac gac cac acc ttt gtc ccg ccg tct gtc cca gtc ttg cta caa     1770
Ile Asn Asp His Thr Phe Val Pro Pro Ser Val Pro Val Leu Leu Gln
360                 365                 370                 375
```

```
atc ctc agt ggg gcg cag gcg gct cag gac ctg gtc ccg gag ggc agc      1818
Ile Leu Ser Gly Ala Gln Ala Ala Gln Asp Leu Val Pro Glu Gly Ser
            380                 385                 390 gtg ttc gtt ctt ccc agc aac tcg tcc att gag ata tcc ttc cct gcc      1866
Val Phe Val Leu Pro Ser Asn Ser Ser Ile Glu Ile Ser Phe Pro Ala
        395                 400                 405 act gcc aat gcc cct gga ttc ccc cat ccg ttc cac ttg cac ggt          1911
Thr Ala Asn Ala Pro Gly Phe Pro His Pro Phe His Leu His Gly
    410                 415                 420 gtacgtctgc cttcccctcg tctaaaggcg gagtcgatat ctgactccca tcacag cac    1970
                                                              His gcc ttc gct gtc gtc cgg agc gcc ggg agc agc gtc tac aac tac gac      2018
Ala Phe Ala Val Val Arg Ser Ala Gly Ser Ser Val Tyr Asn Tyr Asp
        425                 430                 435 aac ccg atc ttc cgc gac gtc gtc agc acc ggc cag ccc ggc gac aac      2066
Asn Pro Ile Phe Arg Asp Val Val Ser Thr Gly Gln Pro Gly Asp Asn
440                 445                 450                 455 gtc acg att cgc ttc gag acc aat aac cca ggc ccg tgg ttc ctc cac      2114
Val Thr Ile Arg Phe Glu Thr Asn Asn Pro Gly Pro Trp Phe Leu His
            460                 465                 470 tgc cac att gac ttc cac ctc gac gca ggc ttt gct gta gtc atg gcc      2162
Cys His Ile Asp Phe His Leu Asp Ala Gly Phe Ala Val Val Met Ala
        475                 480                 485 gag gac act ccg gac acc aag gcc gcg aac cct gtt cct cag gcg tgg      2210
Glu Asp Thr Pro Asp Thr Lys Ala Ala Asn Pro Val Pro Gln Ala Trp
    490                 495                 500 tcg gac ttg tgc ccc atc tat gat gca ctt gac ccc agc gac ctc          2255
Ser Asp Leu Cys Pro Ile Tyr Asp Ala Leu Asp Pro Ser Asp Leu
505                 510                 515 tgagcgggat tgttactgtg acctggtgtg gggggaacat gtcgagggct ttcatcgatc    2315
agggactttc aaggttggca taatatacct cacggcctgg atgactcgga cagcgtgtgg    2375
gcgtgggtgt aactctgctt gatgttgaaa aaggatttt atgtagaaca atttatgagc     2435
aatcagcaat caataggatt gtgtcggttt cgacgaaatg tcttgtctcc ctgacattac    2495
ttttgtgcga gaaatgggtc catgatacac atcattgagc tctcaatacc agaaggatt     2555 acccatgtca atacccaaga tcatgtcttc gctgtccgca atggtctcat gttgcgttga    2615
gcagatcgca gtacgttgaa aagcgattag tattacatgc aacatgcaac atttggaagg    2675
gggcatgcag aggttcagct cgcgtcagtc ggccaagtag cgacctttgc cgcactgcct    2735
gttaacctga acgtatgctt cagaactccg tcggtatcga gagcgatcgt gtacgttccg    2795
ggatagatcc attgatcccc gctctggtcg gcgcgtgcga tggccccgag cgtcaccggc    2855
agcttcgcga tcgcgctttt cctagggcg aggccgtgta cccgcgtgta cgagacgagc     2915
tgcttgttcg ggtggggcga aggcccgaag gagccactca cgaagagcaa tgcgacgtaa    2975
tccgaggtag ccttgcccgt gttagtcaca cgcacggaga acgtgtcgag cggcgcgagg    3035
tcgaggaagg cggcgctctt ctgaccgcgc tgtacgaggt cggaaatcga atacgtcgat    3095
ggcggtcctc caaagtccgt gacgttggtc gcatcggccg ccgcgcctgg agctgcccaa    3155
gagaaatcga aggtggtgaa gtgcagtcca aagccaaatt cgtagaccgg cgtgccggtg    3215
taccacttgt atgtacgccc cgggttcgac gcgcttgggc gaagggtcat gtcagtcatc    3275
ggaacctgat cagcgtagat ggctgggtat tgggtgatgg gcaggcgtcc tgcag         3330

<210> SEQ ID NO 2
<211> LENGTH: 518
<212> TYPE: PRT
<213> ORGANISM: Pycnoporus cinnabarinus
```

```
<400> SEQUENCE: 2

Met Ser Arg Phe Gln Ser Leu Phe Phe Val Leu Val Ser Leu Thr
1               5                   10                  15

Ala Val Ala Asn Ala Ala Ile Gly Pro Val Ala Asp Leu Thr Leu Thr
            20                  25                  30

Asn Ala Gln Val Ser Pro Asp Gly Phe Ala Arg Glu Ala Val Val Val
            35                  40                  45

Asn Gly Ile Thr Pro Ala Pro Leu Ile Thr Gly Asn Lys Gly Asp Arg
        50                  55                  60

Phe Gln Leu Asn Val Ile Asp Gln Leu Thr Asn His Thr Met Leu Lys
65                  70                  75                  80

Thr Ser Ser Ile His Trp His Gly Phe Phe Gln Gln Gly Thr Asn Trp
                85                  90                  95

Ala Asp Gly Pro Ala Phe Val Asn Gln Cys Pro Ile Ala Ser Gly His
            100                 105                 110

Ser Phe Leu Tyr Asp Phe Gln Val Pro Asp Gln Ala Gly Thr Phe Trp
            115                 120                 125

Tyr His Ser His Leu Ser Thr Gln Tyr Cys Asp Gly Leu Arg Gly Pro
        130                 135                 140

Phe Val Val Tyr Asp Pro Asn Asp Pro His Ala Ser Leu Tyr Asp Ile
145                 150                 155                 160

Asp Asn Asp Asp Thr Val Ile Thr Leu Ala Asp Trp Tyr His Val Ala
                165                 170                 175

Ala Lys Leu Gly Pro Arg Phe Pro Phe Gly Ser Asp Ser Thr Leu Ile
            180                 185                 190

Asn Gly Leu Gly Arg Thr Thr Gly Ile Ala Pro Ser Asp Leu Ala Val
        195                 200                 205

Ile Lys Val Thr Gln Gly Lys Arg Tyr Arg Phe Arg Leu Val Ser Leu
        210                 215                 220

Ser Cys Asp Pro Asn His Thr Phe Ser Ile Asp Asn His Thr Met Thr
225                 230                 235                 240

Ile Ile Glu Ala Asp Ser Ile Asn Thr Gln Pro Leu Glu Val Asp Ser
            245                 250                 255

Ile Gln Ile Phe Ala Ala Gln Arg Tyr Ser Phe Val Leu Asp Ala Ser
            260                 265                 270

Gln Pro Val Asp Asn Tyr Trp Ile Arg Ala Asn Pro Ala Phe Gly Asn
        275                 280                 285

Thr Gly Phe Ala Gly Gly Ile Asn Ser Ala Ile Leu Arg Tyr Asp Gly
        290                 295                 300

Ala Pro Glu Ile Glu Pro Thr Ser Val Gln Thr Thr Pro Thr Lys Pro
305                 310                 315                 320

Leu Asn Glu Val Asp Leu His Pro Leu Ser Pro Met Pro Val Pro Gly
            325                 330                 335

Ser Pro Glu Pro Gly Gly Val Asp Lys Pro Leu Asn Leu Val Phe Asn
            340                 345                 350

Phe Asn Gly Thr Asn Phe Phe Ile Asn Asp His Thr Phe Val Pro Pro
        355                 360                 365

Ser Val Pro Val Leu Leu Gln Ile Leu Ser Gly Ala Gln Ala Ala Gln
        370                 375                 380

Asp Leu Val Pro Glu Gly Ser Val Phe Val Leu Pro Ser Asn Ser Ser
385                 390                 395                 400

Ile Glu Ile Ser Phe Pro Ala Thr Ala Asn Ala Pro Gly Phe Pro His
            405                 410                 415
```

Pro Phe His Leu His Gly His Ala Phe Ala Val Val Arg Ser Ala Gly
        420                 425                 430

Ser Ser Val Tyr Asn Tyr Asp Asn Pro Ile Phe Arg Asp Val Val Ser
        435                 440                 445

Thr Gly Gln Pro Gly Asp Asn Val Thr Ile Arg Phe Glu Thr Asn Asn
        450                 455                 460

Pro Gly Pro Trp Phe Leu His Cys His Ile Asp Phe His Leu Asp Ala
465                 470                 475                 480

Gly Phe Ala Val Val Met Ala Glu Asp Thr Pro Asp Thr Lys Ala Ala
                485                 490                 495

Asn Pro Val Pro Gln Ala Trp Ser Asp Leu Cys Pro Ile Tyr Asp Ala
        500                 505                 510

Leu Asp Pro Ser Asp Leu
        515

<210> SEQ ID NO 3
<211> LENGTH: 2527
<212> TYPE: DNA
<213> ORGANISM: Pycnoporus cinnabarinus

<400> SEQUENCE: 3
agatctccga accagaaatg cgattgcgtt caggcccaat taagaataaa gctgcgtcag      60
ggcagcgacg tatcttgatc catcattgac tcaccggcat cggcgtcaac accaaagcaa     120
gctcgtccca cccataggcg tgcaccggcc ggcgtgcgcc attgaggtac atgagcgggg     180
cgaaagtccg ccattggtag ccctgtcgtg gacgcgcggc gatgaaacgt ttcccaccat     240
tgggaagaaa cgtctgcggc ccatcatccc ttcaccggat gacaaggcgg cgtcgcgcct     300
ttgccgcaga ggccggcggg cgacatgcac agcgaaggtc cgttgcggat gggaagcagg     360
caatcagtgg gtgtcctacg ccgccacgat ggtcggggag cgtaggcgcc ctcccataag     420
gcggcaagca tcatgatgct ctccgattcg ggaagcctgg tgcgatgctg gagagactct     480
ctccgagaga ccagtgtgcg caacgttcct ggcctggaag actttaaagt gagtgtagaa     540
gggcgagcag aggacgatca tcggattgca ggaaccatcg gcatcctcag cctgggaagg     600
atggctcttg gtagacattc gcggaaggtg tcctagatgt gagcgggctt cttggatgat     660
catgtcgtaa cttttctga cctcgtcggt ggtacgcatg caggattga gcattacggt     720
atgcctccca ttcataaacg ataaccccctt ccttcaggtt ggtcatctcc atagagcggc     780
acgctctcaa ggcctaggct attcacacct ccttcgcaac atccctattc acggtgtctg     840
taaggaacga cttgtcatgg gatcacatga agtgcagcat actgttcgcc ggtctcgcag     900
tacagacgct agtacgggaa gtcgacatcc aagcgttcag tcaccacatg caaaaaagc     960
tgcaccatac tctttatggt gagttgttcg tgagtggtat acagtcattc atgagggaat    1020
gcccaccgga tagggtgtgg cggccgcaat attcatcgcc tggcaatagt cgatgtgcgt    1080
ccttgttcaa tgaatatcat gggtcacatg tggagacggt taaacagcgt tgactgtgaa    1140
tccctggtgt gtgttgggcc gaacaggtac gttgcaggaa caccaatatc tcttcggcag    1200
cccagttctt tgcgagcggc acaggcaggc atcgcgcaac agatcccagc catccggcct    1260
ctgacattcg ggatacctga agcccttcag gtacggagcg aagaggtggg ctctctgcag    1320
cgattggcgg acggatagct gtatttcctc tctcaccatt gggaagatgt gaaaggctcc    1380
atcatatagc ggctcaactc tacctcgaat gtccaaacac ggcgggaata cttatttatg    1440
tggacaaggc cgagctatga tagcttgctc ccgaagttgg taagtcccgc aatctgcggt    1500

```
tcaggcaaca gtctcggaaa aataagaaga atattgtagg tgcgtgtagg cgtatcgccc    1560
aaatgcgcac acacggaggc tttaggagat gaagcgcccg tgagcggtaa gggagttggt    1620
tcaccgccgc cccgaccgac tctctctctt tcccagcatc atgtctcggc gcaaacttta    1680
ccctctattg accaactcca cgagaaagca ggaacagctt ccttgtctct catgacgtcc    1740
gcaatccaga cccttagccg gttcgttact catcgttatc cctgccgcca tggtagtgga    1800
gtcagcctgg ccagtgcgta gtcccgtctc tcttgctgca ctagagaagc cccatgagac    1860
agcgtttttt gctttatttc tgctgtttct atagacacca tagggcaaa cgatcctgca     1920 cgcccagagg tattgggctc gtcagattcc cagttttct cctcggtctg aatcggctgc     1980
acggcagata atcggccgg aaatgctata gcccttcata gcccgctatg agagtcgcaa    2040
aaggcttgtc agtcaggtcg gtcgagtggc tctcacgaag agcgtcaact tcgcgcgaca    2100
gccgcctttc agggcaagat agatcctccc atcatcccct actgcgctca gcgccggtac    2160
cgaacaattg acttaccgac atcctccggg acgcgcaaat gctgttcgac ggaacgtaat    2220
cctcttcgtc ccgcctcttt tcgctctcac gcattccgtg tggttcgcgc gacggccgct    2280
catcaggacc agaccagtct caatgtctgg taccggcaca atggtgacac tgcggcaact    2340
gagtaggtct ggtcactctg gtgcaccgtc gcttacgctg accttcggga tactgtcctg    2400
cagacatctg gagcgcctgt ctttccccta gtataaatga tgtctgtccg caggtccttg    2460
aagaccgctc gagtcccact tgagttttag gtaggacctg tccaccaaac ccctctttct    2520
gatcatg                                                              2527
```

<210> SEQ ID NO 4
<211> LENGTH: 643
<212> TYPE: DNA
<213> ORGANISM: Artificial Sequence
<220> FEATURE:
<223> OTHER INFORMATION: Description of Artificial Sequence: Synthetic
      vector

<400> SEQUENCE: 4

```
cgaccgagcg cgcgccaccc agcctatccc gcgcgggtcg ggacccaaaa taagcgggcc      60
ccgccgcgcc ccgtcgggcg agcgggtgta tctacgaacg gaactgggag gcgactcgga     120
agagtttggt tagaaagggg aacaccatcg cggacggccc agtgctctgg dcagctgagc     180
gtgcattgtg ttcaattctg acctgtggca tgtaaggaac gtgctcggga tcggagggtg    240
gcgcgagagc ctcttcggtg tgagattagt aactgtactg cgaagccgcg gagggggttag    300 gatgagaggt agacagggtc gcagcccagg tgcgagaagg actgcgaagg actgttcttc    360
gaccgcgcac ctgcaattgc gcgcatggat agaatagagc gtcgccctcg aggggggactc    420 gaccagggct ggtggtggcg cccgacggga ctggctgggc atttgcagat ggcgcgcagt    480
ccaggccgcc gccgatgtgt tcatcccgtt ttgtcagtat cgatcggatc tttcgggcgt    540
gggtataaaa gcgcgccgcc cgccgtctcc ctctttctcc agcactccca tccagagcac    600
ttccctctcc catcgcatcc catcacacaa taatgcccat cac                       643
```

<210> SEQ ID NO 5
<211> LENGTH: 1033
<212> TYPE: DNA
<213> ORGANISM: Artificial Sequence
<220> FEATURE:
<223> OTHER INFORMATION: Description of Artificial Sequence: Synthetic
      vector

<400> SEQUENCE: 5

-continued

```
agcttctccg gccccgaatc gaacggcagg atgtgtgggc gtgtccaata ttgccatgaa      60
aatctgtcag aagtgagccc tctcgtcacc ctgtacagct tcgctgagtt gaaaagcagg     120
gttcatcttg ggctcactga tgcactgagc tcgaccggag aactaaatga ccagccggag     180
tgttcactaa cttaacgccg ggtattcagg gcagcttctc tatgttgcgc ctacgacgta     240
gatcaccgcc catgaacggg ggaaacgggg aggggtgcgt ttggtacgtc tttacgtctg     300
gctatgttgt attgaccagc gtctgcagaa gatgggcacg acgatgcgcc gagccggcca     360
gtgtcgtcgg atgtccactg ttgaggccat ccttttgcta gacagacgga agagctttgg     420
aggtgcgatt cctctacgaa tgggaagggg cttagatgga gagtgacacg tctgagctcc     480
ccaacacgcc ttcgccgagg gtgcgtctcc gcggacattc acctcagttc attgttctga     540
cctgcctaat tgtatagacc ggccaacaac cttgctgacg cccatcataa cagtgccctg     600
cacagagcct tcccactcag tcggcgcctc cctcaatcaa tcccactaac tcgccggctc     660
tgccccttcg ccgctcgaca cgtcgcttgg aagagcccgg gcacgggcgt ccgctccccc     720
cttccctccg cgtcgtcatg cacgcagcgt taatgttgct gcaggcgagc cgtaagtata     780
ttcaaaggcg tagcgaatga atagcaggcg cgcggggacc tggcacgcgc ggcatgaaca     840
tgcagacttg ggtgacgata acttgaactc agacgcggcg aatgaatatc caaacgcgcg     900
ggaagaaaat aatttacggg agcctcccca ggtataaaag cccctcaccc gctcactctt     960
tctccagtcg aacaccccag ttcaactacc cagcccttcc ttccttcgct atccttcytt    1020
acaacctgct cgc                                                       1033
```

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caytggcayg grttcttcc                                                   19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gagrtggaag tcratgtgrc                                                  20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggataactac tggatccgcg                                                  20

<210> SEQ ID NO 9
<211> LENGTH: 19
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 9
cgcagtattg cgtggagag                                                    19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gacatctgga gcgcctgtc                                                    19

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atcgaaggtt ccgatgactg acatgac                                           27

<210> SEQ ID NO 12
<211> LENGTH: 5122
<212> TYPE: DNA
<213> ORGANISM: Artificial Sequence
<220> FEATURE:
<223> OTHER INFORMATION: Description of Artificial Sequence: Synthetic
      vector

<400> SEQUENCE: 12
catgggatat cgcatgcctg cagagctcta gagtcgacgg gcccggtacc gcggccgcct       60
taagacgcgt ggatccgcag gtgaacgcgc tatcggtgg gatattcggg cgacgggagc      120
ctcggcaatc tgagcctcgt tactgcctag caaattcgga atcccttcga tgtcataggg     180
tcgcggacaa gtgatcgtct tgctacatac tccaaggtgt tgactcattc cctcgataat    240
gaacattgtt gttgttgttt gttctctatc cgctcagtca cgcgacccca cacgtgcatg     300
gttgaacttc gccacgcaac aaccgcatga cgacatggcg aacctaagta aaggctgagt    360
cgtggactaa agcactccac tttacggcga ggatgccagt ctacgtcatg aatgaagcct    420
caggtcccga gtaaggggg tacaaaagga gggtgaaagg tggacgtttt cttaccatcc     480
ttccacctcc cagaccacca tgccgggaat tcccagcttg ctcaaaaagg ttctgcccgt    540
acgcccgcga aattccttcg aggtggcccc tatcgcatac atgcacgact caaaacatc     600 cattctatca ttttgggatc gtacaattat tagacatgtt gtacaacgtt acattccttt    660
cttcttttac tctccggccc agtctatgta gaggtaaagt acaagcgtcc aaaggatcag   720
gcacttagag cgcgccgtct tgcttcgccg cttagagcgc gccgtcctgc ttcgccgcgt   780
agacgagcag gtcgcagaca cggcgggagt agccccactc gttgtcgtac caggcaatga   840
gcttcacgaa gctcttgctg atcgcgatgc cggggatcga tccacgcgtc ttaaggcggc    900
cgcggtaccc cctcggaccc gtcgggccgc gtcggaccgg cggtgttggt cggcgtcggt    960
cagtcctgct cctcggccac gaagtgcacg cagttgccgg ccgggtcgcg cagggcgaac  1020
tcccgccccc acggctgctc gccgatctcg gtcatggccg gcccggaggc gtcccggaag  1080
```

```
ttcgtggaca cgacctccga ccactcggcg tacagctcgt ccaggccgcg cacccacacc   1140
caggccaggg tgttgtccgg caccacctgg tcctggaccg cgctgatgaa cagggtcacg   1200
tcgtcccgga ccacaccggc gaagtcgtcc tccacgaagt cccgggagaa cccgagccgg   1260
tcggtccaga actcgaccgc tccggcgacg tcgcgcgcgg tgagcaccgg aacggcactg   1320
gtcaacttgg ccatgcatgg tgatgggcat tatgtgtgat gggatgcgat gggagaggga   1380
agtgctctgg atgggagtgc tggagaaaga gggagacggc gggcggcgcg ccttttatac   1440
ccacgcccga aagatccgat cgatactgac aaaacgggat gaaacacatcg gcggcggcct   1500
ggactgcgcg ccatctgcaa atgcccagcc agtcccgtcg ggcgccacca ccagccctgg   1560
tcgagtcccc ctcgagggcg acgctctatt ctatccatgc gcgcaattgc aggtgcgcgg   1620
tcgaagaaca gtccttcgca gtccttctcg cacctgggct gcgaccctgt ctacctctca   1680
tcctaaccccc tccgcggctt cgcagtacag ttactaatct cacaccgaag aggctctcgc   1740
gccaccctcc gatcccgagc acgttcctta catgccacag cgtcagaatt gaacacaatg   1800
cacgtcarat cagatccccg ggaattcgta atcatggtca tagctgtttc ctgtgtgaaa   1860
ttgttatccg ctcacaattc cacacaacat acgagccgga agcataaagt gtaaagcctg   1920
gggtgcctaa tgagtgagct aactcacatt aattgcgttg cgctcactgc ccgctttcca   1980
gtcgggaaac ctgtcgtgcc agctgcatta atgaatcggc caacgcgcgg ggagaggcgg   2040
tttgcgtatt gggcgctctt ccgcttcctc gctcactgac tcgctgcgct cggtcgttcg   2100
gctgcggcga gcggtatcag ctcactcaaa ggcggtaata cggttatcca cagaatcagg   2160
ggataacgca ggaaagaaca tgtgagcaaa aggccagcaa aaggccagga accgtaaaaa   2220
ggccgcgttg ctggcgtttt tccataggct ccgcccccct gacgagcatc acaaaaatcg   2280
acgctcaagt cagaggtggc gaaacccgac aggactataa agataccagg cgtttccccc   2340
tggaagctcc ctcgtgcgct ctcctgttcc gaccctgccg cttaccggat acctgtccgc   2400
cttctccct tcgggaagcg tggcgctttc tcatagctca cgctgtaggt atctcagttc   2460
ggtgtaggtc gttcgctcca agctgggctg tgtgcacgaa ccccccgttc agcccgaccg   2520
ctgcgcctta tccggtaact atcgtcttga gtccaacccg gtaagacacg acttatcgcc   2580
actggcagca gccactggta acaggattag cagagcgagg tatgtaggcg gtgctacaga   2640
gttcttgaag tggtggccta actacggcta cactagaagg acagtatttg gtatctgcgc   2700
tctgctgaag ccagttacct tcggaaaaag agttggtagc tcttgatccg gcaaacaaac   2760
caccgctggt agcggtggtt tttttgtttg caagcagcag attacgcgca gaaaaaaagg   2820
atctcaagaa gatcctttga tcttttctac ggggtctgac gctcagtgga acgaaaactc   2880
acgttaaggg attttggtca tgagattatc aaaaaggatc ttcacctaga tccttttaaa   2940
ttaaaaatga agttttaaat caatctaaag tatatatgag taaacttggt ctgacagtta   3000
ccaatgctta atcagtgagg cacctatctc agcgatctgt ctatttcgtt catccatagt   3060
tgcctgactc cccgtcgtgt agataactac gatacgggag ggcttaccat ctggccccag   3120
tgctgcaatg ataccgcgag acccacgctc accggctcca gatttatcag caataaacca   3180
gccagccgga agggccgagc gcagaagtgg tcctgcaact ttatccgcct ccatccagtc   3240
tattaattgt tgccgggaag ctagagtaag tagttcgcca gttaatagtt tgcgcaacgt   3300
tgttgccatt gctacaggca tcgtggtgtc acgctcgtcg tttggtatgg cttcattcag   3360
ctccggttcc caacgatcaa ggcgagttac atgatccccc atgttgtgca aaaaagcggt   3420
tagctccttc ggtcctccga tcgttgtcag aagtaagttg gccgcagtgt tatcactcat   3480
```

```
ggttatggca gcactgcata attctcttac tgtcatgcca tccgtaagat gcttttctgt   3540
gactggtgag tactcaacca agtcattctg agaatagtgt atgcggcgac cgagttgctc   3600
ttgcccggcg tcaatacggg ataataccgc gccacatagc agaactttaa aagtgctcat   3660
cattggaaaa cgttcttcgg ggcgaaaact ctcaaggatc ttaccgctgt tgagatccag   3720
ttcgatgtaa cccactcgtg cacccaactg atcttcagca tcttttactt tcaccagcgt   3780
ttctgggtga gcaaaaacag gaaggcaaaa tgccgcaaaa aagggaataa gggcgacacg   3840
gaaatgttga atactcatac tcttcctttt tcaatattat tgaagcattt atcagggtta   3900
ttgtctcatg agcggataca tatttgaatg tatttagaaa aataaacaaa tagggggttcc   3960 gcgcacattt ccccgaaaag tgccacctga cgtctaagaa accattatta tcatgacatt   4020
aacctataaa aataggcgta tcacgaggcc ctttcgtctc gcgcgtttcg gtgatgacgg   4080
tgaaaacctc tgacacatgc agctcccgga cggtcaca gcttgtctgt aagcggatgc   4140
cgggagcaga caagcccgtc agggcgcgtc agcgggtgtt ggcgggtgtc ggggctggct   4200
taactatgcg gcatcagagc agattgtact gagagtgcac catatgcggt gtgaaatacc   4260
gcacagatgc gtaaggagaa ataccgcat caggcgccat cgccattca ggctgcgcaa   4320 ctgttgggaa gggcgatcgg tgcgggcctc ttcgctatta cgccagctgg cgaaaggggg   4380
atgtgctgca aggcgattaa gttgggtaac gccagggttt cccagtcac gacgttgtaa   4440 aacgacggcc agtgccaagc ttgcatgcct gcaggtcgac gaccgagcgc gcgccaccca   4500
gcctatcccg cgcgggtcgg gacccaaaat aagcgggccc cgccgcgccc cgtcgggcga   4560
gcgggtgtat ctacgaacgg aactgggagg cgactcggaa gagtttggtt agaaagggga   4620
acaccatcgc ggacggccca gtgctctggd cagctgagcg tgcattgtgt tcaattctga   4680
cctgtggcat gtaaggaacg tgctcgggat cggagggtgg cgcgagagcc tcttcggtgt   4740
gagattagta actgtactgc gaagccgcgg aggggttagg atgagaggta gacagggtcg   4800
cagcccaggt gcgagaagga ctgcgaagga ctgttcttcg accgcgcacc tgcaattgcg   4860
cgcatggata gaatagagcg tcgccctcga ggggactcg accagggctg gtggtggcgc   4920
ccgacgggac tggctgggca tttgcagatg gcgcgcagtc caggccgccg ccgatgtgtt   4980
catcccgttt tgtcagtatc gatcggatct ttcgggcgtg gtataaaag cgcgccgccc   5040 gccgtctccc tctttctcca gcactcccat ccagagcact tccctctccc atcgcatccc   5100
atcacacaat aatgcccatc ac                                           5122
```

<210> SEQ ID NO 13
<211> LENGTH: 5490
<212> TYPE: DNA
<213> ORGANISM: Artificial Sequence
<220> FEATURE:
<223> OTHER INFORMATION: Description of Artificial Sequence: Synthetic
      vector

<400> SEQUENCE: 13

```
agcttctccg gccccgaatc gaacggcagg atgtgtgggc gtgtccaata ttgccatgaa     60
aatctgtcag aagtgagccc tctcgtcacc ctgtacagct tcgctgagtt gaaaagcagg    120
gttcatcttg ggctcactga tgcactgagc tcgaccggag aactaaatga ccagccggag    180
tgttcactaa cttaacgccg ggtattcagg gcagcttctc tatgttgcgc ctacgacgta    240
gatcaccgcc catgaacggg ggaaacgggg aggggtgcgt ttggtacgtc tttacgtctg    300
gctatgttgt attgaccagc gtctgcagaa gatgggcacg acgatgcgcc gagccggcca    360
```

```
gtgtcgtcgg atgtccactg ttgaggccat ccttttgcta gacagacgga agagctttgg    420
aggtgcgatt cctctacgaa tgggaagggg cttagatgga gagtgacacg tctgagctcc    480
ccaacacgcc ttcgccgagg gtgcgtctcc gcggacattc acctcagttc attgttctga    540
cctgcctaat tgtatagacc ggccaacaac cttgctgacg cccatcataa cagtgccctg    600
cacagagcct tcccactcag tcggcgcctc cctcaatcaa tcccactaac tcgccggctc    660
tgccccttcg ccgctcgaca cgtcgcttgg aagagcccgg gcacgggcgt ccgctccccc    720
cttccctccg cgtcgtcatg cacgcagcgt taatgttgct gcaggcgagc cgtaagtata    780
ttcaaaggcg tagcgaatga atagcaggcg cgcggggacc tggcacgcgc ggcatgaaca    840
tgcagacttg ggtgacgata acttgaactc agacgcggcg aatgaatatc caaacgcgcg    900
ggaagaaaat aatttacggg agcctcccca ggtataaaag cccctcaccc gctcactctt    960
tctccagtcg aacacccag ttcaactacc cagcccttcc ttccttcgct atccttcytt   1020
acaacctgct cgccatggga tatcgcatgc ctgcagagct ctagactcga cgggcccggt   1080
accgcggccg ccttaagacg cgtggatccg caggtgaacg cgcctatcgg tgggatattc   1140
gggcgacggg agcctcggca atctgagcct cgttactgcc tagcaaattc ggaatccctt   1200
cgatgtcata gggtcgcgga caagtgatcg tcttgctaca tactccaagg tgttgactca   1260
ttccctcgat aatgaacatt gttgttgttg tttgttctct atccgctcag tcacgcgacc   1320
ccacacgtgc atggttgaac ttcgccacgc aacaaccgca tgacgacatg gcgaacctaa   1380
gtaaaggctg agtcgtggac taaagcactc cactttacgg cgaggatgcc agtctacgtc   1440
atgaatgaag cctcaggtcc cgaagtaagg gggtacaaaa ggagggtgaa aggtggacgt   1500
tttcttacca tccttccacc tcccagacca ccatgccggg aattcccagc ttgctcaaaa   1560
aggttctgcc cgtacgcccg cgaaattcct tcgaggtggc ccctatcgca tacatgcacg   1620
acttcaaaac atccattcta tcattttggg atcgtacaat tattagacat gttgtacaac   1680
gttacattcc tttcttcttt tactctccgg cccagtctat gtagaggtaa agtacaagcg   1740
tccaaaggat caggcactta gagcgcgccg tcttgcttcg ccgcttagag cgcgccgtcc   1800
tgcttcgccg cgtagacgag caggtcgcag acacggcggg agtagcccca ctcgttgtcg   1860
taccaggcaa tgagcttcac gaagctcttg ctgatcgcga tgccggggat cgatccacgc   1920
gtcttaaggc ggccgcggta ccccctcgga cccgtcgggc cgcgtcggac cggcggtgtt   1980
ggtcggcgtc ggtcagtcct gctcctcggc cacgaagtgc acgcagttgc cggccgggtc   2040
gcgcagggcg aactcccgcc cccacggctg ctcgccgatc tcggtcatgg ccggcccgga   2100
ggcgtcccgg aagttcgtgg acacgacctc cgaccactcg gcgtacagct cgtccaggcc   2160
gcgcacccac acccaggcca gggtgttgtc cggcaccacc tggtcctgga ccgcgctgat   2220
gaacagggtc acgtcgtccc ggaccacacc ggcgaagtcg tcctccacga agtcccggga   2280
gaacccgagc cggtcggtcc agaactcgac cgctccggcg acgtcgcgcg cggtgagcac   2340
cggaacggca ctggtcaact ggccatgca tggtgatggg cattatgtgt gatgggatgc   2400
gatgggagag ggaagtgctc tggatgggag tgctggagaa agaggagac ggcgggcggc   2460
gcgccttttta taccacgcc cgaaagatcc gatcgatact gacaaaacgg gatgaacaca   2520
tcggcggcgg cctggactgc gcgccatctg caaatgccca gccagtcccg tcggcgcca    2580
ccaccagccc tggtcgagtc cccctcgagg gcgacgctct attctatcca tgcgcgcaat   2640
tgcaggtgcg cggtcgaaga acagtccttc gcagtcctte tcgcacctgg gctgcgaccc   2700
tgtctacctc tcatcctaac ccctccgcgg cttcgcagta cagttactaa tctcacaccg   2760
```

```
aagaggctct cgcgccaccc tccgatcccg agcacgttcc ttacatgcca cagcgtcaga    2820
attgaacaca atgcacgtca ratcagatcc ccgggaattc gtaatcatgg tcatagctgt    2880
ttcctgtgtg aaattgttat ccgctcacaa ttccacacaa catacgagcc ggaagcataa    2940
agtgtaaagc ctggggtgcc taatgagtga gctaactcac attaattgcg ttgcgctcac    3000
tgcccgcttt ccagtcggga aacctgtcgt gccagctgca ttaatgaatc ggccaacgcg    3060
cggggagagg cggtttgcgt attgggcgct cttccgcttc ctcgctcact gactcgctgc    3120
gctcggtcgt tcggctgcgg cgagcggtat cagctcactc aaaggcggta atacggttat    3180
ccacagaatc aggggataac gcaggaaaga acatgtgagc aaaaggccag caaaaggcca    3240
ggaaccgtaa aaaggccgcg ttgctggcgt ttttccatag gctccgcccc cctgacgagc    3300
atcacaaaaa tcgacgctca agtcagaggt ggcgaaaccc gacaggacta taaagatacc    3360
aggcgtttcc ccctggaagc tccctcgtgc gctctcctgt tccgaccctg ccgcttaccg    3420
gatacctgtc cgcctttctc ccttcgggaa gcgtggcgct ttctcatagc tcacgctgta    3480
ggtatctcag ttcggtgtag gtcgttcgct ccaagctggg ctgtgtgcac gaaccccccg    3540
ttcagcccga ccgctgcgcc ttatccggta actatcgtct tgagtccaac ccggtaagac    3600
acgacttatc gccactggca gcagccactg gtaacaggat tagcagagcg aggtatgtag    3660
gcggtgctac agagttcttg aagtggtggc ctaactacgg ctacactaga aggacagtat    3720
ttggtatctg cgctctgctg aagccagtta ccttcggaaa aagagttggt agctcttgat    3780
ccggcaaaca aaccaccgct ggtagcggtg gtttttttgt ttgcaagcag cagattacgc    3840
gcagaaaaaa aggatctcaa gaagatcctt tgatcttttc tacggggtct gacgctcagt    3900
ggaacgaaaa ctcacgttaa gggattttgg tcatgagatt atcaaaaagg atcttcacct    3960
agatcctttt aaattaaaaa tgaagtttta aatcaatcta agtatatat gagtaaactt    4020
ggtctgacag ttaccaatgc ttaatcagtg aggcacctat ctcagcgatc tgtctatttc    4080
gttcatccat agttgcctga ctccccgtcg tgtagataac tacgatacgg gagggcttac    4140
catctggccc cagtgctgca atgataccgc gagacccacg ctcaccggct ccagatttat    4200
cagcaataaa ccagccagcc ggaagggccg agcgcagaag tggtcctgca actttatccg    4260
cctccatcca gtctattaat tgttgccggg aagctagagt aagtagttcg ccagttaata    4320
gtttgcgcaa cgttgttgcc attgctacag gcatcgtggt gtcacgctcg tcgtttggta    4380
tggcttcatt cagctccggt tcccaacgat caaggcgagt tacatgatcc cccatgttgt    4440
gcaaaaaagc ggttagctcc ttcggtcctc cgatcgttgt cagaagtaag ttggccgcag    4500
tgttatcact catggttatg gcagcactgc ataattctct tactgtcatg ccatccgtaa    4560
gatgcttttc tgtgactggt gagtactcaa ccaagtcatt ctgagaatag tgtatgcggc    4620
gaccgagttg ctcttgcccg gcgtcaatac gggataatac cgcgccacat agcagaactt    4680
taaaagtgct catcattgga aaacgttctt cggggcgaaa actctcaagg atcttaccgc    4740
tgttgagatc cagttcgatg taacccactc gtgcacccaa ctgatcttca gcatctttta    4800
ctttcaccag cgtttctggg tgagcaaaaa caggaaggca aaatgccgca aaaaagggaa    4860
taagggcgac acggaaatgt tgaatactca tactcttcct ttttcaatat tattgaagca    4920
tttatcaggg ttattgtctc atgagcggat acatatttga atgtatttag aaaaataaac    4980
aaataggggt tccgcgcaca tttccccgaa aagtgccacc tgacgtctaa gaaaccatta    5040
ttatcatgac attaacctat aaaaataggc gtatcacgag gccctttcgt ctcgcgcgtt    5100
tcggtgatga cggtgaaaac ctctgacaca tgcagctccc ggagacggtc acagcttgtc    5160
```

```
tgtaagcgga tgccgggagc agacaagccc gtcagggcgc gtcagcgggt gttggcgggt    5220 gtcgggctg gcttaactat gcggcatcag agcagattgt actgagagtg caccatatgc    5280
ggtgtgaaat accgcacaga tgcgtaagga gaaaataccg catcaggcgc cattcgccat    5340
tcaggctgcg caactgttgg gaagggcgat cggtgcgggc ctcttcgcta ttacgccagc    5400
tggcgaaagg gggatgtgct gcaaggcgat taagttgggt aacgccaggg ttttcccagt    5460
cacgacgttg taaaacgacg gccagtgcca                                    5490

<210> SEQ ID NO 14
<211> LENGTH: 6983
<212> TYPE: DNA
<213> ORGANISM: Artificial Sequence
<220> FEATURE:
<223> OTHER INFORMATION: Description of Artificial Sequence: Synthetic
      vector

<400> SEQUENCE: 14
catgggatat cgcatgcctg cagagctcta gagtcgacgg gcccggtacc gcggccgcct      60
taagacgcgt ggatccgcag gtgaacgcgc ctatcggtgg gatattcggg cgacgggagc    120
ctcggcaatc tgagcctcgt tactgcctag caaattcgga atcccttcga tgtcataggg    180
tcgcggacaa gtgatcgtct tgctacatac tccaaggtgt tgactcattc cctcgataat    240
gaacattgtt gttgttgttt gttctctatc cgctcagtca cgcgacccca cacgtgcatg    300
gttgaacttc gccacgcaac aaccgcatga cgacatggcg aacctaagta aaggctgagt    360
cgtggactaa agcactccac tttacggcga ggatgccagt ctacgtcatg aatgaagcct    420
caggtcccga agtaagggggg tacaaaagga gggtgaaagg tggacgtttt cttaccatcc    480
ttccacctcc cagaccacca tgccgggaat cccagcttg ctcaaaaagg ttctgcccgt    540
acgcccgcga aattccttcg aggtggcccc tatcgcatac atgcacgact tcaaaacatc    600
cattctatca ttttgggatc gtacaattat tagacatgtt gtacaacgtt acattccttt    660 cttctttttac tctccggccc agtctatgta gaggtaaagt acaagcgtcc aaaggatcag    720
gcacttagag cgcgccgtct tgcttcgccg cttagagcgc gccgtcctgc ttcgccgcgt    780
agacgagcag gtcgcagaca cggcgggagt agccccactc gttgtcgtac caggcaatga    840
gcttcacgaa gctcttgctg atcgcgatgc cgggatcga tccacgcgtc ttaaggcggc    900
cgcggtaccc cctcggaccc gtcgggccgc gtcggaccgg cggtgttggt cggcgtcggt    960
cagtcctgct cctcggccac gaagtgcacg cagttgccgg ccgggtcgcg cagggcgaac   1020
tcccgccccc acggctgctc gccgatctcg gtcatggccg gccggaggc gtcccggaag   1080 ttcgtggaca cgacctccga ccactcggc tacagctcgt ccaggccgcg cacccacacc   1140
caggccaggg tgttgtccgg caccacctgg tcctggaccg cgctgatgaa cagggtcacg   1200
tcgtcccgga ccacaccggc gaagtcgtcc tccacgaagt cccgggagaa cccgagccgg   1260
tcggtccaga actcgaccgc tccggcgacg tcgcgcgcgg tgagcaccgg aacggcactg   1320
gtcaacttgg ccatgcatgg tgatgggcat tatgtgtgat gggatgcgat gggagaggga   1380
agtgctctgg atgggagtgc tggagaaaga gggagacggc gggcggcgcg ccttttatac   1440
ccacgcccga agatccgat cgatactgac aaaacgggat gaacacatcg gcggcggcct   1500
ggactgcgcg ccatctgcaa atgcccagcc agtcccgtcg ggcgccacca ccagccctgg   1560
tcgagtcccc ctcgagggcg acgctctatt ctatccatgc gcgcaattgc aggtgcgcgg   1620
tcgaagaaca gtccttcgca gtccttctcg cacctgggct gcgaccctgt ctacctctca   1680 tcctaaccccc tccgcggctt cgcagtacag ttactaatct cacaccgaag aggctctcgc   1740
```

```
gccaccctcc gatcccgagc acgttcctta catgccacag cgtcagaatt gaacacaatg    1800
cacgtcarat cagatccccg ggaattcgta atcatggtca tagctgtttc ctgtgtgaaa    1860
ttgttatccg ctcacaattc cacacaacat acgagccgga agcataaagt gtaaagcctg    1920
gggtgcctaa tgagtgagct aactcacatt aattgcgttg cgctcactgc ccgctttcca    1980
gtcgggaaac ctgtcgtgcc agctgcatta atgaatcggc caacgcgcgg ggagaggcgg    2040
tttgcgtatt gggcgctctt ccgcttcctc gctcactgac tcgctgcgct cggtcgttcg    2100
gctgcggcga gcggtatcag ctcactcaaa ggcggtaata cggttatcca cagaatcagg    2160
ggataacgca ggaaagaaca tgtgagcaaa aggccagcaa aaggccagga accgtaaaaa    2220
ggccgcgttg ctggcgtttt tccataggct ccgcccccct gacgagcatc acaaaaatcg    2280
acgctcaagt cagaggtggc gaaacccgac aggactataa agataccagg cgtttccccc    2340
tggaagctcc ctcgtgcgct ctcctgttcc gaccctgccg cttaccggat acctgtccgc    2400
ctttctccct tcgggaagcg tggcgctttc tcatagctca cgctgtaggt atctcagttc    2460
ggtgtaggtc gttcgctcca agctgggctg tgtgcacgaa ccccccgttc agcccgaccg    2520
ctgcgcctta tccggtaact atcgtcttga gtccaacccg gtaagacacg acttatcgcc    2580
actggcagca gccactggta acaggattag cagagcgagg tatgtaggcg gtgctacaga    2640
gttcttgaag tggtggccta actacggcta cactagaagg acagtatttg gtatctgcgc    2700
tctgctgaag ccagttacct tcggaaaaag agttggtagc tcttgatccg gcaaacaaac    2760
caccgctggt agcggtggtt tttttgtttg caagcagcag attacgcgca gaaaaaaagg    2820
atctcaagaa gatcctttga tcttttctac ggggtctgac gctcagtgga acgaaaactc    2880
acgttaaggg attttggtca tgagattatc aaaaaggatc ttcacctaga tccttttaaa    2940
ttaaaaatga agttttaaat caatctaaag tatatatgag taaacttggt ctgacagtta    3000
ccaatgctta atcagtgagg cacctatctc agcgatctgt ctatttcgtt catccatagt    3060
tgcctgactc cccgtcgtgt agataactac gatacgggag ggcttaccat ctggccccag    3120
tgctgcaatg ataccgcgag acccacgctc accggctcca gatttatcag caataaacca    3180
gccagccgga agggccgagc gcagaagtgg tcctgcaact ttatccgcct ccatccagtc    3240
tattaattgt tgccgggaag ctagagtaag tagttcgcca gttaatagtt tgcgcaacgt    3300
tgttgccatt gctacaggca tcgtggtgtc acgctcgtcg tttggtatgg cttcattcag    3360
ctccggttcc caacgatcaa ggcgagttac atgatccccc atgttgtgca aaaaagcggt    3420
tagctccttc ggtcctccga tcgttgtcag aagtaagttg gccgcagtgt tatcactcat    3480
ggttatggca gcactgcata attctcttac tgtcatgcca tccgtaagat gcttttctgt    3540
gactggtgag tactcaacca agtcattctg agaatagtgt atgcggcgac cgagttgctc    3600
ttgcccggcg tcaatacggg ataataccgc gccacatagc agaactttaa aagtgctcat    3660
cattggaaaa cgttcttcgg ggcgaaaact ctcaaggatc ttaccgctgt tgagatccag    3720
ttcgatgtaa cccactcgtg cacccaactg atcttcagca tcttttactt tcaccagcgt    3780
ttctgggtga gcaaaaacag gaaggcaaaa tgccgcaaaa aagggaataa gggcgacacg    3840
gaaatgttga atactcatac tcttcctttt tcaatattat tgaagcattt atcagggtta    3900
ttgtctcatg agcggataca tatttgaatg tatttagaaa aataaacaaa taggggttcc    3960
gcgcacattt ccccgaaaag tgccacctga cgtctaagaa accattatta tcatgacatt    4020
aacctataaa aataggcgta tcacgaggcc ctttcgtctc gcgcgtttcg gtgatgacgg    4080
tgaaaacctc tgacacatgc agctcccgga gacggtcaca gcttgtctgt aagcggatgc    4140
```

```
cgggagcaga caagcccgtc agggcgcgtc agcgggtgtt ggcgggtgtc ggggctggct    4200
taactatgcg gcatcagagc agattgtact gagagtgcac catatgcggt gtgaaatacc    4260
gcacagatgc gtaaggagaa ataccgcat caggcgccat tcgccattca ggctgcgcaa    4320
ctgttgggaa gggcgatcgg tgcgggcctc ttcgctatta cgccagctgg cgaaaggggg    4380
atgtgctgca aggcgattaa gttgggtaac gccagggttt tcccagtcac gacgttgtaa    4440
aacgacggcc agtgccaagc ttagatctcc gaaccagaaa tgcgattgcg ttcaggccca    4500
attaagaata aagctgcgtc agggcagcga cgtatcttga tccatcattg actcaccggc    4560
atcggcgtca acaccaaagc aagctcgtcc cacccatagg cgtgcaccgg ccggcgtgcg    4620
ccattgaggt acatgagcgg ggcgaaagtc cgccattggt agccctgtcg tggacgcgcg    4680
gcgatgaaac gtttcccacc attgggaaga aacgtctgcg gcccatcatc ccttcaccgg    4740
atgacaaggc ggcgtcgcgc ctttgccgca gaggccggcg ggcgacatgc acagcgaagg    4800
tccgttgcgg atgggaagca ggcaatcagt gggtgtccta cgccgccacg atggtcgggg    4860
agcgtaggcg ccctcccata aggcggcaag catcatgatg ctctccgatt cgggaagcct    4920
ggtgcgatgc tggagagact ctctccgaga gaccagtgtg cgcaacgttc ctggcctgga    4980
agactttaaa gtgagtgtag aagggcgagc agaggacgat catcggattg caggaaccat    5040
cggcatcctc agcctgggaa ggatggctct tggtagacat tcgcggaagg tgtcctagat    5100
gtgagcgggc ttcttggatg atcatgtcgt aacttttctc gacctcgtcg gtggtacgca    5160
tggcaggatt gagcattacg gtatgcctcc cattcataaa cgataacccc ttccttcagg    5220
ttggtcatct ccatagagcg gcacgctctc aaggcctagg ctattcacac ctccttcgca    5280
acatccctat tcacggtgtc tgtaaggaac gacttgtcat gggatcacat gaagtgcagc    5340
atactgttcg ccggtctcgc agtacagacg ctagtacggg aagtcgacat ccaagcgttc    5400
agtcaccaca tggcaaaaaa gctgcaccat actctttatg gtgagttgtt cgtgagtggt    5460
atacagtcat tcatgaggga atgcccaccg gatagggtgt ggcggccgca atattcatcg    5520
cctggcaata gtcgatgtgc gtccttgttc aatgaatatc atgggtcaca tgtgagacg    5580 gttaaacagc gttgactgtg aatccctggt gtgtgttggg ccgaacaggt acgttgcagg    5640
aacaccaata tctcttcggc agcccagttc tttgcgagcg gcacaggcag gcatcgcgca    5700
acagatccca gccatccggc tctgacatt cgggatacct gaagcccttc aggtacggag    5760
cgaagaggtg ggctctctgc agcgattggc ggacggatag ctgtatttcc tctctcacca    5820
ttgggaagat gtgaaaggct ccatcatata gcggctcaac tctacctcga atgtccaaac    5880
acggcgggaa tacttattta tgtggacaag gccgagctat gatagcttgc tcccgaagtt    5940
ggtaagtccc gcaatctgcg gttcaggcaa cagtctcgga aaaataagaa gaatattgta    6000
ggtgcgtgta ggcgtatcgc ccaaatgcgc acacacggag gctttaggag atgaagcgcc    6060
cgtgagcggt aagggagttg gttcaccgcc gccccgaccg actctctctc tttcccagca    6120
tcatgtctcg gcgcaaactt taccctctat tgaccaactc cacgagaaag caggaacagc    6180
ttccttgtct ctcatgacgt ccgcaatcca gacccttagc cggttcgtta ctcatcgtta    6240
tccctgccgc catcgtagtg gagtcagcct ggccagtgcg tagtcccgtc tctcttgctg    6300
cactagagaa gccccatgag acagcgtttt ttgctttatt tctgctgttt ctatagacac    6360
cataggggca aacgatcctg cacgcccaga ggtattgggc tcgtcagatt cccagttttt    6420
ctcctcggtc tgaatcggct gcacggcaga taaatcggcc ggaaatgcta tagcccttca    6480
tagcccgcta tgagagtcgc aaaaggcttg tcagtcaggt cggtcgagtg gctctcacga    6540
```

```
agagcgtcaa cttcgcgcga cagccgcctt tcagggcaag atagatcctc ccatcatccc    6600
ctactgcgct cagcgccggt accgaacaat tgacttaccg acatcctccg ggacgcgcaa    6660
atgctgttcg acggaacgta atcctcttcg tcccgcctct tttcgctctc acgcattccg    6720
tgtggttcgc gcgacggccg ctcatcagga ccagaccagt ctcaatgtct ggtaccggca    6780
caatggtgac actgcggcaa ctgagtaggt ctggtcactc tggtgcaccg tcgcttacgc    6840
tgaccttcgg gatactgtcc tgcagacatc tggagcgcct gtctttcccc tagtataaat    6900
gatgtctgtc cgcaggtcct tgaagaccgc tcgagtccca cttgagtttt aggtaggacc    6960
tgttcctcca caaccctct ttc                                              6983

<210> SEQ ID NO 15
<211> LENGTH: 4395
<212> TYPE: DNA
<213> ORGANISM: Pycnoporus cinnabarinus

<400> SEQUENCE: 15
gagcttactg gatcttccag agaaatcgtt ggagaggtcg gccggtcagc ctcaccgaca      60
tttgacgtgg ccgatgattc tgtggatgcc atcgtgttgg atcctgagct tgcatccatc     120
gccaagcgcg tcaaagctga ggtgggaagg cagggaggca caccagttcc cgaaggaggc     180
ggacctgaga ttgtgacgct caagattata tggaaacctc atccgctgaa ccccaacggc     240
cgtccggaac tctgggctat gaagcagaga cgggtaggtg aagtcgctca tcacgcctcg     300
ttcttactca ccatcttctg cagcacgaga atttccaccg gctttgttcc gaagtagcgg     360
acctcgcgag tgttcgtagt gagaacgtcg tgctttccct cgacgggaaa cgcgtgttcc     420
cttcatctac ccctcacagt gtcggtgtct gggcagaagc tgagctaggt tagtgactta     480
tcctgtgcgt gacggcacga tgcttactct tcaacagaag cttgtgacaa gatcacctac     540
caatacctgc aggaaaataa gcgaatgcgt tccgaatccg ttgctccgcc aacccatcct     600
cacctcgacg acatttcccg tcagtctcca actcgcgcgc gctccccttc catcaccgag     660
ctgtccgaga atgaatccgg cgctgcagag tctggtcctg aagataaggg cacaagcact     720
ggggaggcct tcagcctgat actcgtgagc gaacggacca agggcaagcg aataaccctc     780
cgtgtgctcc caaccaccaa atgtggcgtc atagttcgca agttcctaga gaaggccggc     840
ttacaggacg aataccccga tgtcacccct tgctgcgaatg ggcgaggacg cacgaagacg     900
tcagccaaga caccggcgct gagcgtcgat ggagataaga tggatccgga ggcacctatt     960
ggtgatgccg acctggaaga tggggatcaa gtcgaggtgg ttggtctttg atgtagcgag    1020
tgcgtggtgt tacgttttcg tcttgctatc ggttttctg ctcttgtctt gttagtaagt    1080
agtataatga tggataatca cacaacaacg tatgtgttcc agggacttct ctctcagtgg    1140
gtgtgtggct gattgtacga acatcgcac aggcctttca ccgctgctcc tagcgcgaga    1200
ccacatgaac gccctcgcac gtcagtcggc ctcgcgaacg atagggcagt gccaaatgca    1260
ggcgaaaatg actcagttag gccacgcctg cgctttaact ttagcgttct aataccctcg    1320
acctccgtag cggtcctgtg agcgcggaaa gcttggcatc tacgctcttt gtccggtccg    1380
aagccactac attgagcggt tcgccccggc ggtgacaaac tgcgaggcgc aagaatgtag    1440
ccgggcctgc ggaaaggtca tgaacaaact atgtcggccc caaccagtgc taccgacacc    1500
gttctccgtg tttcagtatg ccttcagctg tcggtgggcg gggtggctcc gatatgtgta    1560
ctcggaaacg ctcacagcgc tctttgtatt gccgggtatg tgaccaacgg tgccctcatg    1620
ctcttcgctt gttgatgctc cttcaggaca ccgtctggga ctctggcaag tcagctgctg    1680
```

```
ctcgccacag ttctaggaac gtctcaatgc tcctaggcgg cggttacagc aaacgccttg   1740
caccgggatg ggcctcggta cgccgcacag gcgaggctgt cctactcggc gttcgttagt   1800 agcccccat ccacgtaaga gtacctcctg cagccaccat cgtctactag cgtaccaccc    1860
acgtccactc acatcatatg ccgcccgacg cccccggact gattccgcgc tattgttgag   1920
atataagagg agtgttcgaa cggaccaagg agccataatc ccctcgagca tttcgagatc   1980
ctctccccac tgaactcctt cgccgtcacc acaaaacctc gcgtagatgt cacacttcat   2040
cgttactggg cctgtaggag gtcagactga gggcgctcct gctcccaacc gcctcgaaat   2100
caacgacttc gtcaagaatg aggagttctt ctcgctttac gtccaggctc tcggtgcgtc   2160
gccttggcac atgtatgctc acccctatta ccatgaagct catgagccct cactacatac   2220
agatatcatg tatggactga agcaggagga actgatctcg ttcttccaga tcggtggcat   2280
tcatggattg ccatacgttg cctggagtga tgccggagcg gatgaccctg ctgagccgtc   2340
cgggtactgt acccatggct ccgtactgtt cccgacctgg cataggcctt acgtcgcact   2400
atatgaggta agcagcttgc tagatcagac cgctacggac gacgctgaga ctcaaaatgg   2460
ctacagcaaa tcttgcacaa gtatgctgga gagatcgctg ataagtacac ggtcgacaaa   2520
ccgcgttggc agaaggcagc ggccgacctg cgccaaccct tctgggactg gccaagaac    2580 acgctgcctc ctcctgaagt catctctctc gacaaagtca cgattacgac accagatgga   2640
cagaggacgc aagttgacaa tccactccgt cgctaccgct tccatccgat cgaccccagc   2700
ttcccagagc catacagcaa ctggccagcg acactgagac atccgacaag tgatggctcg   2760
gatgccaaag acaacgtgaa ggatctcact acgtaagcca attcgccata aagacgctcc   2820
tccattcatc tcaatgtata tatgtgacag tactctgaag gcggaccagc ctgatatcac   2880
gacgaagacg tataatctat tgaccagagt gcacacgtgg ccggcgttca gcaaccacac   2940
tccaggcgat ggcggcagct ccagtaacag tcttgaggcc attcacgacc acatccatga   3000
ctcagttggc ggcggaggcc agatgggaga cccgtccgtg gcaggtatgt gaagtgattc   3060
ttcgcgagag acgtgactta catgtccttg taggcttcga cccaatcttc ttcctgcacc   3120
attgccaagt tgatcgtctt cttgcactgt ggtccgcctt gaaccccggc gtgtgggtca   3180
acagctctag ctccgaagat ggcacctaca cgatcccgcc tgactctacc gtggaccaaa   3240
ctactggtgg gttcccgcac agctgtgcgc tgtggagtcg ccgttgactt ccatcactct   3300
cagcattgac gcccttctgg gatacccaaa gcacattctg gacgtccttc cagtctgctg   3360
gagtctcgcc cagccaattt ggctattctt accccgagtt taacggtctc aacctgcaag   3420
atcagaaggc tgtgaaagat cacatcgccg aggtcgtgaa cgagctctac ggtcatcgca   3480
tgcggaaaac cttcccttc ccccagctcc aggcagtttc cgtagccaag cagggcgacg    3540
ccgtcactcc atccgtggct accgattcag tgtcgtcttc taccacacct gccgaaaatc   3600
ccgcatcccg cgaggatgcc tctgataagg acacagagcc gacgctcaat gtagaggttg   3660
ccgcgccagg cgcgcacttg acctccacca agtattggga ctggactgct cgcattcatg   3720
tcaagaagta cgaagtcgga ggcagcttca gcgtcctgct cttcctgggt gcaatccccg   3780
agaacccagc ggattggcgc acgagcccca actacgttgg cggtcatcat gctttcgtga   3840
atagctcacc gcagcgctgc gctaactgcc gtggtcaagg cgaccttgtc atcgaaggct   3900
tcgtccatct caacgaggcg atcgcccgcc atgcgcacct cgactccttc gatccaaccg   3960
tcgtgaggcc gtacctcacg cgcgagttgc actggggtgt gatgaaggtc agtgcctaca   4020
ctctgcatac gaccgtatat gtcgctaatt agatctatca aggtgaatgg caccgtcgtg   4080
```

-continued

```
cccctgcaag acgtcccgtc gctcgaggtt gtcgtcctct caactcctct taccctccct    4140
ccgggagagc cattccctgt ccccggaacg cccgtcaatc atcatgacat cacccatgga    4200
cgtcctggtg gctctcacca cacgcactaa gcatgctgat ggcctgcccc tattgattaa    4260
acacgagtcg acctgagaac acatacaatg gatgtaatca tacttcactt ttgatgacaa    4320
tcgcttccac attctgttcc tagcgggaca gataacccag tcaaaaaaaa aaaaaaaaa    4380 aaaacactgt catgc                                                    4395
```

<210> SEQ ID NO 16
<211> LENGTH: 618
<212> TYPE: PRT
<213> ORGANISM: Pycnoporus cinnabarinus

<400> SEQUENCE: 16

```
Met Ser His Phe Ile Val Thr Gly Pro Val Gly Gln Thr Glu Gly
1               5                   10                  15

Ala Pro Ala Pro Asn Arg Leu Glu Ile Asn Asp Phe Val Lys Asn Glu
            20                  25                  30

Glu Phe Phe Ser Leu Tyr Val Gln Ala Leu Asp Ile Met Tyr Gly Leu
        35                  40                  45

Lys Gln Glu Glu Leu Ile Ser Phe Phe Gln Ile Gly Gly Ile His Gly
    50                  55                  60

Leu Pro Tyr Val Ala Trp Ser Asp Ala Gly Ala Asp Pro Ala Glu
65                  70                  75                  80

Pro Ser Gly Tyr Cys Thr His Gly Ser Val Leu Phe Pro Thr Trp His
                85                  90                  95

Arg Pro Tyr Val Ala Leu Tyr Glu Gln Ile Leu His Lys Tyr Ala Gly
            100                 105                 110

Glu Ile Ala Asp Lys Tyr Thr Val Asp Lys Pro Arg Trp Gln Lys Ala
        115                 120                 125

Ala Ala Asp Leu Arg Gln Pro Phe Trp Asp Trp Ala Lys Asn Thr Leu
    130                 135                 140

Pro Pro Pro Glu Val Ile Ser Leu Asp Lys Val Thr Ile Thr Thr Pro
145                 150                 155                 160

Asp Gly Gln Arg Thr Gln Val Asp Asn Pro Leu Arg Arg Tyr Arg Phe
                165                 170                 175

His Pro Ile Asp Pro Ser Phe Pro Glu Pro Tyr Ser Asn Trp Pro Ala
            180                 185                 190

Thr Leu Arg His Pro Thr Ser Asp Gly Ser Asp Ala Lys Asp Asn Val
        195                 200                 205

Lys Asp Leu Thr Thr Thr Leu Lys Ala Asp Gln Pro Asp Ile Thr Thr
    210                 215                 220

Lys Thr Tyr Asn Leu Leu Thr Arg Val His Thr Trp Pro Ala Phe Ser
225                 230                 235                 240

Asn His Thr Pro Gly Asp Gly Ser Ser Asn Ser Leu Glu Ala
                245                 250                 255

Ile His Asp His Ile His Asp Ser Val Gly Gly Gly Gln Met Gly
            260                 265                 270

Asp Pro Ser Val Ala Gly Phe Asp Pro Ile Phe Phe Leu His His Cys
        275                 280                 285

Gln Val Asp Arg Leu Leu Ala Leu Trp Ser Ala Leu Asn Pro Gly Val
    290                 295                 300

Trp Val Asn Ser Ser Ser Ser Glu Asp Gly Thr Tyr Thr Ile Pro Pro
305                 310                 315                 320
```

```
Asp Ser Thr Val Asp Gln Thr Ala Leu Thr Pro Phe Trp Asp Thr
            325                 330                 335

Gln Ser Thr Phe Trp Thr Ser Phe Gln Ser Ala Gly Val Ser Pro Ser
        340                 345                 350

Gln Phe Gly Tyr Ser Tyr Pro Glu Phe Asn Gly Leu Asn Leu Gln Asp
            355                 360                 365

Gln Lys Ala Val Lys Asp His Ile Ala Glu Val Val Asn Glu Leu Tyr
    370                 375                 380

Gly His Arg Met Arg Lys Thr Phe Pro Phe Pro Gln Leu Gln Ala Val
385                 390                 395                 400

Ser Val Ala Lys Gln Gly Asp Ala Val Thr Pro Ser Val Ala Thr Asp
                405                 410                 415

Ser Val Ser Ser Thr Thr Pro Ala Glu Asn Pro Ala Ser Arg Glu
            420                 425                 430

Asp Ala Ser Asp Lys Asp Thr Glu Pro Thr Leu Asn Val Glu Val Ala
    435                 440                 445

Ala Pro Gly Ala His Leu Thr Ser Thr Lys Tyr Trp Asp Trp Thr Ala
    450                 455                 460

Arg Ile His Val Lys Lys Tyr Glu Val Gly Gly Ser Phe Ser Val Leu
465                 470                 475                 480

Leu Phe Leu Gly Ala Ile Pro Glu Asn Pro Ala Asp Trp Arg Thr Ser
                485                 490                 495

Pro Asn Tyr Val Gly Gly His Ala Phe Val Asn Ser Ser Pro Gln
            500                 505                 510

Arg Cys Ala Asn Cys Arg Gly Gln Gly Asp Leu Val Ile Glu Gly Phe
    515                 520                 525

Val His Leu Asn Glu Ala Ile Ala Arg His Ala His Leu Asp Ser Phe
    530                 535                 540

Asp Pro Thr Val Val Arg Pro Tyr Leu Thr Arg Glu Leu His Trp Gly
545                 550                 555                 560

Val Met Lys Val Asn Gly Thr Val Pro Leu Gln Asp Val Pro Ser
                565                 570                 575

Leu Glu Val Val Val Leu Ser Thr Pro Leu Thr Leu Pro Pro Gly Glu
            580                 585                 590

Pro Phe Pro Val Pro Gly Thr Pro Val Asn His His Asp Ile Thr His
        595                 600                 605

Gly Arg Pro Gly Gly Ser His His Thr His
    610                 615

<210> SEQ ID NO 17
<211> LENGTH: 3037
<212> TYPE: DNA
<213> ORGANISM: Halocyphina villosa
<220> FEATURE:
<221> NAME/KEY: CDS
<222> LOCATION: (260)..(388)
<220> FEATURE:
<221> NAME/KEY: CDS
<222> LOCATION: (444)..(494)
<220> FEATURE:
<221> NAME/KEY: CDS
<222> LOCATION: (559)..(663)
<220> FEATURE:
<221> NAME/KEY: CDS
<222> LOCATION: (713)..(727)
<220> FEATURE:
<221> NAME/KEY: CDS
<222> LOCATION: (779)..(802)
<220> FEATURE:
<221> NAME/KEY: CDS
```

<222> LOCATION: (850)..(975)
<220> FEATURE:
<221> NAME/KEY: CDS
<222> LOCATION: (1024)..(1134)
<220> FEATURE:
<221> NAME/KEY: CDS
<222> LOCATION: (1188)..(1286)
<220> FEATURE:
<221> NAME/KEY: CDS
<222> LOCATION: (1333)..(1434)
<220> FEATURE:
<221> NAME/KEY: CDS
<222> LOCATION: (1515)..(1575)
<220> FEATURE:
<221> NAME/KEY: CDS
<222> LOCATION: (1625)..(1845)
<220> FEATURE:
<221> NAME/KEY: CDS
<222> LOCATION: (1973)..(2140)
<220> FEATURE:
<221> NAME/KEY: CDS
<222> LOCATION: (2187)..(2201)
<220> FEATURE:
<221> NAME/KEY: CDS
<222> LOCATION: (2249)..(2311)
<220> FEATURE:
<221> NAME/KEY: CDS
<222> LOCATION: (2367)..(2414)
<220> FEATURE:
<221> NAME/KEY: CDS
<222> LOCATION: (2463)..(2489)
<220> FEATURE:
<221> NAME/KEY: CDS
<222> LOCATION: (2542)..(2646)
<220> FEATURE:
<221> NAME/KEY: CDS
<222> LOCATION: (2697)..(2834)

<400> SEQUENCE: 17

```
tggggagatg gttctatata tcaaaatgat cttctgtcct gagctttcct cgtccttgtt      60
ttcgtcttgt cagtgccgcg acatgctttt attaaaccat ggcgagctg cccgcgccca     120 aggagatagc ataatcgcct gagaaaccta gtcgtcat ggccgtgtaa ccgttcttgc     180
gacttatttt cgcacttctc tcagaatata aaggcctatt gtgatacggt tcatctaacc     240
ccagcgtccc ctccgaaaag atg ggc tgc ctc tca ctc ttc gca ttc ctt act    292
              Met Gly Cys Leu Ser Leu Phe Ala Phe Leu Thr
              1               5                   10 gct tta aac tca gtt cat gcc gct gtg ggt ccc gtt acg gac tta aca      340
Ala Leu Asn Ser Val His Ala Ala Val Gly Pro Val Thr Asp Leu Thr
          15                  20                  25 ctg atc gta gat act gtc gcc ccc gac ggt gct gct ttc gcg cgg gaa      388
Leu Ile Val Asp Thr Val Ala Pro Asp Gly Ala Ala Phe Ala Arg Glu
     30                  35                  40 ggtgagactt tgcgactgta aatgccggat ttgagtttct aattataatc ttcca gcc     446
                                                              Ala att gtc gtc caa gag gaa cca aac tcc gtc att ggt ccg gtc atc gta      494
Ile Val Val Gln Glu Glu Pro Asn Ser Val Ile Gly Pro Val Ile Val
45                  50                  55                  60 ggtgggtagc tacgagtctt cctccttcat ttagctcatc accaagtgat atgatattaa    554 ttaa ggt caa aag ggg gac aac ttt cgg ctc aat gtt atc aac aat ttg     603
     Gly Gln Lys Gly Asp Asn Phe Arg Leu Asn Val Ile Asn Asn Leu
             65                  70                  75 gat tct ccg aac atg cgc caa tct act tcc att cat tgg cat ggc atc     651
Asp Ser Pro Asn Met Arg Gln Ser Thr Ser Ile His Trp His Gly Ile
         80                  85                  90 ttc caa gga aac ggtacgtggt atatcggata atctatctgt atccattgac         703
Phe Gln Gly Asn
         95
```

```
tcgaatata ggt cag aat tgg gct ggtgcgttgg ccttcctgaa gcctgctcga      757
         Gly Gln Asn Trp Ala
                 100 atttatcttc ctgaattttt a gat ggc gcc gca ttc gtt aac cag            802
                        Asp Gly Ala Ala Phe Val Asn Gln
                                       105 gtaaggagat gttcctgcct tcgtttcccc agaactaatt atcctag tgc ccc att    858
                                                   Cys Pro Ile
                                                           110 gcc ccc gga ggg gac tcg ttc ttg tac gac ttt acc gaa cct ttc cag    906
Ala Pro Gly Gly Asp Ser Phe Leu Tyr Asp Phe Thr Glu Pro Phe Gln
            115                 120                 125 act ggc aca ttt tgg tat cat tcc cat tta tca act caa tac tgc gat    954
Thr Gly Thr Phe Trp Tyr His Ser His Leu Ser Thr Gln Tyr Cys Asp
        130                 135                 140 gga ctg agg gga gca ttc gtc gttcgttctc ttcttcatca agtcaccgct      1005
Gly Leu Arg Gly Ala Phe Val
    145                 150 ttcttctcac ttatctag atc tac gat ccg ctc gac cct tac cgg ttg ctc   1056
                    Ile Tyr Asp Pro Leu Asp Pro Tyr Arg Leu Leu
                                        155                 160 tac gat gtc gac gac gag tcg act gtg att act ctg gcg gac tgg tac   1104
Tyr Asp Val Asp Asp Glu Ser Thr Val Ile Thr Leu Ala Asp Trp Tyr
            165                 170                 175 cac agc tat gcg gag gac att cta atc gcg taggagattt tcccaagatg     1154
His Ser Tyr Ala Glu Asp Ile Leu Ile Ala
            180                 185 tctcctctgc ctctctgaaa tccatgaact agt gca ggc gac act atc ctc atc  1208
                                Ala Gly Asp Thr Ile Leu Ile
                                                    190 aat ggt cac gga aga ttc gcc gga gcc ggc gga acg gca aca gaa cta   1256
Asn Gly His Gly Arg Phe Ala Gly Ala Gly Gly Thr Ala Thr Glu Leu
195                 200                 205                 210 tct gtc att act gtt gag cat gga aag cgg taggcattct ccctcggctt     1306
Ser Val Ile Thr Val Glu His Gly Lys Arg
            215                 220 tgtagatgtg tctaatttgt gatagc tac cga ttg cga ttt gcc aat atc gct  1359
                             Tyr Arg Leu Arg Phe Ala Asn Ile Ala
                                             225 tgt gac cct tgg ttt gcc gtg aaa atc gat agc cat acg aac ctt cgc   1407
Cys Asp Pro Trp Phe Ala Val Lys Ile Asp Ser His Thr Asn Leu Arg
230                 235                 240                 245 gtt atc gaa gct gac ggt att act act gtgcctgtca cggtggactc         1454
Val Ile Glu Ala Asp Gly Ile Thr Thr
                250 cttcaatgta ggcttaccct tagcactttc ccactctgga tcctcttatg acttcccaag 1514 atc ttt gtg ggc caa cga tat agt gtc atc ctc cat gcc aac cag cct  1562
Ile Phe Val Gly Gln Arg Tyr Ser Val Ile Leu His Ala Asn Gln Pro
255                 260                 265                 270 gtt gga aac tac t gtaagctgcc taaatgttgc atgactgtcc atgattctaa    1615
Val Gly Asn Tyr ccccgccag gg  att cgg gcc gct ccg aac ggc gtg agc aat ttc gcg ggt 1665
             Trp Ile Arg Ala Ala Pro Asn Gly Val Ser Asn Phe Ala Gly
                 275                 280                 285 ggg atc gac tcg gct att ctc cgt tat gtt ggc gcc cca gaa gaa gag  1713
Gly Ile Asp Ser Ala Ile Leu Arg Tyr Val Gly Ala Pro Glu Glu Glu
            290                 295                 300 ccc aac act agt gag gat act cca tcc gac aca ctt caa gag cag gat  1761
Pro Asn Thr Ser Glu Asp Thr Pro Ser Asp Thr Leu Gln Glu Gln Asp
```

```
                    305                 310                 315                 320
ctt cac ccg ctg atc cta ccc ggc gcg cca ggc atc cac tcc cgt ggg                  1809
Leu His Pro Leu Ile Leu Pro Gly Ala Pro Gly Ile His Ser Arg Gly
                325                 330                 335 gcc gcc gac gtt gtc cac acc gta tca atg gag ttt gtgagtgtgg                       1855
Ala Ala Asp Val Val His Thr Val Ser Met Glu Phe
            340                 345 cgacttttct ggccccctttt attaatataa tctggttagg atggcgcaaa cttccaattc               1915
ctcctggatg gcgtggcctt ccagccgtgc gtcatctctt caaagaatt tatctag                    1972 ctg acg att ttg aaa tgt agc ccg acc atg ccc gtc ctt ctg caa ata                  2020
Leu Thr Ile Leu Lys Cys Ser Pro Thr Met Pro Val Leu Leu Gln Ile
350                 355                 360 tta tcg gga gcg cag act gct aat acc ctt ctc ccg gcg gga tcc ttt                  2068
Leu Ser Gly Ala Gln Thr Ala Asn Thr Leu Leu Pro Ala Gly Ser Phe
365                 370                 375                 380 atc caa gcg tcg cac aat gac atc gtg gag ctc aat ttc cca gct gtc                  2116
Ile Gln Ala Ser His Asn Asp Ile Val Glu Leu Asn Phe Pro Ala Val
                385                 390                 395 aac gta gcc gct gtc ggt gga ccg tgcgtcccat ctttccttgc cagcttgaaa                 2170
Asn Val Ala Ala Val Gly Gly Pro
            400 tttacgctct tttaga cat cca atc cat ctg tgagcgcagc gggacctttg                      2221
               His Pro Ile His Leu
                    405 gcttatggca tatgacttat tattagc cat ggc cat gca ttc gac gtt ata cgc                2275
                            His Gly His Ala Phe Asp Val Ile Arg
                                410                 415 tct gct gga acg aac tcc gat aac tgg ttc aat ccg gtattttcat                       2321
Ser Ala Gly Thr Asn Ser Asp Asn Trp Phe Asn Pro
420                 425                 430 tcgacttcca taagatgacg atggctcact atggttttta cccag cct cgc aga gat                2378
                                                   Pro Arg Arg Asp gtc gta tcc acc ggt acc gat cct aat gac aat gtg tacgtgtttc                       2424
Val Val Ser Thr Gly Thr Asp Pro Asn Asp Asn Val
435                 440                 445 gctattgatt gtccgttttg atttgactgt tggacagc acc att cgc ttc cgg gcc                2480
                                           Thr Ile Arg Phe Arg Ala
                                                            450 gac aac ccg tacgtaaact gctgaatctc tcgttgtctt tggttctcat                          2529
Asp Asn Pro
        455 aatctcatca ga ggt cca tgg ttc ctt cac tgc cac att gac tgg cac ctt               2580
              Gly Pro Trp Phe Leu His Cys His Ile Asp Trp His Leu
                            460                 465 gaa ctc ggc ttt gct ttg gtg att gca gaa gcg cct agc gaa tgg gac                  2628
Glu Leu Gly Phe Ala Leu Val Ile Ala Glu Ala Pro Ser Glu Trp Asp
    470                 475                 480 agc gac att aac cct cct ggtgcgctgc ctgtgaacct tttctcccta                         2676
Ser Asp Ile Asn Pro Pro
485                 490 cacttgctaa gatcgctcta gct gcg tgg gat gac cta tgc cct acg ttc gct                2729
                        Ala Ala Trp Asp Asp Leu Cys Pro Thr Phe Ala
                                495                 500 tgg ctt ctc ttt tac tat ttc aag ttt cct cac att ctc aac ttc aca                  2777
Trp Leu Leu Phe Tyr Tyr Phe Lys Phe Pro His Ile Leu Asn Phe Thr
            505                 510                 515 gat atg atg ccc tgc cgc ctg agc agc agt aat cga gtt aag aac ctc                  2825
Asp Met Met Pro Cys Arg Leu Ser Ser Ser Asn Arg Val Lys Asn Leu
        520                 525                 530
```

```
aac gtt gac taaggaaaaa gcaaagcaga atatgaaact ctcatttatc    2874
Asn Val Asp
    535 tttatatcga cacattcact attcaaccta cggattttcc ctcgcacctg aatttcggtg    2934 ctagatcccc atccttggtg gagtaggaaa gaaatttctt gtataaaacc catgggttct    2994 tctaccaata tatacataac gtccgtgggg ttagttaatt cgt    3037
```

<210> SEQ ID NO 18
<211> LENGTH: 536
<212> TYPE: PRT
<213> ORGANISM: Halocyphina villosa

<400> SEQUENCE: 18

```
Met Gly Cys Leu Ser Leu Phe Ala Phe Leu Thr Ala Leu Asn Ser Val
1               5                   10                  15

His Ala Ala Val Gly Pro Val Thr Asp Leu Thr Leu Ile Val Asp Thr
            20                  25                  30

Val Ala Pro Asp Gly Ala Ala Phe Ala Arg Glu Ala Ile Val Val Gln
        35                  40                  45

Glu Glu Pro Asn Ser Val Ile Gly Pro Val Ile Val Gly Gln Lys Gly
    50                  55                  60

Asp Asn Phe Arg Leu Asn Val Ile Asn Asn Leu Asp Ser Pro Asn Met
65                  70                  75                  80

Arg Gln Ser Thr Ser Ile His Trp His Gly Ile Phe Gln Gly Asn Gly
                85                  90                  95

Gln Asn Trp Ala Asp Gly Ala Ala Phe Val Asn Gln Cys Pro Ile Ala
            100                 105                 110

Pro Gly Gly Asp Ser Phe Leu Tyr Asp Phe Thr Glu Pro Phe Gln Thr
        115                 120                 125

Gly Thr Phe Trp Tyr His Ser His Leu Ser Thr Gln Tyr Cys Asp Gly
    130                 135                 140

Leu Arg Gly Ala Phe Val Ile Tyr Asp Pro Leu Asp Pro Tyr Arg Leu
145                 150                 155                 160

Leu Tyr Asp Val Asp Asp Glu Ser Thr Val Ile Thr Leu Ala Asp Trp
                165                 170                 175

Tyr His Ser Tyr Ala Glu Asp Ile Leu Ile Ala Ala Gly Asp Thr Ile
            180                 185                 190

Leu Ile Asn Gly His Gly Arg Phe Ala Gly Ala Gly Thr Ala Thr
        195                 200                 205

Glu Leu Ser Val Ile Thr Val Glu His Gly Lys Arg Tyr Arg Leu Arg
    210                 215                 220

Phe Ala Asn Ile Ala Cys Asp Pro Trp Phe Ala Val Lys Ile Asp Ser
225                 230                 235                 240

His Thr Asn Leu Arg Val Ile Glu Ala Asp Gly Ile Thr Thr Ile Phe
                245                 250                 255

Val Gly Gln Arg Tyr Ser Val Ile Leu His Ala Asn Gln Pro Val Gly
            260                 265                 270

Asn Tyr Trp Ile Arg Ala Ala Pro Asn Gly Val Ser Asn Phe Ala Gly
        275                 280                 285

Gly Ile Asp Ser Ala Ile Leu Arg Tyr Val Gly Ala Pro Glu Glu Glu
    290                 295                 300

Pro Asn Thr Ser Glu Asp Thr Pro Ser Asp Thr Leu Gln Glu Gln Asp
305                 310                 315                 320

Leu His Pro Leu Ile Leu Pro Gly Ala Pro Gly Ile His Ser Arg Gly
```

-continued

```
                    325                 330                 335
Ala Ala Asp Val Val His Thr Val Ser Met Glu Phe Leu Thr Ile Leu
            340                 345                 350

Lys Cys Ser Pro Thr Met Pro Val Leu Leu Gln Ile Leu Ser Gly Ala
            355                 360                 365

Gln Thr Ala Asn Thr Leu Leu Pro Ala Gly Ser Phe Ile Gln Ala Ser
        370                 375                 380

His Asn Asp Ile Val Glu Leu Asn Phe Pro Ala Val Asn Val Ala Ala
385                 390                 395                 400

Val Gly Gly Pro His Pro Ile His Leu His Gly His Ala Phe Asp Val
            405                 410                 415

Ile Arg Ser Ala Gly Thr Asn Ser Asp Asn Trp Phe Asn Pro Pro Arg
            420                 425                 430

Arg Asp Val Val Ser Thr Gly Thr Asp Pro Asn Asp Asn Val Thr Ile
            435                 440                 445

Arg Phe Arg Ala Asp Asn Pro Gly Pro Trp Phe Leu His Cys His Ile
        450                 455                 460

Asp Trp His Leu Glu Leu Gly Phe Ala Leu Val Ile Ala Glu Ala Pro
465                 470                 475                 480

Ser Glu Trp Asp Ser Asp Ile Asn Pro Pro Ala Ala Trp Asp Asp Leu
            485                 490                 495

Cys Pro Thr Phe Ala Trp Leu Leu Phe Tyr Tyr Phe Lys Phe Pro His
            500                 505                 510

Ile Leu Asn Phe Thr Asp Met Met Pro Cys Arg Leu Ser Ser Ser Asn
            515                 520                 525

Arg Val Lys Asn Leu Asn Val Asp
        530                 535
```